US008846030B2

(12) United States Patent
Engelhardt et al.

(10) Patent No.: US 8,846,030 B2
(45) Date of Patent: Sep. 30, 2014

(54) COMPOUNDS AND METHODS TO ENHANCE RAAV TRANSDUCTION

(75) Inventors: John F. Engelhardt, Iowa City, IA (US); Dongsheng Duan, Columbia, MO (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 11/301,601

(22) Filed: Dec. 13, 2005

(65) Prior Publication Data

US 2006/0093585 A1  May 4, 2006

Related U.S. Application Data

(60) Division of application No. 09/689,136, filed on Oct. 12, 2000, now Pat. No. 7,122,335, which is a continuation of application No. PCT/US00/15700, filed on Jun. 8, 2000.

(60) Provisional application No. 60/138,188, filed on Jun. 8, 1999, provisional application No. 60/201,089, filed on May 2, 2000.

(51) Int. Cl.
*A61K 48/00* (2006.01)
*C12N 7/01* (2006.01)
*C12N 15/864* (2006.01)
*C12Q 1/70* (2006.01)

(52) U.S. Cl.
USPC ......... 424/93.6; 435/456; 435/325; 435/69.1; 435/6.13; 514/44

(58) Field of Classification Search
CPC ................ A61K 48/0083; A61K 2039/5256; C12N 2799/025; C12N 15/8645; C12N 2750/14143; C12N 2750/14145
See application file for complete search history.

(56) References Cited

U.S. PATENT DOCUMENTS

| | | | |
|---|---|---|---|
| 4,501,729 A | 2/1985 | Boucher et al. |
| 5,292,498 A | 3/1994 | Boucher, Jr. |
| 5,512,269 A | 4/1996 | Molina y Vedia et al. |
| 5,604,090 A | 2/1997 | Alexander et al. |
| 5,628,984 A | 5/1997 | Boucher, Jr. |
| 5,635,160 A | 6/1997 | Stutts, III et al. |
| 5,651,957 A | 7/1997 | Molina y Vedia et al. |
| 5,656,256 A | 8/1997 | Boucher et al. |
| 5,683,675 A | 11/1997 | Molina y Vedia et al. |
| 5,691,176 A | 11/1997 | Lebkowski et al. |
| 5,716,931 A | 2/1998 | Molina y Vedia et al. |
| 5,725,842 A | 3/1998 | Boucher, Jr. et al. |
| 5,801,030 A | 9/1998 | McVey et al. |
| 5,831,068 A | 11/1998 | Nair et al. |
| 5,834,182 A | 11/1998 | Alexander et al. |
| 5,843,742 A | 12/1998 | Natsoulis et al. |
| 5,849,706 A | 12/1998 | Molina y Vedia et al. |
| 5,855,918 A | 1/1999 | Mrsny et al. |
| 5,876,700 A | 3/1999 | Boucher, Jr. et al. |
| 5,902,567 A | 5/1999 | Boucher, Jr. |
| 5,935,555 A | 8/1999 | Stutts, III et al. |
| 6,022,527 A | 2/2000 | Boucher, Jr. et al. |
| 6,033,688 A | 3/2000 | Mrsny et al. |
| 6,037,177 A | 3/2000 | Snyder |
| 6,083,702 A | 7/2000 | Mitchell et al. |
| 6,133,247 A | 10/2000 | Boucher, Jr. |
| 6,143,279 A | 11/2000 | Boucher, Jr. et al. |
| 6,156,303 A | 12/2000 | Russell et al. |
| 6,200,560 B1 | 3/2001 | Couto et al. |
| 6,214,536 B1 | 4/2001 | Boucher, Jr. |
| 6,221,349 B1 | 4/2001 | Couto et al. |
| 6,235,266 B1 | 5/2001 | Stutts, III et al. |
| 6,264,975 B1 | 7/2001 | Boucher, Jr. |
| 6,270,996 B1 | 8/2001 | Wilson et al. |
| 6,287,569 B1 | 9/2001 | Kipps et al. |
| 6,290,951 B1 | 9/2001 | Mikulski et al. |
| 6,323,187 B1 | 11/2001 | Yerxa et al. |
| 6,416,759 B1 | 7/2002 | Firestone et al. |
| 6,420,347 B1 | 7/2002 | Jacobus et al. |
| 6,436,392 B1 | 8/2002 | Engelhardt et al. |
| 6,451,288 B1 | 9/2002 | Boucher, Jr. et al. |
| 6,475,509 B1 | 11/2002 | Boucher, Jr. |
| 6,475,537 B1 | 11/2002 | King et al. |
| 6,544,786 B1 | 4/2003 | Xiao et al. |
| 6,586,416 B2 | 7/2003 | Bubien |
| 6,607,741 B2 | 8/2003 | Boucher, Jr. |
| 6,613,345 B2 | 9/2003 | Boucher, Jr. |
| 6,855,549 B1 | 2/2005 | McCray, Jr. et al. |
| 6,897,045 B2 | 5/2005 | Engelhardt et al. |
| 7,060,497 B2 | 6/2006 | Nakai et al. |
| 7,122,335 B1 | 10/2006 | Engelhardt et al. |

(Continued)

FOREIGN PATENT DOCUMENTS

| | | |
|---|---|---|
| AU | 4091299 | 12/1999 |
| CA | 2302627 | 9/2001 |

(Continued)

OTHER PUBLICATIONS

Enzyme database entry for EC No. 3.4.22, http://ca.expasy.org/enzyme/3.4.22.-, downloaded Jun. 19, 2007.*
Verma et al. (1997) Nature 389:239-242.*
Marshall (1995) Science 269:1050-1055.*
Orkin et al. (1995) Report and recommendations of the panel to assess the NIH investment in research on gene therapy, available at http://web.archive.org/web/20000816012254/http://www.nih.gov/news/panelrep.html.*
Eck et al. (1996) Goodman & Gilman's The Pharmacological Basis of Therapeutics, 9th Edition, Chapter 5, McGraw-Hill, NY.*

(Continued)

*Primary Examiner* — Maria Marvich

(74) *Attorney, Agent, or Firm* — Schwegman Lundberg & Woessner, P.A.

(57) ABSTRACT

Agents and methods to alter rAAV transduction are provided.

25 Claims, 27 Drawing Sheets

(56) References Cited

U.S. PATENT DOCUMENTS

| | | | |
|---|---|---|---|
| 7,749,491 | B2* | 7/2010 | Engelhardt et al. .......... 424/93.1 |
| 2001/0034349 | A1 | 10/2001 | Boucher, Jr. |
| 2001/0041682 | A1 | 11/2001 | Stutts, III et al. |
| 2002/0076754 | A1 | 6/2002 | Sun et al. |
| 2002/0099023 | A1 | 7/2002 | Boucher, Jr. |
| 2002/0115619 | A1 | 8/2002 | Rubenstein et al. |
| 2002/0128203 | A1 | 9/2002 | Schild |
| 2002/0131956 | A1 | 9/2002 | Walsh et al. |
| 2002/0132770 | A1 | 9/2002 | Caplan et al. |
| 2002/0156057 | A1 | 10/2002 | Bubien |
| 2002/0158255 | A1 | 10/2002 | Boucher, Jr. |
| 2002/0165239 | A1 | 11/2002 | Boucher, Jr. |
| 2002/0197237 | A1 | 12/2002 | Engelhardt et al. |
| 2003/0003583 | A1 | 1/2003 | Hirsch et al. |
| 2003/0087818 | A1 | 5/2003 | Jiang et al. |
| 2003/0103939 | A1 | 6/2003 | Engelhardt et al. |
| 2004/0248301 | A1 | 12/2004 | Engelhardt et al. |
| 2005/0037497 | A1 | 2/2005 | Engelhardt et al. |
| 2005/0095225 | A1 | 5/2005 | Engelhardt et al. |
| 2005/0158281 | A1 | 7/2005 | Chamberlain et al. |
| 2005/0181423 | A1 | 8/2005 | Barak et al. |
| 2005/0255087 | A1 | 11/2005 | Engelhardt et al. |
| 2006/0093585 | A1 | 5/2006 | Engelhardt et al. |
| 2008/0206198 | A1 | 8/2008 | Engelhardt et al. |
| 2008/0213221 | A1 | 9/2008 | Engelhardt et al. |
| 2008/0249050 | A1 | 10/2008 | Engelhardt et al. |
| 2009/0017062 | A1 | 1/2009 | Engelhardt et al. |

FOREIGN PATENT DOCUMENTS

| | | | |
|---|---|---|---|
| EP | 0041682 | A1 | 12/1981 |
| EP | 0132770 | A1 | 2/1985 |
| EP | 0158255 | A2 | 10/1985 |
| EP | 1153612 | A1 | 11/2001 |
| EP | 1486567 | A1 | 12/2004 |
| JP | 2003501068 | | 1/2003 |
| WO | WO-94/13788 | | 6/1994 |
| WO | WO-95/07351 | | 3/1995 |
| WO | WO-95/15384 | | 6/1995 |
| WO | WO-9610402 | A1 | 4/1996 |
| WO | WO-97/22250 | | 6/1997 |
| WO | WO-98/09657 | | 3/1998 |
| WO | WO-98/24479 | | 6/1998 |
| WO | WO-9853839 | | 12/1998 |
| WO | WO-9853839 | A2 | 12/1998 |
| WO | WO-99/60146 | | 11/1999 |
| WO | WO-00/47220 | | 2/2000 |
| WO | WO-00/75365 | | 12/2000 |
| WO | WO-0075365 | A2 | 12/2000 |
| WO | WO-0075365 | A3 | 12/2000 |
| WO | WO-0125465 | A1 | 4/2001 |
| WO | WO-01/83692 | | 11/2001 |
| WO | WO-0224172 | A1 | 3/2002 |
| WO | WO-0224177 | A2 | 3/2002 |
| WO | WO-02087306 | A2 | 11/2002 |
| WO | WO-03057847 | A2 | 7/2003 |
| WO | WO-03095667 | a2 | 11/2003 |
| WO | WO-2004089423 | A2 | 10/2004 |
| WO | WO-2004089423 | A3 | 10/2004 |
| WO | WO-2004090145 | A2 | 10/2004 |
| WO | WO-2004090145 | A3 | 10/2004 |
| WO | WO-2004112727 | A2 | 12/2004 |
| WO | WO-2005116224 | A2 | 12/2005 |
| WO | WO-2005119251 | A2 | 12/2005 |
| WO | WO-2007127464 | A2 | 11/2007 |
| WO | WO 2009028387 | * | 5/2009 |

OTHER PUBLICATIONS

Ross et al. Human gene Therapy, vol. 7, pp. 1781-1790, Sep. 1996.*
Rubanyi (2001) Mol. Aspects Med. 22:113-142.*
Carter (2005) Hum. Gene Ther. 16:541-550.*
Thakur et al, Strategies for ocular siRNA delivery: Potential and limitations of non-viral nanocarriers, Journal of Biological Engineering 2012, 6:pp. 1-7.*
Serwer et al, Systemic and Local Drug Delivery for Treating Diseases of the Central Nervous System in Rodent Models, JOVE, 2010 vol. 42, p. 1-6.*
Russell, S. J., Replicating Vectors for Gene Therapy of Cancer: Risks, Limitations and Prospects, European J Cancer, 1994, vol. 30A (8), pp. 1165-1171.*
Tenenbaum et al, Evaluation of Risks Related to the Use of Adeno-Associated Virus-Based Vectors, Current Gene Therapy, 2003, 3, 545-565.*
Hansen et al, Impaired Intracellular Trafficking of Adeno-Associated Virus Type 2 Vectors Limits Efficient Transduction of Murine Fibroblasts, Journal of Virology, Jan. 2000, p. 992-996.*
Doll, RF, et al., "Comparison of promoter strengths on gene delivery into mammalian brain cells using AAV vectors", *Gene Therapy* (3), (1996),437-447.
"(S)-(+)-Camptothecin; 4-Ethyl-4-hydroxy-1H-pyrano[3', 4': 6,7] indolizino [1,2-b] quinoline-3, 14 (4H, 12H) dione", *Calbiochem*, Camptothecin, Camptotheca acuminata, (Oct. 2, 2000), 1-2.
"Adriamycin; 14-Hydroxydaunomycin, HCI", *Calbiochem*, Doxorubicin, Hydrochloride, Catalog No. 324380,(Oct. 21, 1998),1-2.
"Aminoglycoside antibiotic. Inhibits myeloperoxidase-dependent oxidant cell injury", *Calbiochem*, Tobramycin, Free Base, Catalog No. 614005,(Aug. 26, 1999),1.
"Cancer Research", *Contribution to Society*, http://www.bikaken.or.jp/mcrf_e/contributiion,(Dec. 4, 2000),2 pages.
"Carbobenzoxy-L-leucyl-L-leucinal", *Calbiochem*, MG-132, Catalog No. 474790,(Oct. 15, 1999),1-2.
"Drugs for Selection of Genetic Markers Reagents for positive and negative selection of Genes involved in Nucleotide Metabolism", *Calbiochem*, (Mar. 2002),6 pages.
"EPA; 20:5 w-3; 5,8, 11, 14, 17-Eicosapentaenoic Acid" *Calbiochem*, Eicosapentaenoic Acid, Catalog No. 324875,(Dec. 7, 1998),1-2.
"Epoxomicin—a potent and selective proteasome inhibitor", *Affiniti Research Products Limited*, 2 pages.
"International Search Report for corresponding PCT Application No. PCT/US2004/010045",(Jan. 10, 2005),6 pgs.
"LDP-341", *Millennium Pharmaceuticals*, http://www.biospace.com/ct/detail.cfm?ClinicalID=266404,1 page.
"Mevinolin; MK-803", *Calbiochem*, Lovastatin, Catalolg No. 438185,(Jun. 29, 2001), 1-2.
"MK-733", *Calbiochem*, Simvastatin, Catalog No. 567020,(Oct. 25, 2001),2.
"PCT International Search Report from International Application No. PCT/US02/21926", (Oct. 15, 2002),4 pages.
"Polymer Vectors Endosomal release and cytoplasmic delivery", *Endosomal Release*, http://web.bham.ac.uk/can4psd4/nonviral/endosome.html,(Jun. 3, 2001),1.
"Product Data Sheet", *Moravek Biochemicals, Inc.*, M-1535, Ritonavir,(Jul. 12, 2001), 1 page.
"Product Information", *Sigma*, Cyclosporin A, Sigma Product No. C3662,(Oct. 28, 1996),3 pages.
"Product Information", *Sigma*, Bleomycin Sulfate, Sigma Prod. No. B5507,(Nov. 25, 1996),2 pages.
"Proteasome Inhibitors", *Peptides International, Inc.*, (Apr. 16, 2001),1-2.
"Tannic Acid, A.C.S. reagent", *Sigma*, www.sigma-aldrich.com/sacatolog.nsf/productlookup/Aldrich403040?OpenDocument,1 page.
Adams, Julian, "Novel Inhibitors of the Proteasome and Their Theraputic Use in Inflammation", *Annual Reports in Medicinal Chemistry*, Academic Press, Inc.,(1996),279-288.
Alberts, Bruce, et al., "Molecular Biology of the Cell", 3rd edition, (1994),618-626.
Alexander, Ian E., et al., "DNA-Damaging Agents Greatly Increase the Transduction of Nondividing Cells by Adeno-Associated Virus Vectors", *Journal of Virology*, 68 (12), (Dec. 1994),8282-8287.
Alexander, I E., et al., "Effects of Gamma Irradiation on the Transduction of Dividing and Nondviding Cells in Brain and Muscle of Rats by Adeno-Associated Virus Vectors", *Human Gene Therapy*, 7(7), (May 1, 1996),841-850.

(56) References Cited

OTHER PUBLICATIONS

Andre, Patrice, et al., "An inhibitor of HIV-1 protease modulates proteasome activity, antigen presentation, and T cell responses", *Proc. National Academy of Science USA*, vol. 95 (Oct. 1998),13120-13124.

Arcamone, F M., "From the Plgments of the Actinomycetes to Third Generation Antitumor Anthracyclines", *Biochimie*(Paris), 80(3), (Mar. 1998)201-206.

Auerbach, S. D., et al., "Human Amiloride-Sensitive Epithelial Na+ Channel y Subunit Promoter: Functional Analysis and Identification Polypurine-Polypyrimidine Tract With the Potential for Triplex DNA Formation", *Biochem. J., 3476*, (2000),105-114.

Baines, D. L., et al., "Effect of LPS-Induced NF-kB Activity on the Transcriptional Response of a 5' Flanking Region of the alphaENaC Gene", *Experimental Biology 2003—Translating the Genome*, Abstract No. 5860 (http://www.biosis-select.org/faseb/data/FASEB005860.html,(2003),1 pg.

Banerjee, D., et al., "The Treatment of Respiratory *Pseudomonas* Infection in Cystic Fibrosis: What Drug and Which Way?", *Drugs*, 60(5), (Abstract Only), (Nov. 2000), 1 pg.

Bank, U., "Review: Peptidases and Peptidase Inhibitors in the Pathogenesis of Diseases", *Cellular Peptidases in Immune Functions and Diseases 2*, (Edited by Jurgen Langner, et al., Kluwer Academic / Plenum Publishers),(2000),349-378.

Bartlett, Jeffrey S., et al., "Infectious entry pathway of adeno-associated virus and adeno-associated virus vectors", *Journal of Virology*, 74(6), (Mar. 2000),2777-2785.

Bartlett, J S., et al., "Targeted adeno-associated virus vector transduction of nonpermissive cells mediated by a bispecific F(ab'gamma)2 antibody", *Nature Biotechnology, 17*, (1999),pp. 181-186.

Basak, S, et al., "Infectious Entry Pathways for Canine Parvovirus", *Virology*, 186(2), (Feb. 1992),368-376.

Berns, K. I., et al., "Biology of Adeno-associated Virus", *In: Current Topics in Microbiology and Immunology, 218*, Springer-Verlag, Berlin: R.W. Compans, et al., (Eds.),(1996),pp. 1-23.

Berns, K. I., "Parvovirus Replication", *Microbiological Reviews*, 54 (3), (Sep. 1990),pp. 316-329.

Beutler, K. T., et al., "Long-Term Regulation of ENaC Expression in Kidney by Angiotensin II", *Hypertension, 41*, (2003),1143-1150.

Bies, J., et al., "Oncogenic activation of c-Myb by Carboxyl-Terminal truncation leads to Decreased Proteolysis by the Ubiquitin-26S proteasome pathway", *Oncogene*, 14(2), Abstract,(Jan. 16, 1997),1 page.

Bokkala, Shaila, et al., "Angiotensin II-induced Down-regulation of Inositol Trisphosphate Receptors in WB Rat Liver Epithelial Cells", *Journal of Biological Chemistry*, 272(19), (May 9, 1997), 12454-1261.

Bonacorsi, Stephane, et al., "Comparative In Vitro Activities of Meropenem, Impenem, Temocillin, Piperacillin, and Ceftazidime in Combination with Tobramycin, Rifampin, or Ciprofloxacin against Burkholderia cepacia Isolates from Patients with Cystic Fibrosis", *Antimicrobial Agents and Chemotherapy*, vol. 43 No. 2, (Feb. 1999),213-217.

Booth, R. E., et al., "Targeted Degradation of ENaC in Response to PKC Activation of the ERK1/2 Cascase", *Am. J. Physiol. Renal Physiol,. 284,*, (2003),F938-F947

Brand, Stephen, et al., "Role of the Proteasome in Rat Indomethacin-Induced Gastropathy", *Gastroenterology*, vol. 116, No. 4, (1999),865-873.

Bravo, Laura, "Polyphenols: Chemistry, Dietary Sources, Metabolism and Nutritional Significance", *Nutrition Reviews*, vol. 56. No. 11 (Nov. 1998),317-333.

Brotz, H., "The Lantibiotic Mersacidin Inhibits Peptidoglycan Biosynthesis and the Level of Transglycosylation", *Eur. J. Biochem.*, 246(1), (1997),193-199.

Bugg, C., et al., "SRI6975 Increases Adenovirus Mediated Gene Transfer Through the Apical Surface of Polarized MDCK Cell Monolayers", *Cystic Fibrosis Foundation: 2000 North American CF Conference*, (Nov. 2000),1.

Cantin, Andre M., et al., "Aerosolized Prolastin Suppresses Bacterial Proliferation in a Model of Chronic *Pseudomonas aeruginosa* Lung Infection", *American Journal of Respiratory and Critical Care Medicine*, vol. 160, (1999),1130-1135.

Chu, Q, et al., "Binding and uptake of Cationic Lipid: pDNA Complexes by Polarized Airway Epithelial Cells", *Human Gene Therapy, 10*, (1999),pp. 25-36.

Chung, King-Thom, et al., "Tannis and Human Health: A Review", *Critical Reviews in Food Science and Nutrition*, 38(6), (1998),421-464.

Coonrod, A, et al., "On the mechanism of DNA transfection: effcent gene transfer without viruses", *Gene Therapy, 4*, (1997),pp. 1313-1321.

Desai, Shyamal, et al., "Ubiquitin-dependent Destruction of Topoisomerase I Is Stimulated by the Antitumor Drug Camptothecin", *Journal of Biological Chemistry*, 272(39), (Sep. 26, 1997),24159-24164.

Dietrich, Cornelia, et al., "p53-Dependent cell cycle arrest induced by N-acetyl-L-leucinyl-L-leucinyl-L-norleucinal in platelet-derived growth factor-stimulated human fibroblasts", *Proc. of the Nat'l Academy of Sciences of the US*, vol. 93, No. 20, XP002154340,(1996),10815-10819.

Ding, W., et al., "Second-Strand Genome Conversion of Adeno-Associated Virus Type 2 (AAV-2) and AAV-5 is Not Rate Limiting Following Apical Infection of Polarized Human Airway Epithelia", *Journal of Virology*, 77(13), (2003),7361-7366.

Donaldson, S. H., "Regulation of the Epithelial Sodium Channel by Serine Proteases in Human Airways", *The Journal of Biological Chemistry*, 277(10), (2002),8338-8345

Douar, A.-M., et al., "Intracellular Trafficking of Adeno-Associated Virus Vectors: Routing to the Late Endosomal Compartment and Proteasome Degration", *Journal of Virology*, 75(4), (2001),1824-1833.

Duan, D., et al., "A New Dual-Vector Approach to Enhance Recombinant Adeno-Associated Virus-Mediated Gene Expression Through Intermolecular cis Activation", *Nature Medicine*, 6(5), (2000),595-598.

Duan, D., et al., "Chapter 15: Trans-Splicing Vectors Expand the Packaging Limits of Adeno-Associated Virus for Gene Therapy Applications", *Methods in Molecular Medicine*, vol. 76: *Viral Vectors for Gene Therapy: Methods and Protocols*, (2003),287-307.

Duan, D., et al., "Chapter 3—Adeno-Associated Virus", *In: Lung Biology in Health and Disease*, vol. 169—*Gene Therapy in Lung Diseases*, Albelda, S. M., Editor, Marcel Dekker, Inc.,(2002),51-92.

Duan, D., et al., "Chapter 3—Dual Vector Expansion of the Recombinant AAV Packing Capacity", *In: Methods in Molecular Biology*, vol. 219: *Cardiac Cell and Gene Transfer*, Metzger, J. M., Editor, Human Press, Inc., Totowa, NJ,(2003),29-51.

Duan, Dongsheng, et al., "Circular intermediates of recombinant adeno-associated virus have regional defined structural characteristics responsible for long-term episomal persistance in muscle tissue", *Journal of Virology*, 72(11), (Nov. 1998), 8568-77.

Duan, D., et al., "Consequences of DNA-Dependent Protein Kinase Catalytic Subunit Deficiency on Recombinant Adeno-Associated Virus Genome Circularization and Heterodimerization in Muscle Tissue", *Journal of Virology*, 77(8), (2003),4751-4759.

Duan, Dongsheng, et al., "Dynamin is required for recombinant adeno-associated virus type 2 infection", *Journal of Virology*, 73(12), (Dec. 1999),10371-10376.

Duan, D., et al., "Endosomal processing limits gene transfer to polarized airway epithelia by adeno-associated virus", *Journal of Clinical Investigation, 105*, (Jun. 2000),1573-1587.

Duan, D., et al., "Enhancement of Muscle Gene Delivery With Pseudotyped Adeno-Associated Virus Type 5 Correlates With Myoblast Differentiation", *Journal of Virology*, 75(16), (2001),7662-7671.

Duan, D., et al., "Expanding AAV Packaging Capacity With Transsplicing or Overlapping Vectors: A Quantitative Comparison", *Molecular Therapy*, 4(4), (2001),383-391.

Duan, D., "Formation of Adeno-Associated Virus Circular Genomes is Differentially Regulated by Adenovirus E4 ORF6 and E2a Gene Expression", *Journal of Virology*, 73(1), (Jan. 1999),161-169.

(56) References Cited

OTHER PUBLICATIONS

Duan, D., "Polarity Influences the Efficiency of Recombinant Adenoassociated Virus Irifection in Differentiated Airway Epithelia", *Human Gene Therapy, 9*, (Dec. 10, 1998),pp. 2761-2776.

Duan, D, et al., "Response to "Polarity Influences the Efficiency of Recombinant Adenoassociated Virus Infection in Differentiated Airway Epithelia"", *Human Gene Therapy, 10*, (1999),pp. 1553-1557.

Duan, Dongsheng, et al., "Structural Analysis of adeno-associated virus transduction circular intermediates", *Virology*, 261(1), (Aug. 1999),8-14.

Duan, Dongsheng, et al., "Structural and functional heterogeneity of intregrated recombinant AAV genomes", *Virus Research*, 48 (1), (Jan. 1997),pp. 41-56.

Ecelbarger, C. A., et al., "Regulation of the Abundance of Renal Sodium Transporters and Channels by Vasopressin", *Experimental Neurology, 171*, (2001), 227-234.

Elliott, P J., et al., "Recent Advances in Understanding Proteasome Function", *Current Opinion in Drug Discovery and Development*, 5 (2), ISSN: 1367-6733,(1999),484-490.

Engelhardt, J., et al., "Adeno-Associated Virus Vectors", U.S. Appl. No. 60/086,166, filed May 20, 1998.

Engelhardt, John, et al., "Adeno-Associated Virus Vectors", U.S. Appl. No. 09/276,625, (Mar. 25, 1999),120 pages.

Engelhardt, John, et al., "Compounds and Methods to Enhance Adeno-Associated Virus Transduction", U.S. Appl. No. 60/138,188, filed Jun. 8, 1999.

Engelhardt, John, et al., "Compounds and Methods to Enhance Adeno-Associated Virus Transduction", U.S. Appl. No. 60/201,089, filed May 2, 2000.

Engelhardt, J. F., et al., "Direct Gene Transfer of Human CFTR Into Human Bronchial Epithelia of Xenografts With E1-Deleted Adenoviruses", *Nature Genetics, 4*, (1993),27-34.

Engelhardt, John, et al., "Enhancement of Muscle Gene Delivery with Pseudotyped AAV-5 Correlates With Myoblast Differentiation", U.S. Appl. No. 60/305,204, filed Jul. 13, 2001.

Engelhardt, J. F., "The Lung as a Metabolic Factory for Gene Therapy", *The Journal of Clinical Invesriation*, 110(4), (2002),429-432.

Englehardt, John, et al., "Adeno-Associated Virus Vectors", U.S. Appl. No. 10/054,665,(Jan. 22, 2002),141 pages.

Englehardt, John, et al., "Adeno-Associated Virus Vectors and Uses Thereof", U.S. Appl. No. 09/684,554, (Oct. 6, 2000),141 pages.

Englehardt, John, "Compounds and Methods for Pharmico-gene Therapy of Epithelial Sodium Channel Associated Disorders", U.S. Appl. No. 60/512,347, filed Oct. 16, 2003.

Englehardt, John, et al., "Compounds and Methods to Enhance rAAV Transduction", U.S. Appl. No. 60/459,323, filed Mar. 31, 2003.

Englehardt, John, et al., "Pseudotyped Adeno-Associated Viruses and Uses Thereof", U.S. Appl. No. 10/194,421 filed, Jul. 12, 2002.

Everett, R D., et al., "A viral activator of gene expression functions via the ubiquitin-proteasome pathway", *The EMBO Journal*, 17 (24), (1998),pp. 7161-7169.

Fallin, R. A., et al., "PMA-Induced Inhibition of Amiloride-Sensitive Sodium Absorptiion is Partially Mediated by ERK1/2 Activation", *The FASEB Journal*, 17(5)(Abstracts Part II), Abstract No. 585-519,(2003),A915.

Fasbender, AL, et al., "Complexes of adenovirus with polycationic polymers and cationic lipids increase the efficiency of gene transfer in vitro and in vivo", *The Journal of Biological Chemistry*, 272 (10), (Mar. 7, 1997),6479-6489.

Fayadat, Laurence, et al., "Degradation of Human Thyroperoxidase in the Endoplasmic Reticulum Involves Two Different Pathways Depending on the Folding State of the Protein", *Journal of Biological Chemistry*, 275(21), (May 26, 2000)15948-15954.

Fenteany, G, et al., "Inhibition of Proteasome Activities and Subunit-Specific Amino-Terminal Threonine Modification by Lactacystin", *Science*, 268, (1995),pp. 726-731.

Fenteany, Gabriel, et al., "Lactacystin, Proteasome Function, and Cell Fate", *Journal of Biological Chemistry*, 273(15), (Apr. 10, 1998),8545-8548.

Ferrari, F K., et al., "Second-Strand Synthesis Is a Rate-Limiting Step for Efficient Transduction by Recombinant Adeno-Associated Virus Vectors", *Journal of Virology*, 70(5), (1996),3227-3234.

Figueiredo-Pereira, Maria E., et al., "The antitumor drug aciacinomycin A, which inhibits the degradation of ubiquitinated proteins, shows selectivity for the chymotrypsin-like activity of the bovine pituitary 20 S proteasome", *Journal of Biological Chemistry*, 271(28), (Jul. 12, 1996), 16455-16459.

Fisher, K J., et al., "Transduction with recombinant adeno-associated virus for the gene therapy is limited by leading-strand synthesis", *Journal of Virology*, 70(1), (Jan. 1996),520-532.

Flotte, T. R., et al., "Adeno-Associated Virus Vector Gene Expression Occurs in Nondividing Cells in the Absence of Vector DNA Integration", *American Journal of Respiratory Cell and Molecular Biology, 11*, (1994),pp. 517-521.

Flotte, T. R., et al., "Chapter 40—Adeno-Associated Viral Vectors for CF Gene Therapy", *In: Methods in Molecular Medicine, 70*, (2002),599-608.

Gabizon, Alberto, "Long-circulating liposomes for drug delivery in cancer therapy: a review of biodistribution studies in tumor-bearing animals", *Advanced Drug Delivery Reviews*, (1997),337-344.

Gabizon, Alberto, et al., "Preclinical Studies with Doxorubicin Encapsulated in Polyethyleneglycol-Coated Liposomes", *Journal of Liposome Research*, 3(3), (1993),517-528.

Gadallah, M. F., et al., "Epithelial Sodium Channel-Dependent Hyptertension: An Emerging Syndrome", *Journal of the American Society of Nephrology, 10 (Abstract Issue)*, Abstract No. A1842,(1999),365A.

Gadallah, M. F., et al., "Preservation of Renal Function in Patients with Hypertension and Chronic Renal Impairment; Revisted", *Journal of the American Society of Nephrology, 10 (Abstracts Issue)*, Abstract No. A1841,(1999),365A.

Garber, Ken, "Taking Garbage In, Taking Cancer Out?", *Science*, vol. 295, (Jan. 25, 2002),612-613.

Goldberg, A L., "New insights into proteasome function: from archaebacteria to drug development", *Chemistry & Biology*, 2 (8), (1995),pp. 503-508.

Gormley, K., et al., "Regulation of the Epithelial Sodium Channel by Accessory Proteins", *Biochem. J. 371*, (2003),1-14.

Gottlieb, T A., et al., "Actin Microfilaments Play a Critical Role in Endocytosis at the Apical but not the Basolateral Surface of Polarized Epithelial Cells", *The Journal of Cell Biology*, 120(3), (1993),pp. 695-710.

Halbert, C. L., "Transduction by Adeno-Associated Virus Vectors in the Rabbit Airway: Efficiency, Persistence, and Readministration", *Journal of Virology*, 71 (8), (Aug. 1997),pp. 5932-5941.

Hansen, J., et al., "Adeno-Associated Virus Type 2-Mediated Gene Transfer: Altered Endocytic Processing Enhances Transduction Efficiency in Murine Fibroblasts", *Journal of Virology*, 75(9), (2001),4080-4090.

Hansen, J., et al., "Impaired Intracellular Trafficking of Adeno-Associated Virus Type 2 Vectors Limits Efficient Transduction of Murine Fibroblasts", *Journal of Virology*, 74(2), (2000),992-996.

Hasegawa, S., et al., "Microtubule involvement in the intracellular dynamics for gene transfection mediated by cationic liposomes", *Gene Therapy*, vol. 8, (2001),1669-1673.

Hong, J., et al., "Identification of SRI6975, A compound that Enhances Adenovirus-Mediated Gene Expression in Polarized Epithelial Cells", *Cystic Fibrosis Foundation: 2000 North American CF Conference*, (Nov. 2000),1-2.

Hsu, A., et al., "Ritonavir. Clinical pharmacokinetics and interactions with other anti-HIV agents", *Clin Pharmacokinet*, 35(6), abstract,(Dec. 1998),1 page.

Huang, L., et al., "Efficient lipofection with cisplatin-resistant human tumor cells", *Cancer Gene Therapy*, vol. 3 No. 2 (1996),107-112.

Hummler, E., et al., "Genetic Disorders of Membrane Transport—V. The Epithelial Sodium Channel and its Implication in Human Diseases", *American Journal of Physiology, Gastrointensinal and Liver Physiology, 276*, (1999),G567-G571.

Iqbal, Mohamed, et al., "Potent Inhibitors of Proteasome", *Journal of Medicinal Chemistry*, vol. 38, No. 13, (1995),2276-2277.

(56) References Cited

OTHER PUBLICATIONS

Itani, O. A., et al., "Cycloheximide Increases Glucocorticoid-Stimulated alpha-ENaC mRNA in Collecting Duct Cells by p38 MAPK-dependent Pathway", *Am. J. Physiol. Renal Physiol., 284*, (2002),F778-F787.

Jensen, T J., et al., "Multiple Proteolytic Systems, Including the Proteasome, Contribute to CFTR Processing", *Cell, 83*, (1995),pp. 129-135.

Jiang, Q., et al., "Cellular Heterogeneity of CFTR Expression and Function in the Lung: Implications for Gene Therapy of Cystic Fibrosis", *European Journal of Human Genetics, 6*, (Jan. 1998),12-31.

Jorgensen, M. J., "Expression of the Completely y-Carboxylated Recombinant Human Prothrombin", *The Journal of Biological Chemistry*, 262(14), (1987),6729-6734.

Kamynina, E., et al., "Concerted Action of ENaC, Nedd4-2, and Sgk1 in Transepithelial Na+ Transport", *Am. J. Physiol. Renal Physiol., 283*, (2002),F377-F387.

Kaplan, Johanne M., et al., "Potentiation of gene transfer to the mouse lung by complexes of adenvirus vector and polycations improves therapeutic potential", *Human Gene Therapy*, vol. 9, No. 10, XP000972242, (Jul. 1, 1998),1469-1479.

Kazi, A., et al., "Inhibition of the Proteasome Activity, a Novel Mechanism Associated with the Tumor Cell Apoptosis-Inducing Ability of Genistein", *Biochemical Pharmacology, 66*, (2003),965-976.

Kessler, P., et al., "Sodium Butyrate Greatly Enhances the efficiency of Viral Transduction in Adult Ventricular Cardiomyocytes by Adeno-associated Viral Vectors", *Circulation* 92(8), (Oct. 15, 1995),296.

Kim, Kyung BO, et al., "Proteasome Inhibition by the Natural Products Epoxomicin and Dihydroeponemycin: Insights into Specificity and Potency", *Bioorganic & Medicinal Chemist Letters*, (1999),3335-3340.

Kiyomiya, Ken-Ichi, et al., "The Role of the Proteasome in apoptosis induced by anthracycline anticancer agents", *International Journal of Oncology*, 20 (6), ISSN: 1019-6439, (Jun. 2002),1205-1209.

Kloetzel, P M., "The Proteasome system: a neglected tool for improvement of novel therapeutic strategies?", *Gene Therapy, 5*, (1998),pp. 1297-1298.

Lebkowski, J., "Adeno-Associated Virus: a Vector System for Efficient Introduction and Integration of DNA into a Variety of Mammalian Cell Types", *Molecular and Cellular Biology*, 8 (10), (Oct. 1988),3988-3996.

Lee, Sang Goo, et al., "Enhancement of adenoviral transduction with polycationic liposomes in vivo", *Cancer Gene Therapy*, vol. 7, No. 10, (2000),1329-1335.

Lee, D. H., "Proteasome Inhibitors: Valuable New Tools for Cell Biologists", *Trends in Cell Biology,8*, (Oct. 1998),pp. 397-403.

Lee, Do Hee, et al., "Selective Inhibitors of the Proteasome-dependent and Vacuolar Pathways of Protein Degradation in Saccharomyces cerevisiae", *Journal of Biological Chemistry*, (Nov. 1, 1996),27280-27284.

Lee, Do Hee, et al., "The Proteasome Inhibitors and Their Uses", *Proteasomes: The World of Regulatory Proteolysis*, (2000),154-175.

Liang, E., et al., "Oligonucleotide delivery: a cellular prospective", *Pharmazie*, vol. 54, No. 8, XP000965598, (Aug. 1999),559-566.

Lu, Wei, et al., "HIV protease inhibitors restore impaired T-cell proliferative response in vivo and in vitro: a viral-suppression-independent mechanism", *Blood*, vol. 96, No. 1, (Jul. 1, 2000),250-258.

Luo, Hongyu, et al., "A Proteasome Inhibitor Effectively Prevents Mouse Heart Allograft Rejection", *Transplantation*, vol. 72, No. 2, (Jul. 27, 2001),196-202.

Mah, C, et al., "Adeno-Associated Virus Type 2-Mediated Gene Transfer: Role of Epidermal Growth Factor Receptor Protein Tyrosine Kinase in Transgene Expression", *Journal of Virology*, 72 (12), (1998),pp. 9835-9843.

Maitra, R., et al., "Increased Functional Cell Surface Expression of CFTR and deltaF508-CFTR by the Anthracycline doxorubicin", *Am. J. Physiol. Cell Physiol., 280*, (May 2001),C1031-C1037

Malik, B., et al., "ENaC Degradation in A6 Cells by the Ubiquitin-Proteosome Proteolytic Pathway", *The Journal of Biological Chemistry*, 276(16), (Apr. 20, 2001),12903-12910.

Mastroianni, Claudio M., et al., "Ex Vivo and In Vitro Effect of Human Immunodeficiency Virus Protease Inhibitors on Neutrophil Apoptosis", *Journal of Infectious Diseases* (182), (Nov. 2000),1536-1539.

Matalon, S., et al., "Lung Edema Clearance: 20 Years of Progress—Invited Review: Biophysical Properties of Sodium Channels in Lung Alveolar Epithelial Cells", *J. Appl. Physiol., 93*, (2002),1852-1859.

McAuliffe, O., et al., "Lantibiotics: Structure, Biosynthesis and Mode of Action", *FEMS Microbiology Reviews*, 25(3), (2001),285-308.

Meng, Lihao, et al., "Eponemycin Exerts Its Antitumor Effect through the Inhibition of Proteasome Function", *Cancer Research*, vol. 59, (Jun. 15, 1999),2798-2801.

Meng, L., et al., "Epoxomicin, a potent and selective proteasome inhibitor, exhibits in vivo antiinflammatory activity", *Proceedings of the National Academy of Sciences of USA*, 96 (18), (Aug. 31, 1999),10403-10408.

Meyer, Stephanie, et al., "Cyclosporine A is an uncompetitive inhibitor of proteasome activity and prevents NF-kB activation", *Federation of European Biochemical Societies*, (1997),354-358.

Mirshahi, M., et al., "Paradoxical Effects of Mineralocorticoids on the Ion Gated Sodium Channel in Embryologically Diverse Cells", *Biochemical and Biophysical Research Communications, 270*, (2000),811-815.

Mosnaim, Aron, et al., "Degradation Kinetics of Leucine5-Enkephalin by Plasma Samples from Healthy Controls and Various Patient Populations: In Vitro Drug Effects", *American Journal of Therapeutics*, vol. 7, (2000),185-194.

Nakayama, M., et al., "Hypomethylation Status of CpG Sites at the Promoter Region and Overexpression of the Human MDR1 Gene in Acute Myeloid Leukemias", *Blood*, 92(11), (1998),4296-4307.

Nam, Sangkil, et al., "Tannic Acid Potently Inhibits Tumor Cell Proteasome Activity, Increases p27 and Bax Expression, and Induces G1 Arrest and Apoptosis", *Cancer Epidemiology, Biomarkers & Prevention*, vol. 10, (Oct. 2001),1083-1088.

Nepka, Charitini, et al., "Chemopreventive activity of very low dose dietary tannic acid administration in hepatoma bearing C3H male mice", *Cancer Letters*, vol. 141, (1999),57-62.

Nepka, CH., et al., "Tannins, xenobiotic metabolism and cancer chemo-prevention in experimental animals", *European Journal of Drug Metabolism and Pharmacokinetics*, vol. 24, No. 2, (1999),183-189.

Nielsen, J., et al., "Spironolactone-Mediated Downregulation of the Epithelial Sodium Channel (eNaC) in Rat Kidney", *FASEB Journal*, 15(1) (*Abstracts Part 1*), Abstract No. 393.11,(2001),A432.

Obin, M, et al., "Neurite outgrowth in PC12 cells. Distinguishing the roles of ubiquitylation and ubiquitin-dependent proteolysis" *Journal of Biological Chemistry*, 274 (17), (Apr. 23, 1999),11789-11795.

Palombella, Vito, et al., "Role of the proteasome and NF-kB in streptococcal cell wall-induced polyarthritis", *Proc. National Academy of Science USA*, vol. 95 (Dec. 1998),15671-15676.

Parker, J. S., et al., "Cellular Uptake and Infection by Canine Parvovirus Involves Rapid Dynamin-Regulated Clathrin-Mediated Endocytosis, Followed by Slower Intracellular Trafficking", *Journal of Virology*, 74(4), (2000),1919-1930.

Petrov, Victor, et al., "Effect of Protease Inhibitors on Angiotensin-Converting Enzyme Activity in Human T-Lymphocytes", *American Journal of Hypertension*, vol. 13, No. 5, (May 2000),535-539.

Pickles, R J., et al., "Limited Entry of Adenovirus Vectors into Well-Differentiated Airway Epithelium Is Responsible for Inefficient Gene Transfer", *Journal of Virology*, 72 (7), (1998),pp. 6014-6023.

Prydz, K, et al., "Effects of Brefeldin A on Endocytosis, and Transport to the Golgi Complex in Polarized MDCK Cells", *The Journal of Cell Biology*, 119 (2), (1992),pp. 259-272.

Qing, K., et al., "Adeno-Associated Virus Type 2-Mediated Gene Transfer: Correlation of Tyrosine Phosphorylation of the Cellular Single Stranded D Sequence-Binding Protein with Transgene Expression in Human Cells In Vitro and Murine Tissues In Vivo", *Journal of Virology*, 72 (2), (Feb. 1998),pp. 1593-1599.

(56) References Cited

OTHER PUBLICATIONS

Qing, K., "Role of tyrosine phosphorylation of a cellular protein in adeno-associated virus 2-mediated transgene expression", *PNAS, 94*, (Sep. 1997),pp. 10879-10884.

Rao, Sharmila, et al., "Lovastatin-mediated G1 arrest is through inhibition of the proteasome, independent of hydroxymethyl glutarly-CoA reductase", *Proc. National Academ of Science USA*, vol. 96, (Jul. 1999),7797-7802.

Rendahl, K. G., et al., "Regulation of Gene Expression in vivo Following Transduction by Two Seperate rAAv Vectors", *Nature Biotechnology, 16*, (1998),757-761.

Rock, K L., et al., "Inhibitors of the Proteasome Block the Degradation of Most Cell Proteins and the Generation of Peptides Presented on MHC Class I Molecules", *Cell, 78*, (1994),pp. 761-771.

Rotin, D., "Regulation of the Epithelial Sodium Channel (ENaC) by Accessory Proteins", *Current Opinion in Nephrology and Hypertension, 9*, (2000),529-534.

Rotin, D., et al., "Trafficking and Cell Surface Stability of ENaC", *Am. J. Physiol. Renal Physiol., 281*, (2001),F391-F399.

Russell, D W., et al., "DNA synthesis and topoisomerase inhibitors increase transduction by adeno-associated virus vectors", *PNAS, 92*, (1995),pp. 5719-5723.

Sanlioglu, S, et al., "Cellular redox state alters recombinant adeno-associated virus transduction through tyrosine phosphatase pathways", *Gene Therapy, 6*, (1999),pp. 1427-1437.

Sanlioglu, S., et al., "Endocytosis and Nuclear Traffickling of Adeno-Associated Virus Type 2 Are Controlled by Rac1 and Phosphatidylinositol-3 Kinase Activation", *Journal of Virology*, 74(19), (2000),9184-9196.

Sanlioglu, S., et al., "Lipopoolysaccharide Induces Rac1-Dependent Reactive Oxygen Species Formation and Coordinates Tumor Necrosis Factor-alpha Secretion Through IKK Regulation of NF-kB", *The Journal of Biological Chemistry*, 276(32), (2001),30188-30198.

Sanlioglu, S., et al., "Loss of ATM Function Enhances Recombinant Adeno-Associated Virus Transduction and Integration Through Pathways Similar to UV Irradiation", *Virology, 268*, (2000),68-78.

Sanlioglu, S., et al., "Rate Limiting Steps of AAV Transduction and Implications for Human Gene Therapy", *Current Gene Therapy, 1*, (2001),137-147.

Sanlioglu, S., et al., "Two Independent Molecular Pathways for Recombinant Adeno-Associated Virus Genome Conversion Occur After UV-C and E4orf6 Augmentation of Transduction", *Human Gene Therapy*, 10(4), (1999),591-602.

Sasaki, T., et al., "Inhibitory Effect of di- and Tripeptidyl Aldehydes on Calpains and Cathepsins", *Journal of Enzyme Inhibition*, 3(3), (1990),195-201.

Schwartz, O, et al., "Antiviral Activity of the Proteasome on Incoming Human Immunodeficiency Virus Type 1", *Journal of Virology*, 72 (5), (1998),pp. 3845-3850.

Schwartz, Donald, et al., "The neutral cysteine protease bleomycin hydrolase is essential for epidermal integrity and bleomycin resistance", *Proc. National Academy of Science USA*, vol. 96, (Apr. 1999),4680-4685.

Schwarz, Katrin, et al., "The Selective Proteasome Inhibitors Lactacystin and Epoxomicin can be used to either Up- or Down-Regulate Antigen Presentation at Nontoxic Doses", *Journal of Immunology*, (2000),6147-6157.

Shah, Shimul, et al., "26S Proteasome Inhibition Induces Apoptosis and Limits Growth of Human Pancreatic Cancer", *Journal of Cellular Biochemistry*, vol. 82, (2001),110-122.

Smith, H., et al., "Effect of a cancer cachectic factor on protein synthesis/degradation in murine C2C12 myoblasts: modulation by eicosapentaenoic acid", *Cancer Res.*, 59(21), abstract,(Nov. 1999),1 page.

Son, Kyonghee, et al., "Exposure of human ovarian carcinoma to cisplatin transiently sensitizes the tumor cells for liposome-mediated gene transfer", *Proc. National Academy of Science USA*, vol. 91, (Dec. 1994),12669-12672.

Son, K, et al., "Factos influencing the drig sensitization of human tumor cells for in situ lipofection", *Gene Therapy* (3), (1996),630-634.

Son, Kyonghee, et al., "Nitric oxide-mediated tumor cell killing of cisplatin-based interferon-y gene therapy in murine ovarian carcinoma", *Cancer Gene Therapy*, vol. 7, No. 10, (2000),1324-1328.

Spindler, B., et al., "Characterization of Early Aldosterone-induced RNAs identified in A6 Kidney Epithelia", *Pfluegers Archiv*, vol. 434, Springer Verlag, Berlin, DE XP001025924 ISSN: 0031-6768,(1997),323-331.

Staub, O., "Chapter 5 Regulation of ENaC by Interacting Proteins and by Ubiquitination", *Current Topics in Membranes, 47—Amiloride-Sensitive Sodium Channels—Physiology and Functional Diversity*, Edited by Dale J. Benos, Academic Press, Publisher,(1999),65-87.

Staub, O., "Regulation of Stability and Functional of the Epithelial Na+ Channel (ENaC) by Ubiquitination", *The EMBO Journal*, 16(21), (1997),6325-6336.

Stockand, J. D., et al., "Targeted Degradation of the Epithelial Na Channel (ENaC) in Response to PKC Activation of the MAPK 1/2 Cascade", *The FASEB Journal*, 17(5), Abstracts (Part II), (Abstract No. 585.7),(2003),A913.

Stokes, J. B., "Regulation of rENac mRNA by Dietary NaCl and Steroids: Organ, Tissue, and Steroid Heterogeneity", *American Journal of Physiology, Cell Phyiology, 274*, (1998),C1699-C1707.

Teodori, L., et al., "Reduction of 1-beta-D-arabinofuranosytcytosine and adriamycin cytotoxicity following cell cycle arrest by anguidine", *Cancer Res.*, 41(4), abstract,(Apr. 1981), 1 page.

Teramoto, S., et al., "Factors influencing adeno-assocaited virus-mediated gene transfer to human cystic fibrosis airway epithelial cells: comparison with adenovirus vectors", *Journal of Virology*, 72(11), (Nov. 1998),8904-8912.

Thomas, C. P., et al., "Genomic Organization of the 5' End of Human B-ENaC and Preliminary Characterization of its Promoter", *Am. J. Physiol. Renal Physiol. 282*, (2002),F898-F909.

Tweedale, Tony, "[Dioxin-l] Inhibits Estrogen-Induced Breast Cancer Cell Proliferation", *Reuters Health*, http//lists.essential.org/pipermail/dioxin-l/Week-of-Mon-2000103/000096.html,(Dec. 1999),1 page.

Vihinen-Ranta, M, et al., "Intracellular Route of Canine Parvovirus Entry", *Journal of Virology*, 72 (1), (1998),pp. 802-806.

Walters, R W., et al., "Basolateral localization of fiber receptors limits adenovirus infection from the apical surface of airway epithelia", *The Journal of Biological Chemistry*, 274(15), (Apr. 9, 1999),10219-10226.

Walters, R W., et al., "Incorporation of Adeno-Associated Virus in a Calcium Phosphate Coprecipitate Improves Gene Transfer to Airway Epithelia In Vitro and In Vivo", *Journal of Virology*, 74 (1), (2000),pp. 535-540.

Westfall, T. D., et al., "The Ecto-ATPase Inhibitor ARL 67156 Enhances Parasympathetic Neurotransmission in the Guinea-Pig Urinary Bladder", *European Journal of Pharmacology, 329*, (1997),169-173.

Wickham, T J., et al., "Adenovirus targeted to heparan-containing receptors increases its gene delivery efficiency to multiple cell types", *Nature Biotechnology, 14*, (1996),pp. 1570-1573.

Wickham, T J., et al., "Targeted Adenovirus Gene Transfer to Endothelial and Smooth Muscle Cells by Using Bispecific Antibodies", *Journal of Virology*, 70 (10), (1996),pp. 6831-6838.

Woessner, Richard, et al., "Comparison of Three Approaches to Doxorubicin Therapy: Free Doxorubicin, Liposomal Doxorubicin, and B-Glucuronidase-Activated Prodrug (HMR 1826)", *Anticancer Research*, (2000),2289-2296.

Wojcik, "Inhibition of the proteasome as a therapeutic approach", *Drug Discovery Today*, 4 (4), (Apr. 1999),pp. 188-189.

Wojcik, Cezary, et al., "Lovastatin and simvastatin are modulators of the proteasome", *International Journal of Biochemistry & Cell Biology*, (32), (2000),957-965.

Working, Peter, et al., "Pharmacological-Toxicological Expert Report (Sealth Liposomal Doxorubicin HCI)", *Human & Experimental Toxicology*, (1996),752-785.

(56) References Cited

OTHER PUBLICATIONS

Xiao, W, et al., "Adeno-Associated Virus as a Vector for Liver-Directed Gene Threapy", *Journal of Virology*, 72 (12), (1998),pp. 10222-10226.

Yan, Z., et al., "[20] Recombinant AAV-Mediated Gene Delivery Using Dual Vector Heterodimerizatiion", *In: Methods in Enzmology*, vol. 346: *Gene Therapy Methods*, Phillips, M. I., Editor, Academic Press, San Diego, CA,(2002),334-357.

Yan, Z., et al., "Distinct Classes of Proteasome-Modulating Agents Cooperatively Augment Recombinant Adeno-Associated Virus Type 2 and Type 5-Mediated Transduction From the Apical Surfaces of Human Airway Epithelia", *Journal of Virology*, 78(6), (Mar. 2004), 2863-2874.

Yan, Z, et al., "Trans-splicing vectors expand the utility of adeno-associated virus for gene therapy", *PNAS, 97*, (Jun. 6, 2000), 6716-6721.

Zabner, J, et al., "Adenovirus-mediated gene transfer to ciliated airway epithelia requires prolonged incubation time", *Journal of Virology*, 70(10), (Oct. 1996),6994-7003.

Zabner, J, et al., "Adenovirus-mediated generation of cAMP-stimulated Cl-transport in cystic fibrosis airway epithelia in vitro: effect of promoter and administration method", *Gene Therapy, 3*, (1996),pp. 458-465.

Zentner, M. D., "The Amiloride-Sensitive Epithelial Sodium Channel a-Subunit is Transcriptionally Down-Regulated in Rat Parotid Cells by the Extracellular Signal-Regulated Protein Kinase Pathway", *The Journal of Biological Chemistry*, 273(46), (1998),30770-30776.

"U.S. Appl. No. 09/689,136 Advisory Action mailed Nov. 3, 2004", 3 pgs.

"U.S. Appl. No. 09/689,136, Amendment filed Aug. 3, 2005", 13 pgs.

"U.S. Appl. No. 09/689,136, Amendment filed Nov. 18, 2004", 11 pgs.

"U.S. Appl. No. 09/689,136 Final Office Action mailed Feb. 24, 2003", 11 pgs.

"U.S. Appl. No. 09/689,136 Final Office Action mailed Jun. 18, 2004", 8 pgs.

"U.S. Appl. No. 09/689,136 Non Final Office Action mailed Jan. 7, 2005", 10 pgs.

"U.S. Appl. No. 09/689,136 Non Final Office Action mailed Jun. 26, 2002", 13 pgs.

"U.S. Appl. No. 09/689,136 Non Final Office Action mailed Aug. 12, 2003", 8 pgs.

"U.S. Appl. No. 09/689,136 Notice of Allowance mailed Sep. 12, 2005", 10 pgs.

"U.S. Appl. No. 09/689,136 Preliminary Amendment filed Oct. 12, 2000", 2 pgs.

"U.S. Appl. No. 09/689,136, Response filed Jan. 12, 2004 to Non Final Office Action mailed Aug. 12, 2003", 12 pgs.

"U.S. Appl. No. 09/689,136, Response filed May 18, 2005 to Non Final Office Action mailed Jan. 7, 2005", 14 pgs.

"U.S. Appl. No. 09/689,136, Response filed May 30, 2003 to Final Office Action mailed Feb. 24, 2003", 13 pgs.

"U.S. Appl. No. 09/689,136, Response filed Oct. 18, 2004 to Final Office Action mailed Jun. 18, 2004", 13 pgs.

"U.S. Appl. No. 09/689,136, Response filed Nov. 26, 2002 to Non Final Office Action mailed Jun. 26, 2002", 14 pgs.

"U.S. Appl. No. 10/815,262 Non-Final Office Action mailed Oct. 30, 2007", 24 pgs.

"U.S. Appl. No. 10/815,262 Amendment filed Aug. 22, 2007", 1 pg.

"U.S. Appl. No. 10/815,262 Non Final Office Action mailed May 15, 2007", 25 pgs.

"U.S. Appl. No. 10/815,262 Response filed Aug. 14, 2007 to Non Final Office Action mailed May 15, 2007", 24 pgs.

"U.S. Appl. No. 10/815,557 Non Final Office Action mailed May 21, 2007", 24 pgs.

"U.S. Appl. No. 10/815,557 Response filed Aug. 21, 2007 to Non Final Office Action mailed May 21, 2007", 22 pgs.

"International Application Serial No. PCT/US 00/15700, International Search Report Dec. 21, 2000", 9 pgs.

"International Application Serial No. PCT/US 00/15700, Written Opinion Aug. 1, 2001", 7 pgs.

"Written Opinion for corresponding PCT Application No. PCT/US2004/009950",(Mar. 8, 2005),15 pgs.

"Written Opinion for corresponding PCT Application No. PCT/US2004/010045",(Jan. 10, 2005),15 pgs.

Audige, et al., *Clincial Sci., 104*, (2003),389-395.

Bohl, et al., *Blook* 92(5), (1998),1512-1517.

Bubien, et al., *J. Biol. Chem.* 276(11), (2001),8557-8566.

Duan, D, et al., "Circular Intermediates of Recombinant Adeno-Associated Virus Have Defined Structural Characteristics Responsible for Long-Term Episomal Persistence in Muscle Tissue", *Journal of Virology*, 72(11),(1998),8568-8577.

Goncalves, *Virology, Journal*, (2005),17 Pages.

Hunziker, et al., *Molecular Immunol, 38*, (2001),475-484.

Jiang, Q., et al., "Cellular Heterogenecity of CFTR Expression and Function in the Lung: Implications for Gene Therapy of Cystic Fibrosis", *European Journal of Human Genetics*, 6(1), (Jan. 1998),12-31.

Kapturczak, M. H., et al., "Adeno-Associated Virus (AAV) as a Vehicle for Therapeutic Gene Delivery : Improvements in vector Design and Viral Production Enhance Potential to prolong Graft Survival in Pancreatic Islet Cell Transplantation for the Reversal of Type I Diabetes", *Current Molecular Medicine*,(2001),245-258.

Kellenberger, et al., *Physiological Review, 82*, (2002),735-767.

Lechardeur, et al., *Curr. Gene Therapy, 2*, (2002),183-194.

Mah, C., et al., "Improved Method of Recombinant AAV2 Delivery for Systemic Targeted Gene Therapy", *Molecular Therapy*, 6(1), (2001),106-112.

Sakai, et al., *J. Physiol 519*, (1999),323-333.

Schaefer, et al., *FEBS Letters 471*, (2000),205-210.

Schwarzbach, M., et al., "Sensitization of Sarcoma cells to doxorubicin treatment by concomitant wild-type adeno-associated virus type 2(AAV-2) infection", *Oncology,20*, (2002),1211-1218.

Snyder, P. M., et al., "Serum and Glucocorticoid-Regulated Kinase Modulates Nedd4-2-Mediated Inhibition of the Epithelial NA+ Channel", *The Journal of Biological Chemistry*, 277(1), (2002),5-8.

Stutts, et al., *J. Biol. Chem.* 272(22), (1997),14037-14040.

Tenenbaum, et al., "Cellular contaminants of adeno-associated virus vector stocks can enhance transduction", *Gene Therapy, 6*, (1999),1045-1053.

Yalkinoglu, A. O., et al., "Inhibition of N-methyl-N'-nitro-N-nitrosoguanidine-induced methotrexate and adriamycin resistancce in CHO cells by adeno-associated virus type 2", *Cancer*,45(6), (1990),1195-1203.

Yan, Z., et al., "Distinct Classes of Proteasome-Modulating Agents Cooperatively Augment Recombinant Adeno-Associated Virus Type 2 and Type 5-Mediated Transduction from the Apical Surfaces of Human Airway Epithelia", *Journal of Virology, 78*, (Mar. 2004),2863-2874.

Zhang, F, et al., "Proteasome Function is Regulated by Cyclic AMP-dependent Protein Kinase through Phosphorylation of Rpt6", *The journal of Biological Chemistry*;282(31), (Aug. 3, 2007),22460-22471.

Buffinton, G. D., et al., "Oxidative stress in lungs of mice infected with influenza A virus", *Free Radic Res Commun.*, 16(2), (1992),99-110.

Cai, J., et al., "Inhibition of influenza infection by glutathione.", *Free Radical Biol Med.*, 34(7), (Apr. 1, 2003),928-36.

Dollard, S. C., et al., "Enhanced responsiveness to nuclear factor kappa B contributes to the unique phenotype of simian immunodeficiency virus variant SIVsmmPBj14.", *J Virol.*, 68(12), (Dec. 1994),7800-9.

Droge, W., et al., "HIV-induced cysteine deficiency and T-cell dysfunction—a rationale for treatment with N-acetylcysteine", *Immunol Today.*, 13(6), (Jun. 1992),211-4.

Graham, J. M., et al., "Iodixanol—a new density gradient medium for the dissection of the endosomal compartment", *Z Gastroenterol., 34 Suppl 3*, (1996),76-8.

Graham, J., "Purification of peroxisomes using a density barrier in a swinging-bucket rotor.", *ScientificWorldJournal, 2*, (May 22, 2002),1400-3.

(56) References Cited

OTHER PUBLICATIONS

Graham, J., et al., "The preparation of subcellular organelles from mouse liver in self-generated gradients of iodixanol", *Anal. Biochem.*, 220(2), (1994),367-73.

Kannan, R., et al., "Impairment of conjunctival glutathione secretion and ion transport by oxidative stress in an adenovirus type 5 ocular infection model of pigmented rabbits.", *Free Radic Biol Med.*, 37(2), (Jul. 15, 2004),229-38.

Kim, Koanhoi, "Proteasome Inhibitors Sensitize Human Vascular Smooth Muscle Cells to Fas (CD95)—Mediated Death", *Biochemical and Biophysical Research Communications*, vol. 281, No. 2, (2001),305-310

Lambeth, David J., "Nox enzymes and the biology of reactive oxygen", *Nature Reviews, Immunology* Mar. 2004, vol. 4, No. 3, Mar. 2004, pp. 181-189, XP002450232, (Mar. 2004),9.

Li, Q., et al., "Nox2 and Rac1 regulate H2O2-dependent recruitment of TRAF6 to endosomal interleukin-1 receptor complexes", *Mol Cell Biol.*, 26(1), (Jan. 2005),140-54.

Lin, H. C., et al., "Prediction of tyrosine sulfation sites in animal virus", *Biochemical and Biophysical Research Communications*,312(4),(Dec. 26, 2003),1154-1158.

Loguercio, C., et al., "Oxidative stress in viral and alcholic hepatitis.", *Free Radic Biol Med.*, 34(1), (Jan. 1, 2003),1-10.

McFadden, G., "Even viruses can learn to cope with stress.", *Science*, 279(5347), (Jan. 2, 1998),40-1.

Mihm, S., et al., "Inhibition of HIV-1 replication and NF-kappa B activity by cysteine and cysteine derivatives.", *AIDS*, 5(5), (May, 1991),497-503.

Mitsiades, Constantine, et al., "TRAIL/Apo2L ligand selectively induces apoptosis and overcomes drug resistance in multiple myeloma: theraputic applications", *Blood*, vol. 98, No. 3, (Aug. 1, 2001),795-804.

Nakamura, H., et al., "Redox imbalance and its control in HIV infection", *Antioxid Redox Signal.*, 4(3), (Jun. 2002),455-64.

Newman, G. W., et al., "Opposing regulatory effects of thioredoxin and eosinophil cytotoxicity-enhancing factor on the development of human immunodeficiency virus 1.", *J Exp Med.*, 180(1), (Jul. 1, 1994),359-63.

Oda, T., et al., "Oxygen radicals in influenza-induced pathogenesis and treatment with pyran polymer-conjugated SOD.",*Science*, 244(4907), (May 26, 1989),974-6.

Plonne, D., et al., "Separation of the intracellular secretory compartment of rat liver and isolated rat hepatocytes in a single step using self-generating gradients of iodixanol.", *Anal Biochem.*, 276(1), (Dec. 1, 1999),88-96.

Sanlioglu, et al., "Novel Approaches to Augment Adeno-Associated Virus Type-2 Endocytosis and Transduction", *Virus Research and Transduction*,104(1), (Aug. 2004),51-59.

Schreck, R., et al., "Antioxidants selectively supress activation of NF-kappa B by human T-cell leukemia virus type I Tax protein", *J Virol.*, 66(11), (Nov. 1992),6288-93.

Schwarz, K., "Oxidative stress during viral infection: a review.",*Free Radic Biol Med.*, 21(5), (1996),641-9.

Shisler, J. L., et al., "Ultraviolet-induced cell death blocked by a selenoprotein from a human dermatotropic poxvirus", *Science*,279(5347), (Jan. 2, 1998),102-5.

Sonntag, Florian, et al., "Adeno-associated Virus Type 2 Capsid with Externalized VP1/VP2 Trafficking Domains Are Generated Prior to Passage through the Cytoplasm and Are Maintained until Uncoating Occurs", *Journal of Virology*, vol. 80, No. 22,(Nov. 2006),11040-11054.

Teoh, M. L., et al., "Tumorigenic poxviruses up-regulate intracellular superoxide to inhibit apoptosis and promote cell proliferation", *J Virol.*, 79(9), (May 2005),5799-811.

Thrasher, A J., et al., "Generation of recombinant adeno-associated virus (rAAV) from an adenoviral vector and functional reconstitution of the NADPH-oxidase", *Gene Therapy, Macmillan Press Ltd.*, Basinstoke, GB, vol. 2, 1995, pp. 481-485, XP000651495, (1995),5.

Trischler, M., et al., "Biochemical analysis of distinct Rab5- and Rab11-positive endosomes along the transferrin pathway.", *J Cell Sci.*, 112 ( Pt 24), (Dec. 1999),4773-4783.

Voinea, et al., "Designing of Intelligent liposomes for efficient delivery of drugs", *J. cell. Mol. Med.* 6(4), (2002),465-474.

Xia, W., et al., "Presenilin 1 regulates the processing of beta-amyloid precursor protein C-terminal fragments and the generation of amyloid beta-protein in endoplasmic reticulum and Golgi", *Biochemistry*, 37(47), (Nov. 24, 1998),16465-71.

Bartoli, M., et al., "Mannosidase I inhibition rescues the human alpha-sarcoglycan R77C recurrent mutation.", *Hum Mol Genet.*, 17(9), (May 1, 2008), 1214-21.

Denby, L., et al., "Adeno-associated virus (AAV)-7 and -8 poorly transduce vascular endothelial cells and are sensitive to proteasomal degradation.", *Gene Ther.*. 12(20), (Oct. 2005), 1534-8.

Djaldetti, M., et al., "SEM observations on the effect of anthracycline drugs on cultured newborn rat cardiomyocytes (Abstract Only)", *Basic Red Cardiol.*, vol. 6, (1998), 672-7, abstract: 1 pg.

Gorvel, J. P, et al., "rab5 controls early endosome fusion in vitro.", *Cell*, 64(5), (Mar. 8, 1991), 915-25.

Gross, R., "Clinical problems of optimum bioavailability, in particular in cytostatic therapy (Abstract Only)", *Arzneimittelforschung*, vol. 26(1A), (1976), 130-5., abstract: 1 pg.

Gruenberg, J, et al., "Membrane traffic in endocytosis: insights from cell-free assays.", *Annu Rev Cell Biol.*, 5, (1989), 453-81.

Jennings, K., et al., "Proteasome inhibition enhances AAV-mediated transgene expression in human synoviocytes in vitro and in vivo.", *Mol Ther.*, 11(4), (Apr. 2005), 600-7.

Muzyczka, N., "Use of Adeno-Associated Virus as a General Transduction Vector for Mammalian Cells", *In: Current Topics in Microbiology and Immunology*, *158*, Springer-Verlag, Berlin: R.W. Compans, et al., (Eds.), (1992), 97-129.

Oberdorf, J., et al., "Redundancy of Mammalian Proteasome & Subunit Function during Endoplasmic Reticulum Associated Degration", *Biochemistry*; 40(44), (2001), 13397-13405.

Patel, et al., "Identification of Yeast DNA Topoisomerase II Mutants Resistant to the Antitumor Drug Doxorubcin: Implications for the Mechanisms of Doxorubicin Action and Cytotoxicity", *Pharmacol.* 52(4), (1997), 658-66.

Adams, J., et al., "Proteasome inhibition: a new strategy in cancer treatment.", *Invest New Drugs*, 18(2), (May 2000), 109-121

Wu, J., "On the role of proteasomes in cell biology and proteasome inhibition as a novel frontier in the development of immunosuppressants.", *Am J Transplant.*, 2(10), (Nov. 2002), 904-912.

Almond, J. B., et al., "The proteasome: a novel target for cancer chemotherapy", *Leukemia*, *16*, (2002), 443-443.

Johnson, J. S., et al., "Enhancement of Adeno-Associated Virus Infection by Mobilizing Capsids into and Out of the Nucleolus", *Journal of Virology*83(6), (2009), 2632-2644.

Kiyomiya, K-I, et al., "Proteasome is a Carrier to Translocate Doxorubin From Cytoplasm into Nucleus", *Life Sciences*, 62(20), (1998), 1853-1860.

Yan, Z., et al., "Ubiquitination of Both Adeno-Assocaiated Virus Type 2 and 5 Capsid Proteins Affects the Transduction Efficiency of Recombinant Vectors", *Journal of Virology*, 76(5), (2002), 2043-2053.

Finn, J. D, et al., "Proteasome inhibitors decrease AAV2 capsid derived peptide epitope presentation on MHC class I following transduction", *Mol Ther.*, 18(1), (Jan. 2010), 135-42.

"U.S. Appl. No. 11/890,761, Non Final Office Action mailed Jul. 12, 2011", 15 pgs.

Monahan, P E, et al., "Proteasome inhibitors enhance gene delivery by AAV virus vectors expressing large genomes in hemophilia mouse and dog models: a strategy for broad clinical application", Mol Ther 18, (2010), 1907-1916.

Sen, S, et al., "Characterisation of gene transfer to vascular cell lines using adenoassociated virus (AAV Serotype-2)", Endocrine Abstracts, 4 DP31; Dept. of medicine, National Univ. of Ireland, Galway, Ireland; 2The Ohio State Univ. School of Medicine and Molecular Virology, Columbus, Ohio, USA, (2002), 1 pg.

Zeitlin, Pamela L, "Novel pharmacologic therapies for cystic fibrosis", Perspective Series on cystic fibrosis 103(4), (Feb. 1999), 447-452.

(56) References Cited

OTHER PUBLICATIONS

Dou, Q. P, et al., "Proteasome inhibitors as potential novel anticancer agents", Drug Resist Updat., 2(4), (Aug. 1999), 215-223.

Ma, Y., et al., "p53-independent Down-Regulation of Mdm2 in Human Cancer Cells Treated with Adriamycin", Molecular Cell Biology Research Communications, 3(2), (Feb. 2000), 122-128.

Mikulski, S. M, et al., "Enhanced in vitro cytotoxicity and cytostasis of the combination of onconase with a proteasome inhibitor", Int J Oncol., 13(4), (Oct. 1998), 633-44.

Murray, R. Z, et al., "Proteasome inhibitors as anti-cancer agents", Anticancer Drugs, 11(6), (Jul. 2000), 407-17.

Ogiso, Y., at al., "Proteasome inhibition circumvents solid tumor resistance to topoisomerase II-directed drugs", Cancer Res., 60(9), (May 1, 2000), 2429-34.

Rivett, A. J, at al., "Proteasome inhibitors: from in vitro uses to clinical trials". Journal of Peptide Science, 6(9), (Sep. 2000), 478-488.

Douar, Anne-Marie, et al., "Intracellular Trafficking of Adeno-Associated Virus Vectors: Routing to the Late Endosomal Compartment and Proteasome", Journal of Virology, Feb. 2011, p. 1824-1833; vol. 75, No. 4, 1824-1833.

Finn, Jonathan D., et al., "Proteasome Inhibitors Decrease AAV2 Capsid-Derived Peptide Epitope Presentation on MHC Class I Following Transduction", Molecular Therapy vol. 18 No. 1, 135-142 jan. 2010, (Jan. 1, 2010), 135-142.

Hsy, PY, et al., "Effect of Polyethylenimine on Recombinant Adeno-Associated Virus Mediated Insulin Gene Therapy", 1. J Gene Med. Oct. 2005;7(10):1311-21—School of Pharmacy, College of Medicine, National Taiwan University, 1, Jen-Ai Road, Section 1, Taipei 100 Taiwan, (Oct. 7, 2005), 1311-21.

Nathwani, Amit C., et al., "Enhancing Transduction of the Liver by Adeno-Associated Viral Vectors", Gene Ther. Jan. 2009; 16(1): 60-69. doi:10.1038/gt.2008.137, (Jul. 1, 2009), 60-69.

\* cited by examiner

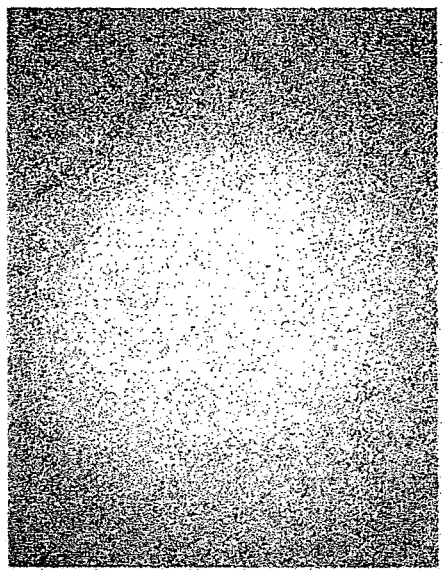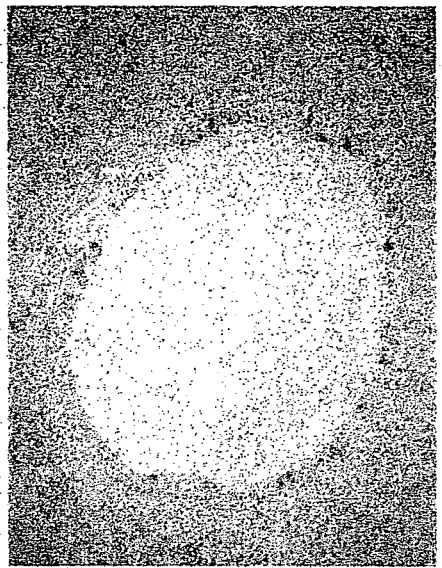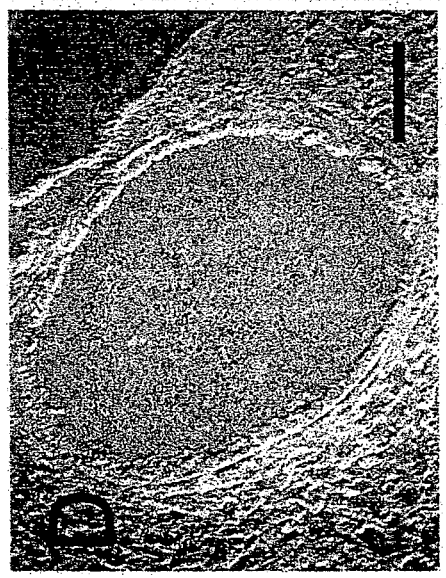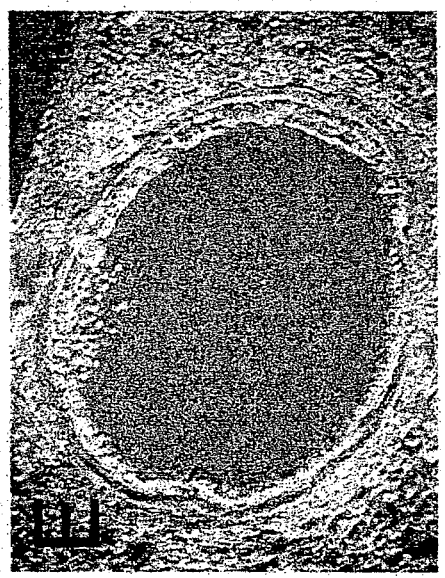
FIG. 17D
FIG. 17E

COMPOUNDS AND METHODS TO ENHANCE RAAV TRANSDUCTION

This application is a divisional of U.S. application Ser. No. 09/689,136, filed Oct. 12, 2000 (now U.S. Pat. No. 7,122,335), which is a continuation of International Patent Application No. PCT/US00/15700, filed Jun. 8, 2000 and published in English as WO 00/75365 A2 on Dec. 14, 2000, which claims the benefit of U.S. Provisional Application Ser. No. 60/138,188 filed Jun. 8, 1999, and Ser. No. 60/201,089, filed May 2, 2000; which applications and publication are incorporated by reference.

STATEMENT OF GOVERNMENT RIGHTS

This invention was made at least in part with a grant from the Government of the United States of America (Contract No. HL 58340 from the National Institutes of Health). The Government may have certain rights in the invention.

BACKGROUND OF THE INVENTION

Recombinant adeno-associated virus (rAAV) has several characteristics that underscore its potential as a gene therapy vector for numerous target organs and inherited diseases. rAAV vector systems potentially offer major advantages over adenovirus and retroviruses. These include the ability of rAAV to integrate into the genome of non-dividing cells, the lack of potential immune responses since all viral genes can be deleted, and the fact that rAAV can be concentrated to high titers.

Adeno-associated virus type-2 (AAV-2) has been suggested to be a very promising vector for the gene therapy of cystic fibrosis (Conrad et. al., 1996; Flotte et al., 1993; Halbert et al., 1997). In vivo administration of AAV vectors to the airway of rabbits and rhesus macaques has demonstrated long-term persistence, with viral DNA lasting up to 6 months (Conrad et al., 1996; Halbert et al., 1997). Despite the fact that this vector system has been claimed to have a very broad host tropism in a variety of human, simian, and rodent cell lines (Lebkowski et al., 1988; Muzyczka, 1992), the overall transduction efficiency in human airway epithelia seems to be quite low. In the absence of external stimuli, such as DNA damaging agents, topoisomerase inhibitor, or adenoviral early gene products (Alexander et al., 1997; Alexander et al., 1996; Ferrari et al., 1996; Fisher et al., 1996; Halbert et al., 1997; Russel et al., 1995), the in vitro transduction of primary cells and other non-dividing cells with rAAV is very inefficient. In contrast, rAAV transduction of actively dividing cells in S-phase is much more efficient (Russel et al., 1994). However, rAAV exhibits remarkable efficiency in the in situ transduction of skeletal muscle and CNS neurons, indicating that rAAV vectors can effectively transduce certain populations of non-dividing cells, and that cell-specific characteristics have profound effects on viral processing (Duan et al., 1998; Kaplitt et al., 1994; Xiao et al., 1996).

Two studies have suggested that single strand to double strand conversion of the viral genome may be the rate-limiting step for AAV-mediated gene transfer (Ferrari et al., 1996; Fisher et al., 1996). These studies demonstrated that adenovirus E4orf6 enhances the conversion of single-stranded DNA genomes to linear, double-stranded replication form dimers (Rfd) and monomers (Rfm), through a pathway characteristic of the lytic phase of rAAV replication. The structure of these replication forms consists of head-to-head and tail-to-tail orientated linear concatamers with one covalently linked end (Ferrari et al., 1996; Fisher et al., 1996). In contrast, recent studies have elucidated an alternative pathway for the conversion of rAAV genomes to double-stranded circular intermediates with head-to-tail monomer and concatamer structures (Duan et al., 1999; Duan et al., 1998; Sanlioglu et al., 1999). The distinct pathways leading to the formation of either circular AAV genomes or Rf intermediates appear to be regulated by different cellular factors. For example, adenoviral E4orf6 expression decreases circular genome formation while adenovirus E2a enhances its formation (Duan et al., 1999). Similarly, UV irradiation also enhances AAV circular intermediate formation but not Rf intermediates (Sanlioglu et al., 1999). Based on findings that circular AAV intermediates are associated with long-term episomal persistence and transgene expression in muscle (Duan et al., 1998), and UV irradiation increases both circular intermediates and the extent of integration, AAV circular intermediates may be latent phase preintegration structures.

The human airway is lined by specialized ciliated and non-ciliated epithelial cells, which not only provide protection from the external environment, but also perform functions involved in regulating the exchange of molecules between the airway lumen and underlying submucosa. These cellular functions are supported by a highly polarized organization with respect to the distribution of membrane proteins and subcellular organelles (Rodriguez-Boulan et al., 1993; Wills et al., 1996). Previous studies have suggested that this asymmetric spatial organization has significant influences on the efficiency of gene transfer. For example, the lack of integrins and adenoviral fiber receptor on the apical surface may explain the inefficient infection of differentiated, ciliated airway epithelia with this viral system (Goldman eta al., 1995; Zabner et al., 1997). Recent studies on polarized airway epithelial cells have also revealed a similar sidedness to retroviral infectivity, which may in part be explained by the partitioning of retroviral receptors to the basolateral membrane (Wang et al., 1998). In addition, similar findings of polarity in rAAV infection of polarized airway epithelia have been reported (Duan et al., 1998). These studies demonstrate a 200-fold greater infectivity of rAAV from the basolateral sides of airway epithelia.

Polarized entry into epithelial cells is also a well-known phenomenon for a variety of other viruses. For example, vaccinia virus, vesicular stomatitis virus, cytomegalovirus, canine parvovirus (CPV), and Semliki forest virus transduce polarized epithelia predominantly through basolateral membranes (Basak et al., 1989; Fuller et al., 1984; Rodriguez et al., 1991; Tugizov et al; 1996). In contrast, simian virus 40 and measles virus preferentially infect via the apical membranes (Blau et al., 1995; Clayspri et al., 1988). It is generally believed that the asymmetric distribution of cellular membrane receptors is responsible for the polarity of infection exhibited by these viruses.

However, it is also plausible that other rate limiting steps may play a role in the overall efficiency of viral transduction. These steps include virus binding, endocytosis, endosome processing, nuclear transport, uncoating, gene conversion, transcription, and translation. In this regard, previous studies in polarized MDCK cells have demonstrated a slower maturation of coated pits from the apical surface, indicating a difference in the rate of endocytosis between the apical and basolateral membranes (Naim et al., 1995).

For AAV, two approaches have been used to enhance rate-limiting steps in viral vector transduction. These include manipulation of cell surface receptors (Qing et al., 1997) and/or receptor ligands in the virus coat proteins (Wickham et al., 1996a; Wickham et al., 1996b; Bartlett et al., 1999). Alternative approaches have attempted to increase transgene expression by enhancing the molecular conversion of non-functional viral genomes to expressible forms in the case of rAAV (Fisher et al., 1996; Sanlioglu et al., 1999) or by increasing transcription and translation efficiencies by altering the transgene expression cassettes (Zabner et al., 1996; Xiao et al., 1998).

Cystic fibrosis is the most common inherited disease in the Caucasian population, and it is likely that gene therapy for this disorder will target the lung airway epithelium. The development of AAV as a gene therapy vehicle for treating cystic fibrosis has several unique advantages based on its viral biology. For example, wild type AAV infections are known to occur in the respiratory epithelium but have no known associated pathology. However, as described above, fully differentiated airway epithelia are extremely resistant to infection from the apical surface not only with rAAV-2 but also all other types of viral vectors currently in use, viral vectors including, adenovirus, lentivirus, retrovirus, and AAV.

Therefore, what is needed is the identification of agents which can alter, e.g., increase or enhance, rAAV transduction in vivo. What is also needed is the identification of agents that increase or enhance the expression of a transgene in rAAV in non-dividing cells such as those in the liver and the airway.

SUMMARY OF THE INVENTION

The invention provides a method to identify an agent that alters adeno-associated virus transduction of a eukaryotic cell, e.g., a mammalian cell such as a mammalian lung or liver cell, or a population of eukaryotic cells. The method comprises contacting the cell or population of cells with an agent and virus. Then it is determined whether virus transduction is altered. Preferred cells include those of mammals, birds, fish, and reptiles, especially domesticated mammals and birds such as humans, non-human primates, cattle, sheep, pigs, horses, dogs, cats, mice, rats, rabbits, chickens, and turkeys. For example, polarized human airway epithelial cells grown at an air-liquid interface or human bronchial xenografts are useful to identify agents which alter viral transduction. Preferred agents are those which enhance virus transduction, e.g., by enhancing viral endocytosis, decreasing viral nucleic acid or protein degradation in endosomes, and/or enhancing viral transport to the nucleus. Thus, agents which enhance virus transduction are particularly useful in gene therapy which employs rAAV to introduce and/or express a therapeutic peptide or polypeptide.

As described hereinbelow, virus binding, e.g., the restricted distribution of viral receptors, and endocytosis of AAV-2 at the apical membrane of airway epithelia is not the major rate limiting step in transduction of this tissue type. In fact, differentiated human airway epithelia internalize rAAV-2 quite efficiently from the apical surface. Rather, endosomal processing and trafficking of internalized virus to the nucleus is the major obstacle encountered by AAV-2 following infection from the apical membrane of the airway. In contrast to basolateral infection which led to the efficient conversion of single stranded AAV DNA to circular form genomes, apical infection gave rise to persistent intracellular single stranded viral DNA in a transcriptionally inactive state for up to 50 days. Using proteasome inhibitors which increase the efficiency of endosomal processing of AAV-2 and intracellular routing to the nucleus, a significantly enhanced transduction from the apical surface of more than 200-fold was observed, to nearly that of transduction from the basolateral surface. It was also found that AAV capsid proteins are ubiquitinated following endocytosis, and that ubiquitin-mediated proteasome degradation of incoming virus can be blocked by treatment with either proteasome or ubiquitin ligase inhibitors.

Ubiquitination of the viral capsid thus appears to be a major barrier for altering the efficiency of trafficking the virus to the nucleus and/or nuclear processing events for conversion of the single strand DNA genome to a transcriptionally active state. Moreover, importantly, in vivo application of proteasome inhibitor in mouse lung augmented rAAV gene transfer from undetectable levels to a mean of 10.4+/−1.6% of the epithelial cells in large bronchioles. Thus, the use of proteasome inhibitors to circumvent the major endosomal processing barriers to transduction in the airway may provide clinically useful strategies for in vivo AAV-mediated gene therapy of respiratory disorders such as cystic fibrosis, as well as for other tissues in which viral processing appears to be a rate limiting event.

Preferred agents to enhance the transduction of cells, e.g., human cells, by rAAV include peptide cysteine protease inhibitors, e.g., LLnL. Therefore, the invention further provides a method in which a eukaryotic cell is contacted with virus and an agent comprising a compound of formula (I): $R_1$-A-(B)$_n$—C, wherein $R_1$ is an N-terminal amino acid blocking group; each A and B is independently an amino acid; C is an amino acid wherein the terminal carboxy group has been replaced by a formyl (CHO) group; and n is 0, 1, 2, or 3; or a pharmaceutically acceptable salt thereof.

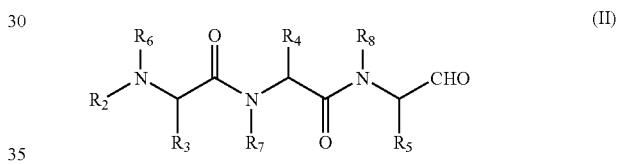

Another preferred agent of the invention is a compound of formula (II): wherein $R_2$ is an N-terminal amino acid blocking group;

$R_3$, $R_4$, and $R_5$ are each independently hydrogen, $(C_1$-$C_{10})$ alkyl, aryl or aryl($C_1$-$C_{10}$)alkyl; and $R_6$, $R_7$, and $R_8$ are each independently hydrogen, $(C_1$-$C_{10})$ alkyl, aryl or aryl($C_1$-$C_{10}$)alkyl; or a pharmaceutically acceptable salt thereof.

Other preferred agents useful in the methods of the invention include a compound of formula (III):

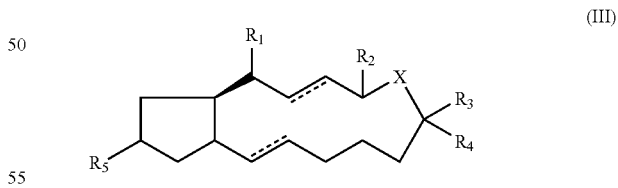

wherein, $R_1$ is H, halogen, $(C_1$-$C_{10})$alkyl, $(C_1$-$C_{10})$alkenyl, $(C_1$-$C_{10})$ alkynyl $(C_1$-$C_{10})$alkoxy, $(C_1$-$C_{10})$alkanoyl, (=O), (=S) OH, SR, CN, $NO_2$, trifluoromethyl or $(C_1$-$C_{10})$alkoxy, wherein any alkyl, alkenyl, alkynyl, alkoxy or alkanoyl may optionally be substituted with one or more halogen, OH, SH, CN, $NO_2$, trifluoromethyl, NRR or SR, wherein each R is independently H or $(C_1$-$C_{10})$alkyl;

$R_2$ is (=O) or (=S);

$R_3$ is H, $(C_1$-$C_{10})$alkyl, $(C_1$-$C_{10})$alkenyl, $(C_1$-$C_{10})$alkynyl, $(C_1$-$C_{10})$alkoxy or $(C_3$-$C_8)$cycloalkyl, wherein any alkyl, alkenyl, alkynyl, alkoxy or cycloalkyl may optionally be substituted with one or more halogen, OH, CN, $NO_2$, trifluoromethyl, SR, or NRR, wherein each R is independently H or $(C_1-C_{10})$alkyl;

$R_4$ is H, $(C_1-C_{10})$alkyl, $(C_1-C_{10})$alkenyl, $(C_1-C_{10})$alkynyl, $(C_1-C_{10})$alkoxy or $(C_3-C_8)$cycloalkyl, wherein any alkyl, alkenyl, alkynyl, alkoxy or cycloalkyl may optionally be substituted with one or more halogen, OH, CN, $NO_2$, trifluoromethyl, SR, or NRR, wherein each R is independently H or $(C_1-C_{10})$alkyl;

$R_5$ is H, halogen, $(C_1-C_{10})$alkyl, $(C_1-C_{10})$alkenyl, $(C_1-C_{10})$alkynyl, $(C_1-C_{10})$alkoxy, $(C_1-C_{10})$alkanoyl, (=O), (=S), OH, SR, CN, $NO_2$ or trifluoromethyl, wherein any alkyl, alkenyl, alkynyl, alkoxy or alkanoyl may optionally be substituted with one or more halogen, OH, SH, CN, $NO_2$, trifluoromethyl, NRR or SR, wherein each R is independently H or $(C_1-C_{10})$alkyl; and X is O, S or NR wherein R is H or $(C_1-C_{10})$alkyl, or a pharmaceutically acceptable salt thereof.

Preferably, $R_1$ is OH. It is also preferred that $R_2$ is (=O); $R_3$ is H or $(C_1-C_{10})$alkyl, and more preferably $R_3$ is methyl. Other preferred embodiments include $R_4$ is H or $(C_1-C_{10})$alkyl, and more preferably, $R_4$ is H; $R_5$ is halogen, CN, $NO_2$, trifluoromethyl or OH, and more preferably, $R_5$ is OH. A compound of formula (III) includes X is O or S, preferably O; wherein both—are a single bond, wherein one—is a double bond, or wherein both—are a double bond. In a more preferred embodiment, $R_1$ is OH, $R_2$ is (=O), $R_3$ is methyl, $R_4$ is H, $R_5$ is OH, X is O, and both—are a double bond.

Yet another preferred agent useful in the methods of the invention is a compound of formula (III):

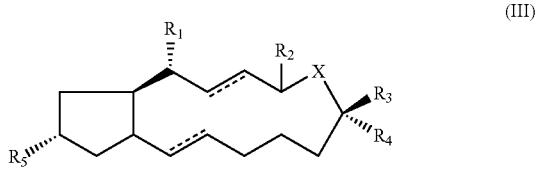

(III)

wherein $R_1$ is halogen, CN, $NO_2$, trifluoromethyl or OH. Preferably, $R_1$ is OH. It is also preferred that $R_2$ is (=O); $R_3$ is H or $(C_1-C_{10})$alkyl, and more preferably $R_3$ is methyl. Other preferred embodiments include $R_4$ is H or $(C_1-C_{10})$alkyl, and more preferably, $R_4$ is H; $R_5$ is halogen, CN, $NO_2$, trifluoromethyl or OH, and more preferably, $R_5$ is OH. A compound of formula (IV) includes X is O or S, preferably O; wherein both—are a single bond, wherein one—is a double bond, or wherein both—are a double bond. In a more preferred embodiment, $R_1$ is OH, $R_2$ is (=O), $R_3$ is methyl, $R_4$ is H, $R_5$ is OH, X is O, and both—are a double bond.

Another preferred agent useful in the methods of the invention includes an agent that inhibits the activation of ubiquitin, the transfer of ubiquitin to the ubiquitin carrier protein, ubiquitin ligase, or a combination thereof. Preferred ubiquitin ligase inhibitors include a compound of formula (IV): wherein R is hydrogen, an R-A-$A_1$-$R_1$ amino acid, or a peptide, wherein the N-terminus amino acid can optionally be protected at the amino group with acetyl, acyl, trifluoroacetyl, or benzyloxycarbonyl;

A is an amino acid or a direct bond;

$A_1$ is an amino acid; and $R_1$ is hydroxy or an amino acid, wherein the C-terminus amino acid can optionally be protected at the carboxy group with $(C_1-C_6)$alkyl, phenyl, benzyl ester or amide (e.g., C(=O)$NR_2$, wherein each R is independently hydrogen or $(C_1-C_6)$alkyl);

or a pharmaceutically acceptable salt thereof

A specific value for R is hydrogen.

A specific value for A is an amino acid. Another specific value for A is Ile, Leu or His. Another specific value for A is Leu or His.

A specific value for $A_1$ is Ala or Gly. Another specific value for $A_1$ is Ala.

A specific value for $R_1$ is hydroxy.

Specifically, the peptide can be a dipeptide (i.e., can comprise 2 amino acids).

Specifically, the peptide can be H-Leu-Ala-OH, H-His-Ala-OH, H-Leu-Gly-OH, H-His-Gly-OH, H-Ile-Ala-OH, or H-Ile-Gly-OH. More specifically, the peptide can be H-Leu-Ala-OH or H-His-Ala-OH.

Further, as described herein, the activity of agents that inhibit endosomal processing of virus may be enhanced by the addition of agents, such as EDTA or EGTA, which may alter molecules in pathways associated with endosomal processing, e.g., agents such as calcium chelators or modulators of intracellular calcium levels. Thus, the invention also provides for compositions or kits comprising: 1) an inhibitor of endosomal processing; and 2) an agent which enhances the activity of the inhibitor. The inhibitor, or combination thereof, may be employed in the methods of the invention, or may be employed with an agent that enhances the activity of the inhibitor(s).

Therefore, the invention also provides a method to alter adeno-associated virus transduction of a eukaryotic cell or population of cells. The method comprises contacting the cell with an amount of at least one agent of the invention and an amount of virus effective to alter virus transduction. The agent may be contacted with the cell concurrently with the virus, prior to contacting the cell with virus or after contacting the cell with virus. The agent(s) and/or virus may each be administered once, or in repeated dosing, so as to achieve the desired effect, i.e., to enhance rAAV transduction. Since adeno-associated virus has been shown to have a broad host range (for pulmonary expression) and persists in muscle, rAAV may be employed to express a gene in any animal, and particularly in mammals, birds, fish, and reptiles, especially domesticated mammals and birds such as cattle, sheep, pigs, horses, dogs, cats, chickens, and turkeys. Both human and veterinary uses are particularly preferred.

The gene being expressed can be either a DNA segment encoding a polypeptide, with whatever control elements (e.g., promoters, operators) are desired, or a non-coding DNA segment, the transcription of which produces all or part of some RNA-containing molecule (such as a transcription control element, +RNA, or anti-sense molecule).

Therapeutic or prophylactic therapies in which the vectors are useful include blood disorders (e.g., sickle cell anemia, thalassemias, hemophilias, and Fanconi anemias), neurological disorders, such as Alzheimer's disease and Parkinson's disease, and muscle disorders involving skeletal, cardiac or smooth muscle, as well as diseases of the lung, e.g., cystic fibrosis and asthma. In particular, therapeutic genes useful in the vectors of the invention include the β-globin gene, the γ-globin gene, Factor VIII gene, Factor IX gene, the cystic fibrosis transmembrane conductance receptor gene (CFTR), the Fanconi anemia complementation group, a gene encoding a ribozyme, an antisense gene, a low density lipoprotein (LDL) gene, a tyrosine hydroxylase gene (Parkinson's disease), a glucocerebrosidase gene (Gaucher's disease), an arylsulfatase a gene (metachromatic leukodystrophies) or genes encoding other polypeptides or proteins. Also within the scope of the invention is the inclusion of more than one open reading frame in a recombinant adeno-associated virus vector, i.e., a plurality of genes may be present in an individual vector. Further, as a circular intermediate may be a concatamer, each monomer of that concatamer may comprise a different gene.

Circularized intermediates of recombinant adeno-associated virus impart episomal persistence to linked sequences in Hela cells, fibroblasts and muscle cells. Thus, in vivo persistence of recombinant adeno-associated virus can occur through episomal circularized genomes which may represent preintegration intermediates with increased episomal stability. Thus, recombinant adeno-associated virus is preferably prepared from a vector comprising at least one first DNA segment, a biologically active fragment or variant thereof, of a circular intermediate of adeno-associated virus, which DNA segment confers increased episomal stability or persistence of the vector in a host cell; and a second DNA segment comprising a gene. Preferably, the second DNA segment encodes a therapeutically effective polypeptide.

DETAILED DESCRIPTION OF THE INVENTION

Definitions

Figure 1:
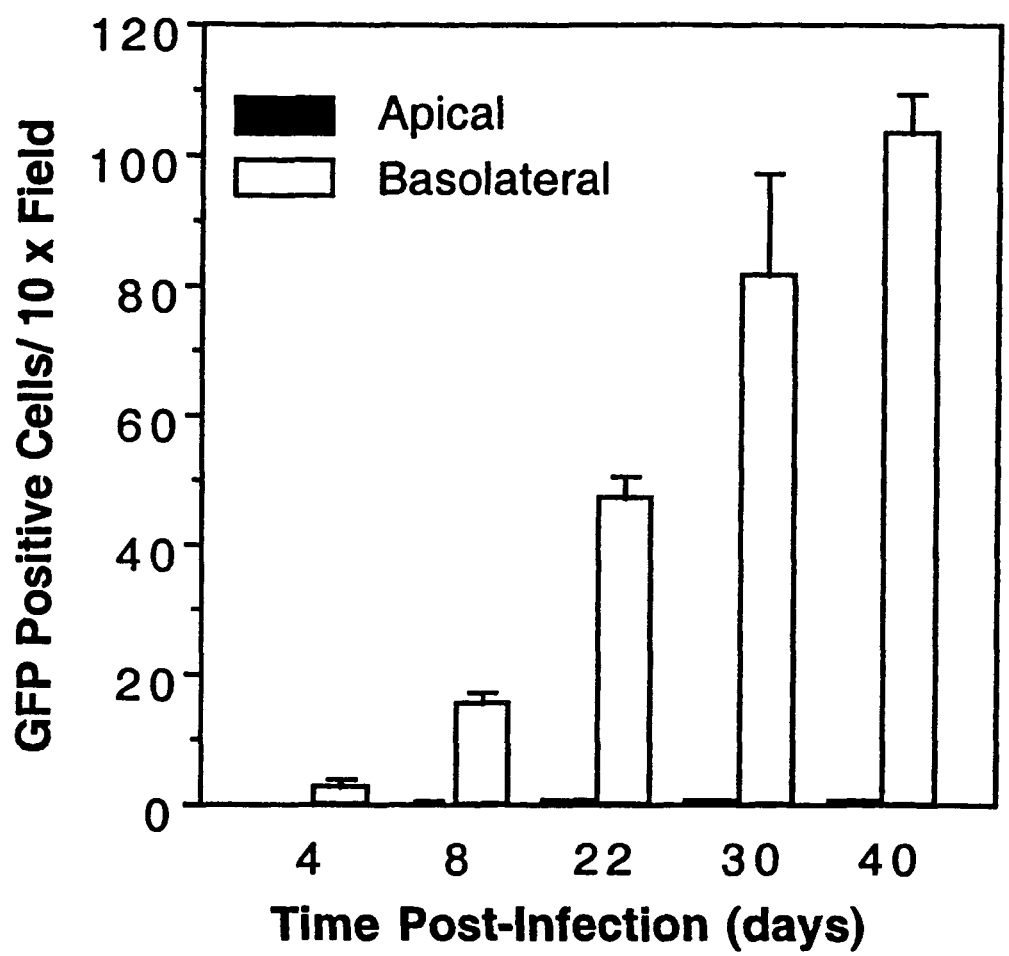
FIG. 1. Polarity and time course of rAAV transduction in differentiated bronchial epithelial cells. Polarized airway epithelia were infected via the apical or basolateral membranes with $5 \times 10^9$ particles of AV.GFP3ori virus (MOI=10,000 particles/cell) for 24 hours. The abundance of GFP transgene expressing cells was quantitated by indirect fluorescent microscopy at 4, 8, 22, 30, and 40 days. The bar graphs in Panel A represent the mean (+/−SEM) of 4 independent experiments for each condition.

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest) and/or a selectable or detectable marker.

"AAV" is adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector").

"Transduction" or "transducing" as used herein, are terms referring to a process for the introduction of an exogenous polynucleotide, e.g., a transgene in rAAV vector, into a host cell leading to expression of the polynucleotide, e.g., the transgene in the cell. The process includes 1) binding of the virus to the cell membrane, 2) endocytosis, 3) escape from endosomes and trafficking to the nucleus, 4) uncoating of the virus particles and synthesis of the second DNA strand to form expressible double-stranded forms, including circular intermediates, and 5) integration into the host genome, the alteration of any of which, or a combination thereof, e.g., by an agent of the invention, results in altered expression or persistence of the introduced polynucleotide in the host cell or a population of cells. Altered expression or persistence of a polynucleotide introduced via rAAV can be determined by methods well known to the art including, but not limited to, protein expression, and DNA and RNA hybridization. The agents of the invention preferably enhance or increase viral endocytosis, escape from endosomes and trafficking to nucleus, and/or uncoating of the viral particles in the nucleus, so as to alter expression of the introduced polynucleotide, e.g., a transgene in a rAAV vector, in vitro or in vivo. Methods used for the introduction of the exogenous polynucleotide include well-known techniques such as transfection, lipofection, viral infection, transformation, and electroporation, as well as non-viral gene delivery techniques. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

A "detectable marker gene" is a gene that allows cells carrying the gene to be specifically detected (e.g., distinguished from cells which do not carry the marker gene). A large variety of such marker genes are known in the art.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art, some of which are described below.

An "rAAV vector" as used herein refers to an AAV vector comprising a polynucleotide sequence not of AAV origin (i.e., a polynucleotide heterologous to AAV), typically a sequence of interest for the genetic transformation of a cell. In preferred vector constructs of this invention, the heterologous polynucleotide is flanked by at least one, preferably two AAV inverted terminal repeat sequences (ITRs). The term rAAV vector encompasses, both rAAV vector particles and rAAV vector plasmids.

An "AAV virus" or "AAV viral particle" refers to a viral particle composed of at least one AAV capsid protein (preferably by all of the capsid proteins of a wild-type AAV) and an encapsidated polynucleotide. If the particle comprises a heterologous polynucleotide (i.e., a polynucleotide other than a wild-type AAV genome such as a transgene to be delivered to a mammalian cell), it is typically referred to as "rAAV".

A "helper virus" for AAV refers to a virus that allows AAV (e.g., wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

An "infectious" virus or viral particle is one that comprises a polynucleotide component which it is capable of delivering into a cell for which the viral species is trophic. The term does not necessarily imply any replication capacity of the virus.

A "replication-competent" virus (e.g., a replication-competent AAV, sometimes abbreviated as "RCA") refers to a phenotypically wild-type virus that is infectious, and is also capable of being replicated in an infected cell (i.e., in the presence of a helper virus or helper virus functions). In the case of AAV, replication competence generally requires the presence of functional AAV packaging genes. Preferred rAAV vectors as described herein are replication-incompetent in mammalian cells (especially in human cells) by virtue of the lack of one or more AAV packaging genes. Preferably, such rAAV vectors lack any AAV packaging gene sequences in order to minimize the possibility that RCA are generated by recombination between AAV packaging genes and an incoming rAAV vector. Preferred rAAV vector preparations as described herein are those which contain few if any RCA (preferably less than about 1 RCA per $10^2$ rAAV particles, more preferably less than about 1 RCA per $10^4$ rAAV particles, still more preferably less than about 1 RCA per $10^8$ rAAV particles, even more preferably less than about 1 RCA per $10^{12}$ rAAV particles, most preferably no RCA).

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" or "TRS," as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a TRS or promoter that is removed from its native coding sequence and operably linked to a different coding sequence is a heterologous TRS or promoter.

A "replicon" refers to a polynucleotide comprising an origin or replication which allows for replication of the polynucleotide in an appropriate host cell. Examples of replicons include episomes (including plasmids), as well as chromosomes (such as the nuclear or mitochondrial chromosomes). "Stable integration" of a polynucleotide into a cell means that the polynucleotide has been integrated into a replicon that tends to be stably maintained in the cell. Although episomes such as plasmids can sometimes be maintained for many generations, genetic material carried episomally is generally more susceptible to loss than chromosomally integrated material. However, maintenance of a polynucleotide can often be effected by incorporating a selectable marker into or adjacent to a polynucleotide, and then maintaining cells carrying the polynucleotide under selective pressure. In some cases, sequences cannot be effectively maintained stably unless they have become integrated into a chromosome; and, therefore, selection for retention of a sequence comprising a selectable marker can result in the selection of cells in which the marker has become stably integrated into a chromosome. Antibiotic resistance genes can be conveniently employed in that regard, as is well known in the art. Typically, stably-integrated polynucleotides would be expected to be maintained on average for at least about twenty generations, preferably at least about one hundred generations, still more preferably they would be maintained permanently. The chromatin structure of eukaryotic chromosomes can influence the level of expression of an integrated polynucleotide. Having the genes carried on episomes can be particularly useful where it is desired to have multiple stably-maintained copies of a particular gene. The selection of stable cell lines having properties that are particularly desirable in the context of the present invention are described and illustrated below.

"Packaging" as used herein refers to a series of subcellular events that results in the assembly and encapsidation of a viral vector, particularly an AAV vector. Thus, when a suitable vector is introduced into a packaging cell line under appropriate conditions, it can be assembled into a viral particle. Functions associated with packaging of viral vectors, particularly AAV vectors, are described herein and in the art.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, preferably mammalian cells, most preferably human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene," "target polynucleotide," "transgene," "gene of interest" and the like generally refer to a gene or genes to be transferred using a vector. Typically, in the context of the present invention, such genes are located within the rAAV vector (which vector is flanked by inverted terminal repeat (ITR) regions and thus can be replicated and encapsidated into rAAV particles). Target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as E1A tumor suppressor genes or p53 tumor suppressor genes for the treatment of various cancers. To effect expression of the transgene in a recipient host cell, it is preferably operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rAAV vector may also contain a selectable marker.

A "gene" refers to a polynucleotide containing at least one open reading frame that is capable of encoding a particular protein after being transcribed and translated.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Preferably, the genetic element is introduced into a chromosome or mini-chromosome in the cell; but any alteration that changes the phenotype and/or genotype of the cell and its progeny is included in this term.

A cell is said to be "stably" altered, transduced or transformed with a genetic sequence if the sequence is available to perform its function during extended culture of the cell in vitro. In preferred examples, such a cell is "inheritably" altered in that a genetic alteration is introduced which is also inheritable by progeny of the altered cell.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred.

A preparation of AAV is said to be "substantially free" of helper virus if the ratio of infectious AAV particles to infectious helper virus particles is at least about $10^2:1$; preferably at least about $10^4:1$, more preferably at least about $10^6:1$; still more preferably at least about $10^8:1$. Preparations are also preferably free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Efficiency" when used in describing viral production, replication or packaging refers to useful properties of the method: in particular, the growth rate and the number of virus particles produced per cell. "High efficiency" production indicates production of at least 100 viral particles per cell; preferably at least about 10,000 and more preferably at least about 100,000 particles per cell, over the course of the culture period specified.

An "individual" or "subject" treated in accordance with this invention refers to vertebrates, particularly members of a mammalian species, and includes but is not limited to domestic animals, sports animals, and primates, including humans.

"Treatment" of an individual or a cell is any type of intervention in an attempt to alter the natural course of the individual or cell at the time the treatment is initiated, e.g., eliciting a prophylactic, curative or other beneficial effect in the individual. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

The practice of the present invention will employ, unless otherwise indicated, conventional techniques of molecular biology, virology, microbiology, recombinant DNA, and immunology, which are within the skill of the art. Such techniques are explained fully in the literature. See, e.g., Sambrook, Fritsch, and Maniatis, *Molecular Cloning: A Laboratory Manual*, Second Edition (1989); *Oligonucleotide Synthesis* (M. J. Gait Ed., 1984); *Animal Cell Culture* (R. I. Freshney, Ed., 1987); the series *Methods in Enzymology* (Academic Press, Inc.); *Gene Transfer Vectors for Mammalian Cells* (J. M. Miller and M. P. Calos eds. 1987); *Handbook of Experimental Immunology*, (D. M. Weir and C. C. Blackwell, Eds.); *Current Protocols in Molecular Biology* (F. M. Ausubel, R. Brent, R E. Kingston, D. D. Moore, J. G. Siedman, J. A. Smith, and K. Struhl, eds., 1987); *Current Protocols in Immunology* (J. E. Coligan, A. M. Kruisbeek, D. H. Margulies, E. M. Shevach and W. Strober, eds., 1991); *Current Protocols in Protein Science* (John E. Coligan et al., eds., Wiley and Sons, 1995); and *Protein Purification: Principles and Practice* (Robert K Scopes, Springer-Verlag, 1994).

I. rAAV Vectors

Recombinant AAV vectors are potentially powerful tools for human gene therapy, particularly for diseases such as cystic fibrosis and sickle cell anemia. A major advantage of rAAV vectors over other approaches to gene therapy is that they generally do not require ongoing replication of the target cell in order to become stably integrated into the host cell.

rAAV vectors and/or viruses may also contain one or more detectable markers. A variety of such markers are known, including, by way of illustration, the bacterial beta-galactosidase (lacZ) gene; the human placental alkaline phosphatase (AP) gene and genes encoding various cellular surface markers which have been used as reporter molecules both in vitro and in vivo. The rAAV vectors and/or viruses may also contain one or more selectable markers.

Recombinant AAV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts).

II. Selection and Preparation of AAV Vector

Adeno-associated viruses of any serotype are suitable to prepare rAAV, since the various serotypes are functionally and structurally related, even at the genetic level (see, e.g., Blacklow, pp. 165-174 of *Parvoviruses and Human Disease*, J. R. Pattison, ed. (1988); and Rose, *Comprehensive Virology*, 3, 1, 1974). All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed.

An AAV vector of the invention typically comprises a polynucleotide that is heterologous to AAV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and are preferred when it is desired that the therapeutic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or preferably in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, preferably (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters are preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. An especially preferred sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the AAV rep gene with the putative helper-virus-inducible promoter (either known in the art or identified using well-known techniques such as linkage to promoter-less "reporter" genes). The AAV rep-cap genes (with p5 replaced), preferably linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Given the relative encapsidation size limits of various AAV genomes, insertion of a large heterologous polynucleotide into the genome necessitates removal of a portion of the AAV sequence. Removal of one or more AAV genes is in any case desirable, to reduce the likelihood of generating replication-competent AAV ("RCA"). Accordingly, encoding or promoter sequences for rep, cap, or both, are preferably removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are preferably not flanked by AAV ITRs and preferably do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

III. Generating rAAV

To generate recombinant AAV particles useful for such purposes as gene therapy, the packaging cell line is preferably supplied with a recombinant AAV vector comprising AAV inverted terminal repeat (ITR) regions surrounding one or more polynucleotides of interest (or "target" polynucleotides).

The target polynucleotide is generally operably linked to a promoter, either its own or a heterologous promoter. A large number of suitable promoters are known in the art, the choice of which depends on the desired level of expression of the target polynucleotide (i.e., whether one wants constitutive expression, inducible expression, cell-specific or tissue-specific expression, etc.).

Preferably, the rAAV vector also contains a positive selectable marker in order to allow for selection of cells that have been infected by the rAAV vector. Negative selectable markers can also be included; as a means of selecting against those same cells should that become necessary or desirable. In a preferred embodiment, one can make use of the "bifunctional selectable fusion genes" described by S. D. Lupton; see, e.g., PCT/US91/08442 and PCT/US94/05601. Briefly, those constructs involve direct translational fusions between a dominant positive selectable marker and a negative selectable marker. Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

Useful target polynucleotides can be employed in rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as the wild-type p53 tumor suppressor cDNA for replacement of the missing or damaged p53 gene associated with some lung and breast cancers, or the E1A tumor suppressor gene which is capable of inhibiting tumorigenesis and/or metastasis of a variety of different cancers including breast and ovarian cancers.

Since the therapeutic specificity of the resulting recombinant AAV particle is determined by the particular vector or pro-vector introduced, the same basic packaging cell line can be modified for any of these applications. For example, a vector comprising a specific target polynucleotide can be introduced into the packaging cell for production of the AAV vector by any of several possible methods; including, for example, electroporation or transfection of a plasmid comprising an rAAV pro-vector, or infection with an rAAV or helper virus comprising an rAAV vector or pro-vector.

Helper virus can be introduced before, during or after introduction of the rAAV vector. For example, the plasmid can be co-infected into the culture along with the helper virus; and the cells can then be cultured for a sufficient period, typically 2-5 days, in conditions suitable for replication and packaging as known in the art (see references above and examples below). Lysates are prepared, and the recombinant AAV vector particles are purified by techniques known in the art.

In a preferred embodiment, also illustrated in the Examples below, a recombinant AAV vector is itself stably integrated into a mammalian cell to be used for packaging. Such rAAV "producer cells" can then be grown and stored until ready for use. To induce production of rAAV particles from such producer cells, the user need only infect the cells with helper virus and culture the cells under conditions suitable for replication and packaging of AAV (as described below).

Alternatively, one or more of the AAV split-packaging genes or the rAAV vector can be introduced as part of a recombinant helper virus. For example, the E1, E3 and/or the E4 genes of adenovirus can be replaced with one or more split-packaging genes or an rAAV vector. Techniques for facilitating cloning into adenovirus vectors, e.g., into the E1 and/or E3 regions, are known in the art (see, e.g., Bett, A. J. et al., Proc. Natl. Acad. Sci. USA, 91, 8802-8806 (1994)). Thus, a helper virus such as a recombinant adenovirus, can be used to provide helper virus functions as well as AAV packaging genes and/or an rAAV pro-vector, since (as is known in the art) a number of genes in such a helper virus (e.g., the E3 gene of adenovirus) can be replaced without eliminating helper virus activity. Additional genes can be inserted into such a helper virus by providing any necessary helper virus functions in trans. For example, human 293 cells contain adenoviral genes that can complement adenoviral E1 mutants. Thus, heterologous genes can also be cloned into an adenovirus in which the E1 genes have been deleted, for use in cells that can effectively provide such adenoviral functions in trans. Alternatively, the use of a helper virus can be eliminated by providing all necessary helper virus functions in the packaging cell.

IV. Introduction of Genetic Material into Cells

As is described in the art, and illustrated both herein and in the references cited above, genetic material can be introduced into cells (such as mammalian "producer" cells for the production of AAV) using any of a variety of means to transform or transduce such cells. By way of illustration, such techniques include, for example, transfection with bacterial plasmids, infection with viral vectors, electroporation, calcium phosphate precipitation, and introduction using any of a variety of lipid-based compositions (a process often referred to as "lipofection"). Methods and compositions for performing these techniques have been described in the art and are widely available.

Selection of suitably altered cells may be conducted by any technique in the art. For example, the polynucleotide sequences used to alter the cell may be introduced simultaneously with or operably linked to one or more detectable or selectable markers as is known in the art. By way of illustration, one can employ a drug-resistance gene as a selectable marker. Drug-resistant cells can then be picked and grown, and then tested for expression of the desired sequence, i.e., a packaging gene product, or a product of the heterologous polynucleotide, as appropriate. Testing for acquisition, localization and/or maintenance of an introduced polynucleotide can be performed using DNA hybridization-based techniques (such as Southern blotting and other procedures as is known in the art). Testing for expression can be readily performed by Northern analysis of RNA extracted from the genetically altered cells, of by indirect immunofluorescence for the corresponding gene product. Testing and confirmation of packaging capabilities and efficiencies can be obtained by introducing to the cell the remaining functional components of AAV and a helper virus, to test for production of AAV particles. Where a cell is inheritably altered with a plurality of polynucleotide constructs, it is generally more convenient (though not essential) to introduce them to the cell separately, and validate each step seriatim. References describing such techniques include those cited herein.

V. Selection and Preparation of Helper Virus

As discussed above, AAV is a parvovirus that is defective for self-replication, and must generally rely on a helper virus to supply certain replicative functions. A number of such helper viruses have been identified, including adenoviruses, herpes viruses (including but not limited to HSV1, cytomegalovirus and HHV-6), and pox viruses (particularly vaccinia). Any such virus may be used with this invention.

Frequently, the helper virus is an adenovirus of a type and subgroup that can infect the intended host cell. Human adenovirus of subgroup C, particularly serotypes 1, 2, 4, 6, and 7, are commonly used. Serotype 5 is generally preferred.

The features and growth patterns of adenovirus are known in the art. The reader may refer, for example, to Horowitz, "Adenoviridae and their replication," pp. 771-816 in *Fundamental Virology*, Fields et al., eds. The packaged adenovirus genome is a linear DNA molecule, linked through adenovirus ITRs at the left- and right-hand termini through a terminal protein complex to form a circle. Control and encoding regions for early, intermediate, and late components overlap within the genome. Early region genes are implicated in replication of the adenovirus genome, and are grouped depending on their location into the E1, E2, E3, and E4 regions.

Although not essential, in principle it is desirable that the helper virus strain be defective for replication in the subject ultimately to receive the genetic therapy. Thus, any residual helper virus present in an rAAV preparation will be replication-incompetent. Adenoviruses from which the E1A or both the E1A and the E3 region have been removed are not infectious for most human cells. They can be replicated in a permissive cell line (e.g., the human 293 cell line) which is capable of complementing the missing activity. Regions of adenovirus that appear to be associated with helper function, as well as regions that do not, have been identified and described in the art (see, e.g., P. Colosi et al., WO97/17458, and references cited therein).

VI. Uses of rAAV for Gene Therapy

AAV vectors can be used for administration to an individual for purposes of gene therapy. Suitable diseases for gene therapy include but are not limited to those induced by viral, bacterial, or parasitic infections, various malignancies and hyperproliferative conditions, autoimmune conditions, and congenital deficiencies.

Gene therapy can be conducted to enhance the level of expression of a particular protein either within or secreted by the cell. Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene.

The introduction of rAAV vectors by the methods of the present invention may involve use of any number of delivery techniques (both surgical and non-surgical) which are available and well known in the art. Such delivery techniques, for example, include vascular catheterization, cannulization, injection, inhalation, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition and dosage ranges of vector solutions are within the skill of the art.

In particular, for delivery of a vector of the invention to a tissue, any physical or biological method that will introduce the vector to a host animal can be employed. Vector means both a bare recombinant vector and vector DNA packaged into viral coat proteins, as is well known for AAV administration. Simply dissolving an AAV vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport.) Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the AAV vector as a free acid (DNA contains acidic phosphate groups) or a pharmacologically acceptable salt can be prepared in water suitably mixed with a surfactant such as hydroxypropylcellulose. A dispersion of AAV viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the AAV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

Of particular interest is the correction of the genetic defect of cystic fibrosis, by supplying a properly functioning cystic fibrosis transmembrane conductance regulator (CFTR) to the airway epithelium. Thus, rAAV vectors encoding native CFTR protein, and mutants and fragments thereof, are all preferred embodiments of this invention.

Compositions of this invention may be used in vivo as well as ex vivo. In vivo gene therapy comprises administering the vectors of this invention directly to a subject. Pharmaceutical compositions can be supplied as liquid solutions or suspensions, as emulsions, or as solid forms suitable for dissolution or suspension in liquid prior to use. For administration into the respiratory tract, a preferred mode of administration is by aerosol, using a composition that provides either a solid or liquid aerosol when used with an appropriate aerosolubilizer device. Another preferred mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, preferably at least about 80%, more preferably at least about 95%, and even more preferably at least about 99% of the cells of the desired tissue type. As a guide, the number of vector particles present in a single dose given by bronchoscopy will generally be at least about $1 \times 10^8$, and is more typically $5 \times 10^8$, $1 \times 10^{10}$, and on some occasions $1 \times 10^{11}$ particles, including both DNAse-resistant and DNAse-susceptible particles. In terms of DNAse-resistant particles, the dose will generally be between $1 \times 10^6$ and $1 \times 10^{14}$ particles, more generally between about $1 \times 10^8$ and $1 \times 10^{12}$ particles. The treatment can be repeated as often as every two or three weeks, as required, although treatment once in 180 days may be sufficient.

To confirm the presence of the desired DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence of a polypeptide expressed from a gene present in the vector, e.g., by immunological means (immunoprecipitations, immunoaffinity columns, ELISAs and Western blots) or by any other assay useful to identify the presence and/or expression of a particular nucleic acid molecule falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

Thus, the effectiveness of the genetic alteration can be monitored by several criteria. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic regimen is ultimately the responsibility of the prescribing physician.

The foregoing description provides, inter alia, methods for generating high titer preparations of recombinant AAV vectors that are substantially free of helper virus (e.g., adenovirus) and cellular proteins. It is understood that variations may be applied to these methods by those of skill in this art without departing from the spirit of this invention.

VII. Agents Useful in the Practice of the Invention

Agents useful in the practice of the invention include agents which alter rAAV transduction efficiency. Preferred agents are those which enhance or increase rAAV transduction. Such agents include agents which enhance viral endocytosis, e.g., brefeldin A, endosomal processing and/or trafficking to the nucleus, e.g., cysteine protease inhibitors. Preferably, the inhibitors are endosomal, e.g., lysosomal, cysteine protease inhibitors. More preferably, the agents of the invention are reversible cysteine protease inhibitors. Cysteine protease inhibitors within the scope of the invention include the cystatins, e.g., cystatin B or cystatin C, antipain, leupeptin, E-64, E-64c, E-64d, KO2 (Wacher et al., *J. Pharma. Sci.*, 87, 1322 (1998)), LLnL, Z-LLL, CBZ-Val-Phe-H, cysteine protease inhibitors such as those disclosed in U.S. Pat. Nos. 5,607,831, 5,374,623, 5,639,732, 5,658,906, 5,714,484, 5,560,937, 5,374,623, 5,607,831, 5,723,580, 5,744,339, 5,827,877, 5,852,007, and 5,776,718, JP 10077276, JP 8198870, JP 8081431, JP 7126294, JP 4202170, WO 96/21006 and WO 96/40737.

Preferred cysteine protease inhibitors are peptides or analogs thereof. Preferred peptide cysteine protease inhibitors within the scope of the invention comprise 2 to 20, more preferably 3 to 10, and even more preferably 3 to 8, amino acid residues. "Amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, nor-leucine, nor-valine, and tert-butylglycine). Peptide analogs are molecules which comprise at least one amino acid in D form and/or an unnatural amino acid, or other moiety which is not a natural amino acid.

Preferred peptide cysteine protease inhibitors include a compound of formula (I): $R_1$-A-$(B)_n$—C wherein $R_1$ is an N-terminal amino acid blocking group; each A and B is independently an amino acid; C is an amino acid wherein the terminal carboxy group has been replaced by a formyl (CHO) group; and n is 0, 1, 2, or 3; or a pharmaceutically acceptable salt thereof. In one preferred embodiment, $R_1$ is $(C_1$-$C_{10})$alkanoyl, acetyl or benzyloxycarbonyl. In another preferred embodiment, each A and B is independently alanine, arginine, glycine, isoleucine, leucine, valine, nor-leucine or nor-valine, and more preferably each A and B is isoleucine. In yet another preferred embodiment, C is alanine, arginine, glycine, isoleucine, leucine, valine, nor-leucine or nor-valine, wherein the terminal carboxy group has been replaced by a formyl (CHO) group, and more preferably, C is nor-leucine or nor-valine, wherein the terminal carboxy group has been replaced by a formyl (CHO) group.

In a further preferred embodiment, $R_1$ is $(C_1$-$C_{10})$alkanoyl or benzyloxycarbonyl; A and B are each isoleucine; C is nor-leucine or nor-valine, wherein the terminal carboxy group has been replaced by a formyl (CHO) group; and N is 1.

Also included within the scope of the invention is a compound of formula (II):

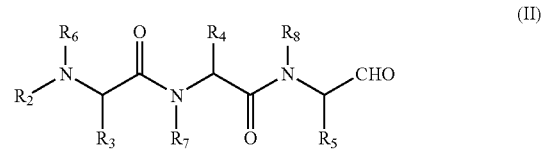

wherein $R_2$ is an N-terminal amino acid blocking group;

$R_3$, $R_4$, and $R_5$ are each independently hydrogen, $(C_1$-$C_{10})$ alkyl, aryl or aryl$(C_1$-$C_{10})$alkyl; and $R_6$, $R_7$, and $R_8$ are each independently hydrogen, $(C_1$-$C_{10})$ alkyl, aryl or aryl$(C_1$-$C_{10})$alkyl; or a pharmaceutically acceptable salt thereof. Preferably, $R_2$ is $(C_1$-$C_{10})$alkanoyl, acetyl or benzyloxycarbonyl. Also preferably, $R_3$ is hydrogen or $(C_1$-$C_{10})$alkyl, e.g., 2-methylpropyl. It is preferred that $R_4$ is hydrogen or $(C_1$-$C_{10})$alkyl, e.g., 2-methylpropyl.

In another preferred embodiment, $R_5$ is hydrogen or $(C_1$-$C_{10})$alkyl, for example, butyl or propyl.

In a further preferred embodiment, $R_2$ is acetyl or benzyloxycarbonyl; $R_3$ and $R_4$ are each 2-methylpropyl; $R_5$ is butyl or propyl; and $R_6$, $R_7$, and $R_8$ are each independently hydrogen.

Another preferred agent useful in the methods of the invention is a compound of formula (III):

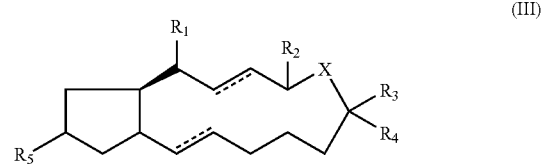

wherein $R_1$ is H, halogen, $(C_1$-$C_{10})$alkyl, $(C_1$-$C_{10})$alkenyl, $(C_1$-$C_{10})$ alkynyl, $(C_1$-$C_{10})$alkoxy, $(C_1$-$C_{10})$alkanoyl, (═O), (═S), OH, SR, CN, $NO_2$, trifluoromethyl or $(C_1$-$C_{10})$alkoxy, wherein any alkyl, alkenyl, alkynyl, alkoxy or alkanoyl may optionally be substituted with one or more halogen, OH, SH, CN, $NO_2$, trifluoromethyl, NRR or SR, wherein each R is independently H or $(C_1$-$C_{10})$alkyl;

$R_2$ is (═O) or (═S);

$R_3$ is H, $(C_1$-$C_{10})$alkyl, $(C_1$-$C_{10})$alkenyl, $(C_1$-$C_{10})$alkynyl, $(C_1$-$C_{10})$alkoxy or $(C_3$-$C_8)$cycloalkyl, wherein any alkyl, alkenyl, alkynyl, alkoxy or cycloalkyl may optionally be substituted with one or more halogen, OH, CN, $NO_2$, trifluoromethyl, SR, or NRR, wherein each R is independently H or $(C_1$-$C_{10})$alkyl;

$R_4$ is H, $(C_1$-$C_{10})$alkyl, $(C_1$-$C_{10})$alkenyl, $(C_1$-$C_{10})$alkynyl, $(C_1$-$C_{10})$alkoxy or $(C_3$-$C_8)$cycloalkyl, wherein any alkyl, alkenyl, alkynyl, alkoxy or cycloalkyl may optionally be substituted with one or more halogen, OH, CN, $NO_2$, trifluoromethyl, SR, or NRR, wherein each R is independently H or $(C_1$-$C_{10})$alkyl;

$R_5$ is H, halogen, $(C_1-C_{10})$alkyl, $(C_1-C_{10})$alkenyl, $(C_1-C_{10})$alkynyl, $(C_1-C_{10})$alkoxy, $(C_1-C_{10})$alkanoyl, (=O), (=S), OH, SR, CN, $NO_2$ or trifluoromethyl, wherein any alkyl, alkenyl, alkynyl, alkoxy or alkanoyl may optionally be substituted with one or more halogen, OH, SH, CN, $NO_2$, trifluoromethyl, NRR or SR, wherein each R is independently H or $(C_1-C_{10})$alkyl; and X is O, S or NR wherein R is H or $(C_1-C_{10})$alkyl; or a pharmaceutically acceptable salt thereof.

The following definitions apply unless otherwise stated. Alkyl denotes a straight or a branched group, but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

Suitable N-amino acid blocking groups are known to those skilled in the art (See, for example, T. W. Greene, *Protecting Groups In Organic Synthesis*; Wiley: New York, 1981, and references cited therein). Preferred values for $R_1$ include $(C_1-C_{10})$alkanoyl (e.g. acetyl) and benzyloxycarbonyl.

VIII. Dosages, Formulations and Routes of Administration of the Agents of the Invention Administration of the agents identified in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. When the agents of the invention are employed for prophylactic purposes, agents of the invention are amenable to chronic use, preferably by systemic administration.

The agents of the invention, including a compound of formula (I), (II), or (III), including their salts, are preferably administered at dosages of about 0.01 μM to about 1 mM, more preferably about 0.1 μM to about 40 μM, and even more preferably, about 1 μM to 40 μM, although other dosages may provide a beneficial effect. For example, preferred dosages of LLnL include about 1 μM to 40 μM while preferred dosages of ZLL include 0.1 μM to about 4 μM.

One or more suitable unit dosage forms comprising the agents of the invention, which, as discussed below, may optionally be formulated for sustained release, can be administered by a variety of routes including oral, or parenteral, including by rectal, transdermal, subcutaneous, intravenous, intramuscular, intraperitoneal, intrathoracic, intrapulmonary and intranasal routes. For example, for administration to the liver, intravenous administration is preferred. For administration to the lung, airway administration is preferred. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

When the agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents, for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The agents of the invention can also be formulated as elixirs or solutions for convenient oral administration or as solutions appropriate for parenteral administration, for instance by intramuscular, subcutaneous or intravenous routes.

The pharmaceutical formulations of the agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The agents of the invention can be delivered via patches for transdermal administration. See U.S. Pat. No. 5,560,922 for examples of patches suitable for transdermal delivery of an agent. Patches for transdermal delivery can comprise a backing layer and a polymer matrix which has dispersed or dissolved therein an agent, along with one or more skin permeation enhancers. The backing layer can be made of any suitable material which is impermeable to the agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of slin which in turn helps to reduce skin irritation and to prevent the adhesive polymer layer of the delivery system from failing.

Agents released from a transdermal delivery system must be capable of penetrating each layer of skin. In order to increase the rate of permeation of an agent, a transdermal drug delivery system must be able in particular to increase the permeability of the outermost layer of skin, the stratum corneum, which provides the most resistance to the penetration of molecules. The fabrication of patches for transdermal delivery of agents is well known to the art.

For administration to the upper (nasal) or lower respiratory tract by inhalation, the agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the agent may be administered via nose drops, a liquid spray, such as via a plastic bottle atomizer or metered-dose inhaler. Typical of atomizers are the Mistometer (Wintrop) and the Medihaler (Riker).

The local delivery of the agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of an agent of the invention present in a topical formulation will depend on various factors, but generally will be from 0.01% to 95% of the total weight of the formulation, and typically 0.1-25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The formulations and compositions described herein may also contain other ingredients such as antimicrobial agents, or preservatives. Furthermore, the active ingredients may also be used in combination with other agents, for example, bronchodilators.

The agents of this invention may be administered to a mammal alone or in combination with pharmaceutically acceptable carriers. As noted above, the relative proportions of active ingredient and carrier are determined by the solubility and chemical nature of the compound, chosen route of administration and standard pharmaceutical practice.

The dosage of the present agents will vary with the form of administration, the particular compound chosen and the physiological characteristics of the particular patient under treatment. Generally, small dosages will be used initially and, if necessary, will be increased by small increments until the optimum effect under the circumstances is reached.

The invention will be further described by, but is not limited to, the following examples.

Example 1

Polarity and Time Course of rAAV Transduction in Bronchial Epithelial Cells Methods Primary Culture of Polarized Human Bronchial Epithelia.

Primary human airway epithelial cells were collected by enzymatic digestion of bronchial samples from lung transplants as previously described (Kondo et al., 1991; Zhang et al., 1995). Isolated airway primary cells were seeded at a density of $5 \times 10^5$ cells/cm$^2$ onto collagen-coated Millicell-HA culture inserts (Millipore Corp., Bedford, Mass.). Primary cultures were grown at the air-liquid interface for more than 2 weeks, at which time differentiation into a mucociliary epithelium occurs. The culture medium, used to feed only the basolateral side of the cells, contained 49% DMEM, 49% Ham's F12 and 2% Ultraser G (BioSepra, Cedex, France).

Production of rAAV.

Recombinant AAV virus was produced by a CaPO$_4$ co-transfection protocol and was purified through three rounds of isopycnic cesium chloride ultracentrifugation, as previously described (Duan et al., 1997). The proviral plasmid, pCisAV.GFP3ori, was used to generate rAAV (AV.GFP3ori) encoding the GFP reporter gene under the transcriptional control of the CMV enhancer/promoter and SV40 poly-adenylation signal (Duan et al., 1998). Recombinant viral stocks were heated at 58° C. for 60 minutes to inactivate contaminating helper adenovirus. Typical yields were $2-5 \times 10^{12}$ particles/ml based on DNA slot blot hybridization assays against plasmid standards. The level of adenoviral contamination, as based on a second reporter assay for the recombinant adenovirus used for propagation (Ad.CMVAlkphos; Duan et al., 1997), was less than one functional particle per $1 \times 10^{10}$ DNA particles of rAAV (limits of sensitivity). Viral preparations were evaluated for the contamination of wtAAV by immunocytochemical staining of AV.GFP3ori/Ad.CMVLacZ co-infected 293 cells with anti-Rep antibodies (American Research Products, Inc., Belmont, Mass.) as previously described (Duan et al., 1998). All rAAV stocks demonstrated an absence of Rep immunoreactivity when $1 \times 10^{10}$ rAAV particles were used for infection (limits of sensitivity). Transfection with Rep/Cap encoding plasmids served as controls for antibody staining of Rep protein.

Infection of Polarized Airway Epithelia.

Purified stocks of rAAV were dialyzed in PBS prior to application on primary airway cultures. For infections of the airway cells, 5 µl AV.GFP3ori ($5 \times 10^9$ particles, approximate MOI=5000) was mixed with 100 ul of culture media and applied directly into the apical or basolateral compartment of the Millicell inserts. For both apical and basolateral infections, rAAV containing media was removed after 24 hours and replaced with either fresh culture media (for the basal side) or exposed to air (for the apical side).

Immunofluorescence Localization of Heparin Sulfate Proteoglycan.

Localization of AAV type-2 receptor (membrane-associated heparin sulfate proteoglycan) in polarized airway epithelia was performed on frozen sections following 4% paraformaldehyde fixation for 15 minutes, cryoprotection in sucrose, and embedding in OCT. Eight μm sections were blocked in 20% goat serum/PBS for 20 minutes followed by incubation in a 1:200 dilution of rat anti-heparin sulfate proteoglycan monoclonal antibody (Chemico International Inc., Temecula, Calif.). Antigens were detected by indirect immunofluorescence using a 1:250 dilution of FITC-conjugated goat anti-rat IgG (Jackson ImmunoResearch Laboratories, Inc., West Grove, Pa.). Nuclei were counter stained with propidium iodide (5 μg/ml). The specificity of the immunocytochemical staining was confirmed with competition experiments performed by pre-absorbing the primary antibody with either the specific competitor heparin sulfate (Sigma, St. Louis, Mo.), or a nonspecific competitor chondroitin sulfate C (Sigma, St. Louis, Mo.), at a final concentration of 5 μg/ml for 8 hours at 4° C. before applying antibody to the sections.

Results

Figure 2:
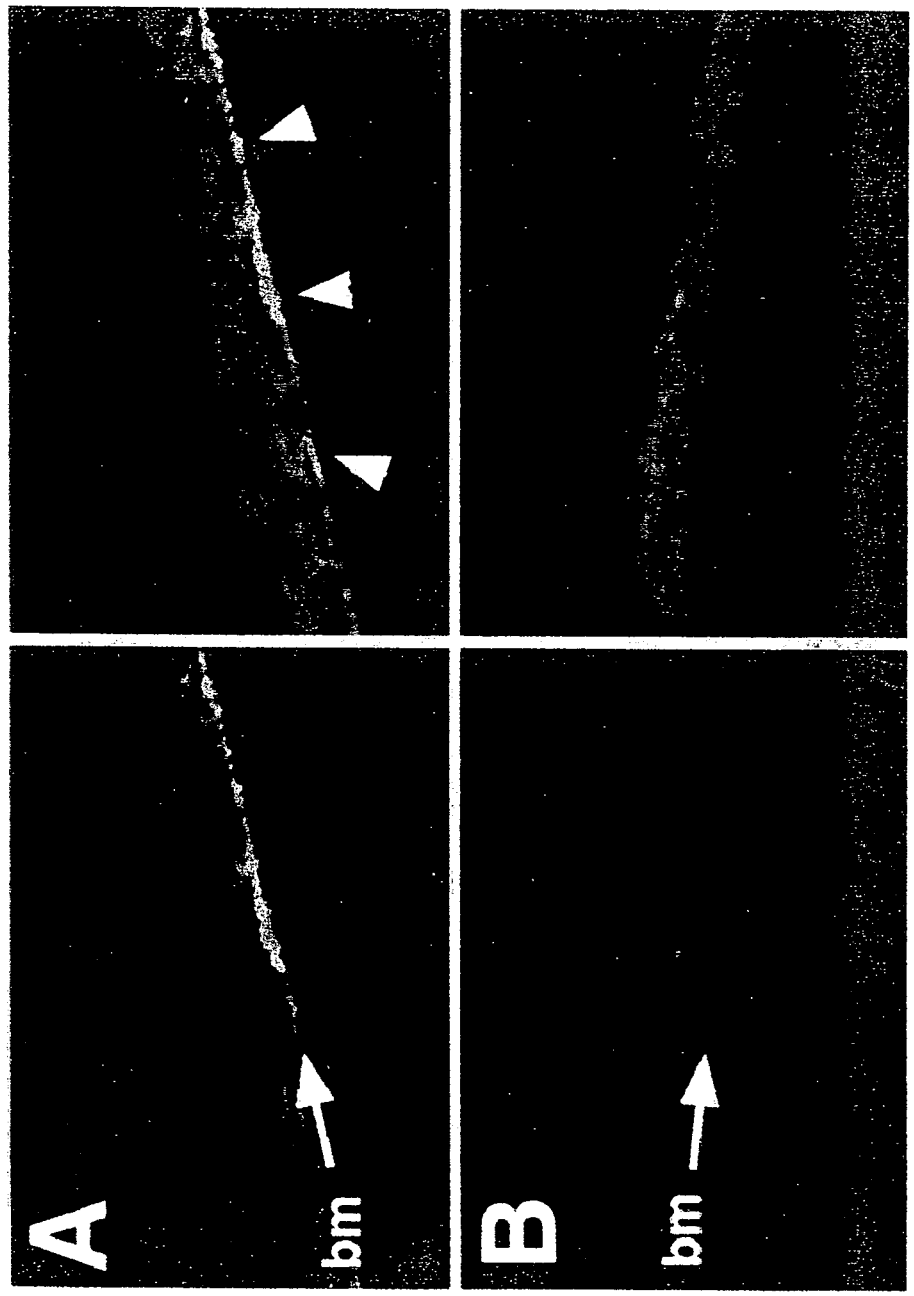
FIG. 2. Immunocytochemical localization of the AAV-2 receptor, heparin sulfate proteoglycan, in a polarized bronchial epithelial culture. Sections of fully differentiated human bronchial cultures were incubated with monoclonal antibody against heparin sulfate proteoglycan. Immunoreactivity was detected by indirect immunofluorescence using a FITC-labeled secondary antibody. Panel A depicts baseline immunostaining for heparin sulfate proteoglycan, which localized predominantly to the basal surface of the polarized bronchial epithelium. The specificity of immunoreactivity was confirmed by preincubation of the primary antibody with free heparin sulfate prior to immunostaining (Panel B).

A significant polarity to infection of polarized cultures of airway epithelial cells was demonstrated, with the basolateral membranes 200-fold more transducible than apical membranes (FIG. 1). Furthermore, these studies demonstrated that expression of the reporter GFP transgene required significant time (40 days) to reach maximal levels. Similar findings were obtained with other rAAV reporters such as AV.RSVAlkphos, suggesting that the time lag needed for transduction was not a result of the transgene cassette. Using immunofluorescent localization, one of the known AAV-2 receptors (membrane-associated heparin sulfate proteoglycan, HSPG), was found to have a limited pattern of expression localized to the basal surface of differentiated airway cells (FIG. 2).

Thus, transduction of polarized airway epithelia by rAAV is much greater from the basolateral as compared to the apical surface. This difference appears to be due, at least in part, to the restricted localization of HSPG on basal membranes. The identical localization patterns of HSPG were observed in native human bronchus tissue using two independent anti-HSPG antibodies (data not shown). Transient disruption of epithelial tight junctions by pretreatment of the apical surface with hypotonic EGTA solutions increased transduction of apically applied rAAV by 8-fold (Duan et al., 1998). Therefore, limited access to the basolateral membrane may be a barrier to rAAV transduction. Another interesting feature of rAAV transduction biology in the airway is the long time required for efficient transgene expression. This finding has two possible explanations. First, the transport of rAAV to the nucleus may be a slow rate-limiting process. Alternatively, the conversion of single-stranded rAAV genomes to expressible double-stranded forms may also be rate limiting.

Example 2

AAV Binding at the Basolateral Membrane

Although receptor abundance supports the notion that rAAV binding may be limiting at the apical surface, to conclusively demonstrate this fact requires direct assessment of virus binding. To this end, radiolabeled virus was used to study binding at 4° C. in the absence of endocytosis. In addition, total binding and entry was also studied under the same conditions described above for gene expression studies. Environmental stimuli known to enhance rAAV transduction in other systems (i.e., UV irradiation) were also evaluated.

Methods

Viral Binding and Uptake Assays.

Tritium-labeled AV.GFP3ori was prepared according to a previously published protocol (Summerford et al., 1998) with several modifications. Briefly, methyl-$^3$H thymidine (specific activity: 3159 GBq/mmol, NET-027Z, NEN Life Science Products, Inc. MA) was added to the cell culture medium at a final concentration of 1 μCi/ml at 7 hours post-transfection with pCisAV.GFP3ori and pRepCap plasmids and infection with Ad.CMVLacZ. $^3$H-AV.GFP3ori was purified. Typical yields were $3.6 \times 10^8$ particles/μl at a specific activity of $4 \times 10^{-7}$ cpm/virion. To assess the binding of rAAV to polarized bronchial epithelia cells, 100 μL $^3$H-AV.GFP3ori (MOI=60,000 particles/cell, with a total of $1.2 \times 10^4$ cpm, $3 \times 10^{10}$ particles), was applied to either the apical or basal surface, as described above, and incubated at 4° C. for 90 minutes. Combined binding/uptake of rAAV into differentiated airway epithelia was measured in the same settings except that the cultures were incubated at 37° C. for 24 hours before they were harvested. These combined viral binding/uptake assays were performed under infection conditions identical to those used for functional studies of rAAV transduction with transgene expression as an endpoint. After washing three times in PBS, cells were lysed in situ with 5 ml of Ready Safe liquid scintillation cocktail (Beckman Instruments, Inc., Fullerton, Calif.) at room temperature for 5 minutes and the radioactivity was quantitated in a scintillation counter. Calculation of the amount of bound and internalized rAAV particles was based on the known specific radioactivity of $^3$H-labeled virions.

UV Irradiation.

For the UV irradiation experiments, Millicell inserts were put transiently into empty 100 mm tissue culture plates (apical side up) and exposed to 25 j/m$^2$ of Lw light (254 nm). After irradiation, the Millicell inserts were quickly returned to plates containing Ultraser-G culture media on the basolateral side. Infections with rAAV were performed immediately following UV irradiation by application of $5 \times 10^9$ rAAV particles in 100 μl to either the apical or basolateral side of the support membrane as described above.

Results

Figure 3A:
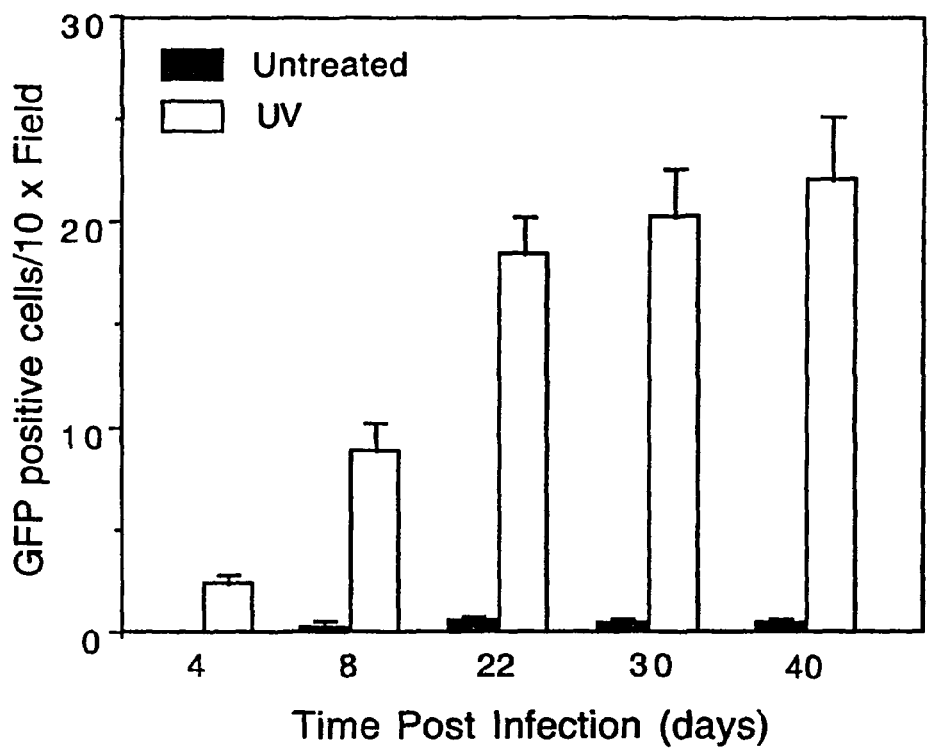
FIG. 3. Polarized airway epithelia were treated with UV (25 j/m$^2$) prior to infection with AV.GFP3ori virus (MOI=10,000 particles/cell) from the apical (Panel A) or basolateral side (Panel B) of primary cultures. The abundance of GFP transgene expressing cells was quantitated by indirect fluorescent microscopy at 4, 8, 22, 30, and 40 days. The results represent the mean (+/−SEM) of 4 independent experiments for each condition.
Figure 3B:
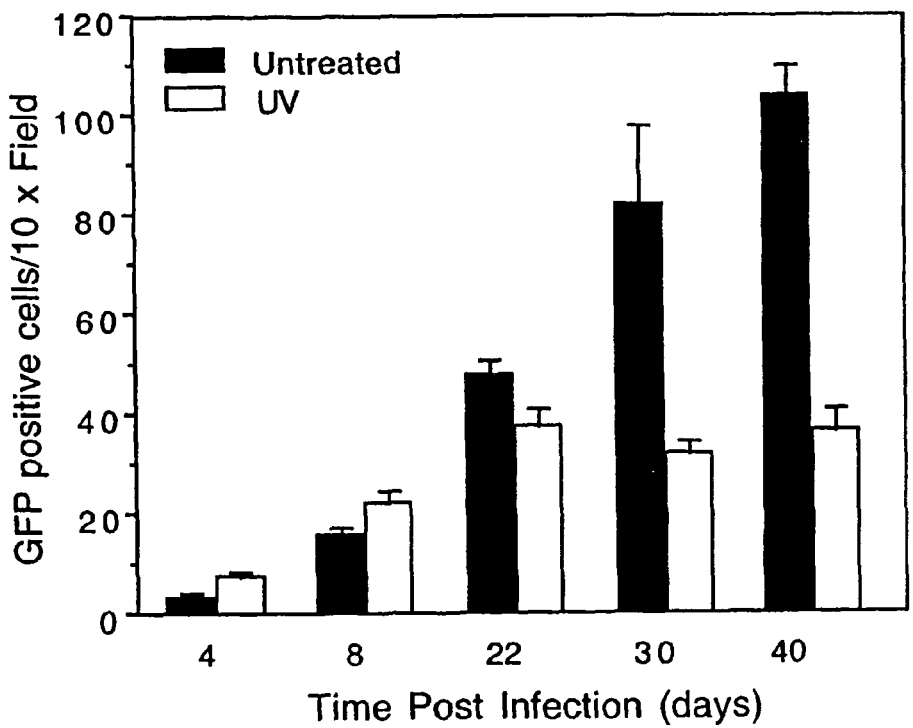

It has been previously demonstrated that the rAAV transduction efficiency can be improved in both immortalized cell lines and non-dividing primary cells by UV irradiation at dosages which do not significantly alter cell viability or proliferative capacity (Alexander et al., 1994; Ferrari et al., 1996). The effect of UV irradiation (25 j/m$^2$) prior to application of rAAV on either the apical side or basolateral sides of primary cultures was evaluated. As shown in FIG. 3A, a 30-fold increase in transgene expression was observed by 40 days post-treatment, when virus was added to the apical surface after UV stimulation. This result confirmed previous successes using UV to augment AAV transduction (Alexander et al., 1994; Ferrari et al., 1996). Interestingly, when AAV infection was performed on the basolateral side of uv-irradiated culture chambers, the efficiency decreased 2-fold by 40 days post-infection, as compared to non-irradiated controls also infected from the basolateral side (FIG. 3B). These results suggested that uv irradiation is capable of modulating rAAV transduction in polarized airway primary cultures. However, the magnitude and direction of this modulation is different depending on the cellular surface of infection. Enhanced transduction from the apical side following UV exposure could be due to asymmetric entry and/or processing pathways of AAV in the basal and apical compartments. Localization studies of HSPG following UV irradiation demonstrate no detectable increases at the apical surface but rather a near complete reduction of immunoreactivity at the basal membrane (Duan et al., 1998). These findings suggest two potential explanations for variations in rAAV transduction following UV irradiation. First, the reduction in basal infectivity following UV may in part be due to the reduction of HSPG receptor. Second, the fact that UV was capable of increasing rAAV transduction at the apical membrane in the absence of detectable HSPG receptor suggests that alternative pathways for AAV binding and uptake must occur at the apical membrane.

Figure 4:
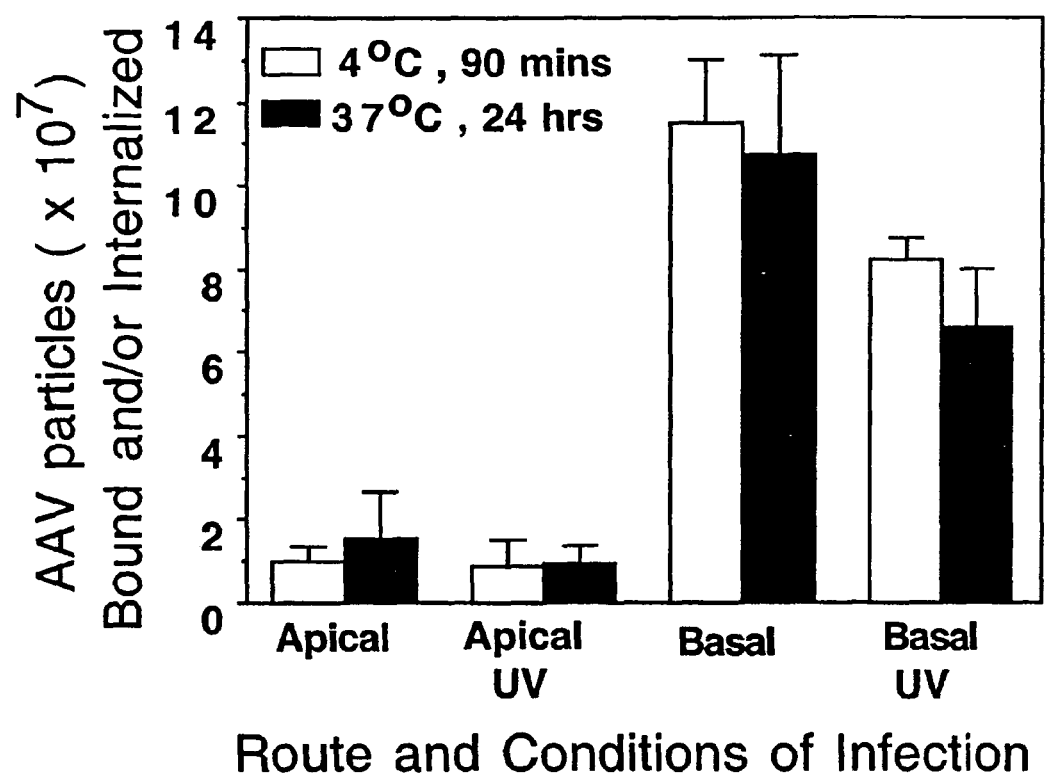
FIG. 4. The ability of polarized bronchial epithelial cultures to bind and internalize virus applied to either the apical or basolateral surfaces was quantified using radiolabeled rAAV ($^3$H-AV.GFP3ori). Two experimental conditions evaluated either viral binding (4° C. incubation with virus for 90 minutes) or the total amount of bound and internalized virus over a prolonged incubation period (37° C. incubation with virus for 24 hours). The results represent the mean (+/−SEM) of 5 independent experiments for each condition.

To further investigate the mechanisms of UV augmentation and the correlation of HSPG receptor abundance with rAAV transduction, radioactively labeled rAAV was employed to assess binding and virus uptake. Findings from these studies confirmed higher binding at 4° C. to the basolateral membrane and thus support HSPG localization studies (FIG. 4). However, the fact that differences in binding were only 6-7 fold suggest that other aspects of rAAV transduction in addition to binding must be responsible for the 200-fold variation in transduction from the apical and basolateral membranes. A second unique finding was that virus binding and uptake at 37° C. for 24 hours was equivalent to that at 4° C. from both the apical and basolateral membranes (FIG. 4). This observation suggests that viral binding may be relatively efficient and that uptake (or endocytosis) of virus may be a limiting factor involved in rAAV transduction. Furthermore, following UV irradiation, which increased apical transduction by 30-fold, resulted in no detectable change in virus binding/uptake from apical membrane at either 4° C. or 37° C. Such findings underscore the fact that rAAV binding alone does not correlate with the efficiency of rAAV transduction.

Figure 5:
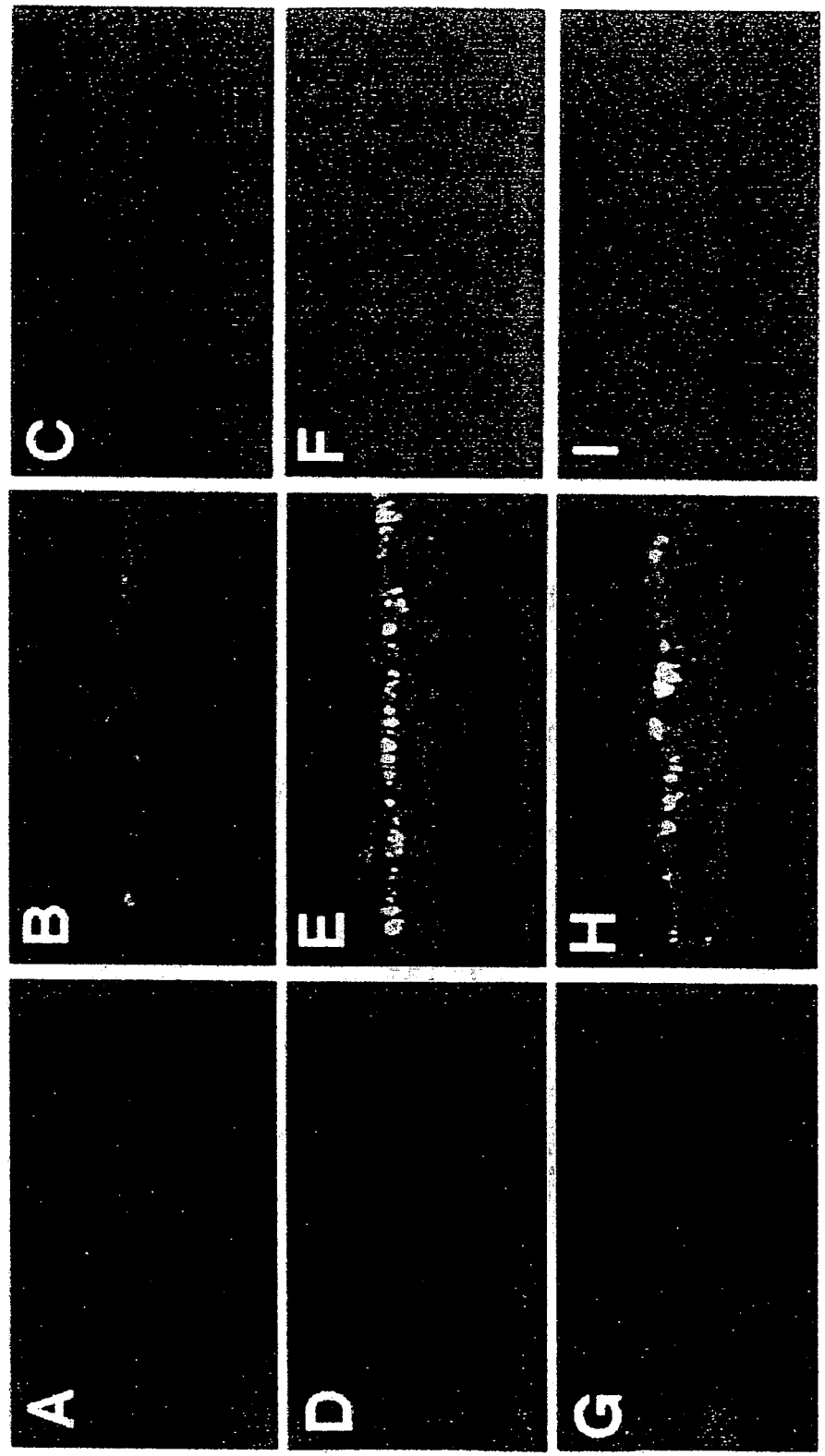
FIG. 5. Endocytosis was evaluated in polarized airway epithelia using 200 nm Nile Red fluorescent beads (size of AAV virions). Beads were applied to the apical or basolateral surfaces under conditions which were identical to viral infection experiments. 2-D confocal reconstitution images in Panels A, B, D, E, G, and H depict cross-sectional localization of internalized fluorescent beads in the subapical compartment of the cytoplasm following apical (A-C) and basolateral (D-F) application of beads. Panels G-I represent cultures treated with UV (25 joules/m$^2$) prior to apical application of beads. Several independent incubation time points were evaluated, of which 5 minutes (A, D, and G) and 6 hours (B, E, and H) are shown. En face photomicrographs taken by low power (2.5×) indirect fluorescent microscopy are also shown for 6 hour incubation time points (C, F, and I). For reasons which are unclear, beads accumulate within a subapical compartment regardless of the epithelial side of application.

To further evaluate other factors which might be responsible for differences in rAAV transduction from the apical and basolateral membranes, Nile Red beads (with similar size to AAV particles, 20 μm) were utilized to assess the rate of endocytosis from apical and basolateral membranes. These studies demonstrated that basolateral membranes had a significantly higher rate of receptor-independent endocytosis than apical membranes (FIG. 5). Furthermore, following UV irradiation, uptake of Nile Red beads was significantly increased (FIG. 5). These findings implicate endocytosis of virus as a rate-limiting step induced by UV irradiation in the absence of increased vector binding.

These findings highlight the functional differences between apical and basolateral membranes in polarized airways epithelia and suggest that both higher levels of binding and higher rates of endocytosis at the basal membrane may be responsible for increased transduction. Furthermore, V irradiation to the apical membrane, which causes significant reorganization of cytoskeletal structures including microvilli (Duan et al., 1998), resulted in a significant increase in apical but not basolateral membrane endocytosis in the absence of changes in virus binding. These studies implicate the rate of endocytosis and/or trafficking of virus to the nucleus as a rate-limiting step in rAAV transduction from the apical membrane.

Example 3

Evaluation of Viral Endocytosis and Trafficking to the Nucleus Using Cy3 Labeled rAAV To assess endocytosis and nuclear trafficking of AAV following treatment with various agents which may modulate these processes, fluorescently labeled virus was prepared. Virus was labeled using the following protocol: Three times CsCl banded rAAV (AV.GFP3ori) was conjugated with the bifunctional NHS-ester carbocyanine-Cy3 using a modified procedure from Amersham (Piscataway, N.J.). This procedure conjugates Cy3 to amine groups in the viral capsid as esters linkages. Briefly, $5 \times 10^{11}$ particles of the virus were incubated for 30 minutes at 4° C. with increasing concentrations of the NHS-ester carbocyanine-Cy3 due in a reaction volume of 1 ml. Several experimental conditions evaluated crosslinking reactions with dye:rAAV particle ratios of 0.2, 1, 5, 25, 100, and 200. The solution was transferred to a dialysis chamber (10,000 MW cut-off; Gibco BRL, Gaithersburg, Md.) and dialyzed for 24 hours against 2 changes of dialysis buffer containing 20 mM HEPES pH 7.5, 150 mM NaCl. Lastly, the samples were dialyzed in DMEM with no serum overnight and concentrated in a Centricon 30 (Amicon). This solution was used directly for viral infections of Hela cells on glass slides at 4° C. for 90 minutes in the absence of serum. Following 4° C. binding of virus, slides were washed in serum-free media two times and either fixed for analysis or shifted to 37° C. for continued infection in the presence of 10% serum-containing media. Conditions with dye-to-particle ratio of 100 gave the best result.

Results from these labeling experiments are shown in FIG. 18 and demonstrate that labeled virus effectively binds to the cell surface at 4° C. in the absence of endocytosis as expected. By 60 minutes at 37° C., a visible increase in the abundance of virus in the cytoplasm was noted which was effectively transported to the nucleus by 120 minutes at 37° C. (FIGS. 18A and B). Additionally, labeled virus retained greater than 95% functional transduction of GFP expression at 24 hours post-infection on Hela cells as compared to the same mock-labeled stock of virus. Viral binding was inhibited in a dose-dependent fashion by heparin at the time of infection (FIG. 18C). Heparin has been previously shown to inhibit most of rAAV transduction in Hela cells by blocking binding with heparin sulfate proteoglycan receptors. Cy3-labeled rAAV retained greater than 95% of its functional transducing activity as measured by GFP transgene expression. Thus, most labeled virions are functionally active for endocytosis. With respect to endocytosis of rAAV in polarized airway epithelial cell models, co-localization of Cy3-labeled rAAV with FITC-labeled transferrin demonstrates that the majority of AAV particles are endocytosed in transferrin-containing vesicles (FIG. 18D). Thus, rAAV may be endocytosed through clathrin-coated pits.

Example 4

Endosomal Processing Limits AAV Transduction

Based on the finding that basolateral membranes have higher endocytic rates and UV irradiation enhances endosomal uptake and rAAV transduction from the apical membrane, it is possible that endosomal pathways influencing viral uptake and transport to the nucleus may be limiting from the apical membrane. In contrast, these pathways may be active at maximal levels from the basolateral membrane of airway epithelial cells. To further investigate the importance of endosomal processing, the effect(s) of several chemical compounds known to alter endosomal processing was evaluated.

Methods

Initial studies were performed in confluent primary human fibroblasts since dose titrations and toxicity could be quickly assessed. Selected compounds were used to treat fibroblast monolayers prior to rAAV infection. rAAV transduction was assessed at 96 hours post-infection by FACS analysis, and the percentage of dead cells was simultaneously assessed by incorporation of propidium iodide.

These compounds included nocodazole (Sigma, St. Louis, Mo.; depolymerizes microtubules and causes lysosomal scattering); vinblastine sulfate (Sigma, St. Louis, Mo.; depolymerizes microtubules, inhibits endocytosis by blocking intracellular endosomes and lysosomes movement); cytochalasin B (Sigma, St. Louis, Mo.; depolymerizes microfilaments, i.e., actin, and blocks fusion of endosome with lysosome. Inhibits endocytosis by blocking intracellular endosome and lysosome movement); brefeldin A (BFA, Sigma, St. Louis, Mo.; reversibly blocks protein transport from the ER to the Golgi. BFA has also been shown to increase endocytosis from the apical but not basolateral membranes, see Prydz et al. (1992)); $NH_4Cl$ (Sigma, St. Louis, Mo.; lysosomotropic reagent which raises endosomal pH, and has been shown to inhibit canine parvovirus uncoating, see Basak et al. (1992)); chloroquine (Sigma, St. Louis, Mo.; lysosomotropic reagent which raises endosomal pH and inhibits lysosomal cysteine protease cathepsin B, and has been shown to inhibit canine parvovirus uncoating, see Basak et al. (1992)); and LLnL (N-acetyl-L-Leucinyl-L-leucinal-L-norleucinal; Calbiochem-Novabiochem Corp., La Jolla, Calif.) and Z-LLL (N-carbobenzoxyl-L-leucinyl-L-leucinyl-L-norvalinal; Calbiochem-Novabiochem Corp., La Jolla, Calif.), which are tripeptidyl aldehydecysteine protease inhibitors. These tripeptides are structurally related to chloroquine but have different lipid solubility and specificity for cysteine roteases (Seglen, 1983). These molecules decrease endosomal degradation of molecules by a mechanism different than altering pH. They also have been shown to inhibit 26S ubiquitin and proteasome-dependent proteolytic pathways (Rock et al., 1994).

Results

Figure 6:
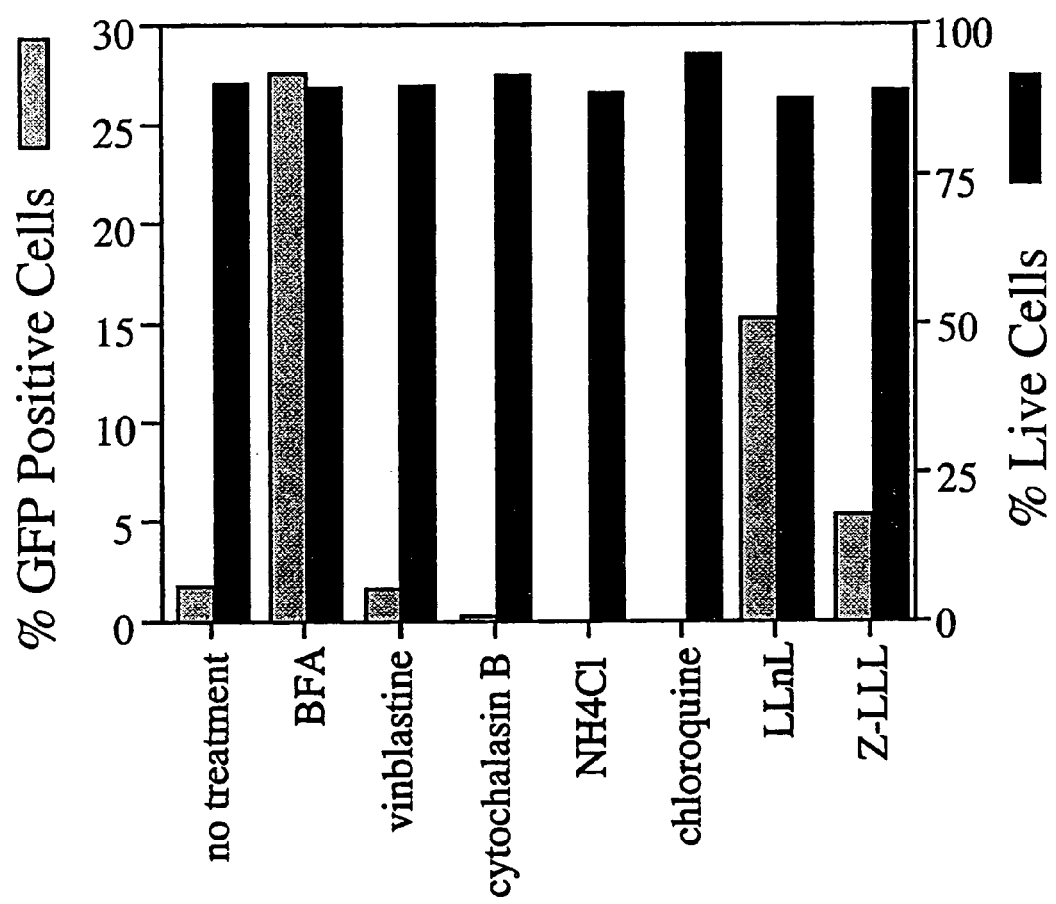
FIG. 6. Primary confluent fibroblasts were infected with AV.GFP3ori virus at an MOI=1000 particles/cell following treatment with brefeldin A (10 μg/ml), vinblastine (22 μM), cytochalasin B (1 μM), NH$_4$Cl (2 mM), chloroquine (20 μm), LLnL (400 μM), and Z-LLL (4 μM), final concentration indicated in brackets. Cells were harvested at 96 hours post-infection and the transduction efficiency was compared to untreated rAAV infected cells by FACS analysis for GFP expression. To control for non-specific effects caused by toxicity of the compounds, the percentage of live cells was also assessed by the absence of propidium iodide incorporation. Only doses which were non-toxic are shown.

As previously reported for canine parvovirus (Basake et al., 1992), both $NH_4Cl$ and chloroquine, which raise the endosomal pH, significantly inhibited rAAV transduction (FIG. 6). These results support the importance of endosomal pH in facilitating virus release and/or uncoating following infection. Moreover agents such as cytochalasin B, which disrupt microfilament formation, led to a significant decrease in rAAV transduction, suggesting that actin microfilaments likely play some role in rAAV transduction. Further, vinblastine, which facilitates both microtubule depolymerization and decreases endocytosis in MDCK cells, had little effect on rAAV transduction.

Most interestingly, however, treatment with BFA, which disrupts ER to Golgi vesicular transport and has also been shown to increase apical membrane endocytosis in MDCK cells (Prydz et al., 1992), led to a significant enhancement of rAAV transduction. The importance of ER to Golgi vesicular transport is unclear, but given the findings that UV irradiation also enhances membrane endocytosis and BFA has been suggested to do the same, these findings suggested that the rate of membrane endocytosis of receptor bound rAAV may be a limiting step in transduction. Similarly to BFA, two endosomal protease inhibitors (tripeptides LLnL and Z-LLL) both significantly increased rAAV transduction. These tripeptides have been previously used to increase the transfection efficiency of plasmid DNA and are thought to inhibit the lysosomal degradation of DNA (Coonrod et al., 1997).

The data support the hypothesis that endocytosis and endosomal processing is a key rate-limiting step in rAAV transduction. It appears that actin microfilaments, but not microtubules, are important in rAAV transduction and may act by facilitating rAAV transport to the nucleus. Moreover, cytochalasin B efficiently blocks apical but not basolateral infection of the polarized MDCK cells with influenza virus (Gottlieb et al., 1993). These findings indicate that there is a fundamental difference in the process by which endocytic vesicles are formed at the two surfaces of polarized epithelial cells, and that the integrity and/or the polymerization of actin filaments is required at the apical surface. However, the findings that microtubule depolymerizing agents such as vinblastine did not inhibit rAAV-2 transduction are different than that previously reported for nocodazole inhibition of canine parvovirus (Vihinen-Tanta et al., 1998). Lastly, studies with tripeptide protease inhibitors demonstrated a significant augmentation in rAAV transduction. Such findings suggest that endosomal degradation of virus and/or endosomal release may be an important rate-limiting step in rAAV transduction.

Example 5

Evaluation of Endocytosis and Trafficking to the Nucleus Using Radiolabeled rAAV Radioactively labeled virus provides several unique advantages to Cy3-labeled virus for studies on endocytosis and nuclear trafficking. First, unlike Cy3-labeled virus, no covalent modifications to the virion are needed with $^{35}S$- and $^{3}H$-labeled virus. Hence, aggregation or other unknown effects on trafficking due to covalently attached molecules are not be encountered. Second, by comparing $^{35}S$- and $^{3}H$-labeled virus, the fate of viral capsid proteins and DNA, respectively, can be evaluated. rAV.GFP3ori was labeled by the following protocol: Twenty 150 mm plates of subconfluent 293 cells were infected with Ad.LacZ (5 pfu/cell) for 1 hour followed by calcium phosphate transfection of pCisAV.GFG3ori (250 µg) and pRepCap (750 µg). Cells were incubated for an additional 10 hours at which time media was changed to 2% FBS Methionine-free DMEM for 45 minutes to 60 minutes. The media was then changed again to labeling media containing 15 mCi of $^{35}S$-methionine per 400 ml of 2% FBS Methionine-free DMEM (final=1.49 MBq/ml) and cells were pulsed for 1.5 hours at 37° C. Following labeling pulse, L-methionine was added back to a final concentration of 30 mg/L and cells incubated for an additional 30 hours at 37° C. Cell lysates were prepared and virus was purified. Typical specific activities of labeled virus were $5 \times 10^{-6}$ cpm/particle which is slightly higher than other reports in the field of specific activities of $5.5 \times 10^{-7}$ cpm/particle (Bartlett et al., 1999).

Figure 19:
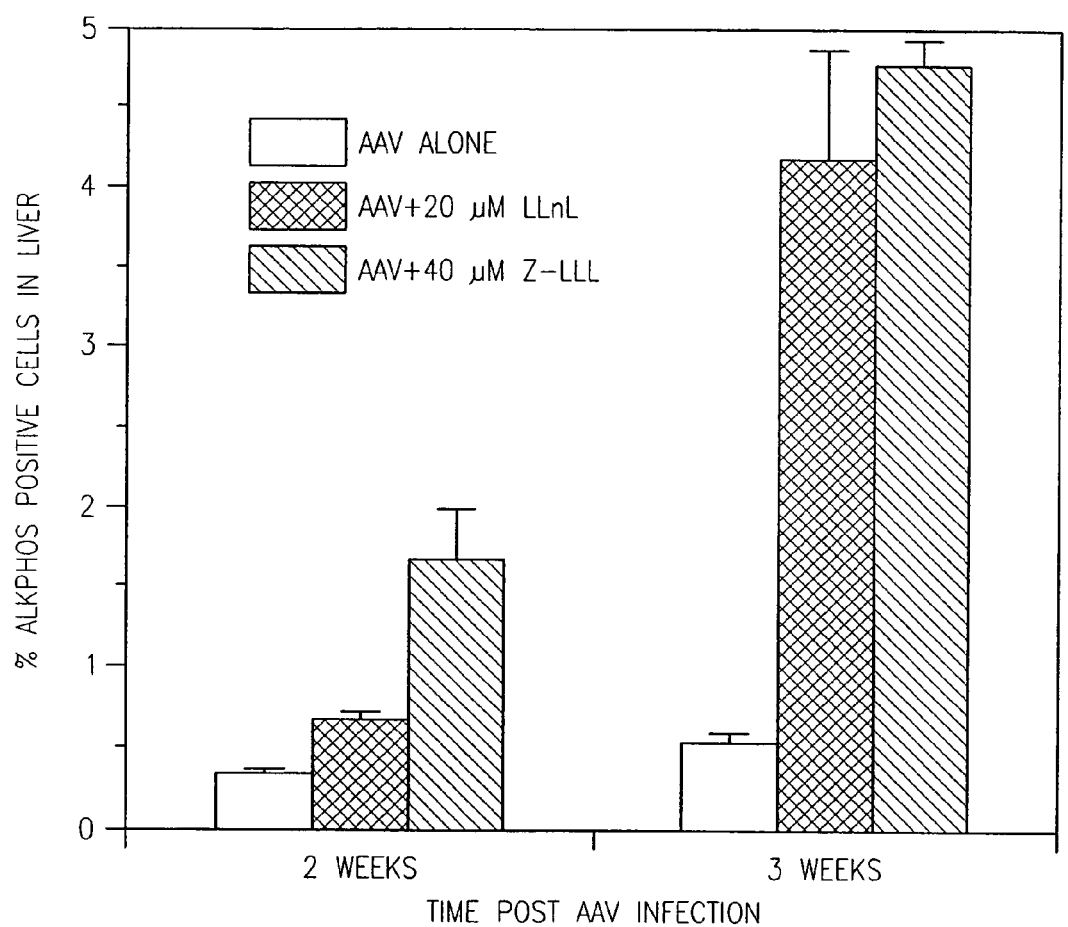
FIG. 19. Co-administration of proteasome inhibitor Z-LLL enhances AAV-mediated gene transfer in mouse liver in vivo. Recombinant AV.Alkphos ($5 \times 10^{10}$ particles) was administered to mouse liver either as virus alone in PBS, virus in combination with 40 µM Z-LLL in PBS, or virus in combination with 200 µM LLnL in PBS. Virus was directly instilled into portal vein of the C57B6 mice. AAV-mediated alkaline phosphatase transgene expression was evaluated by histology staining at 2 and 4 weeks post-infection in frozen tissue sections. The average percentage of the alkphos positive cells in all 6 liver lobes of each individual animal was quantified by NIH image analysis software. The data represents the mean (+/−SEM) of 3 independent mice for each time point in each group.

Results comparing the efficiency by which rAAV traffics to the nucleus in the presence or absence of LLnL are shown in FIG. 19. Cryosections of polarized airway epithelial cells infected with $^{35}S$-labeled AV.GFP3ori (MOI=50,000 particles/cell) from the apical or basolateral sides in the presence or absence of LLnL were overlaid with photographic emulsion and exposed for 5 weeks prior to developing. Photomicrographs in FIGS. 19A and B demonstrate nuclear and cytoplasmic accumulation of virus as indicated by silver grains following basolateral infection in the presence of LLnL. Morphometric analysis of cytoplasmic and nuclear associated silver grains are given in FIG. 19C and demonstrate a significant increase in nuclear trafficking in the presence of LLnL at 2 hours post-infection. Increases in nuclear accumulation of virus were noted in the presence of LLnL following both apical and basolateral infection. Therefore, endocytic rates and nuclear trafficking of virus may be rate limiting in the airway, and these processes were increased by tripeptide protease inhibitors.

Example 6

Endosomal Processing Inhibitors May Increase rAAV Transduction in Polarized Airway Cells Materials and Methods Primary Culture of Human Bronchial Epithelia and Reagents Utilized.

Primary human airway epithelial cells were collected by enzymatic digestion of bronchial samples from lung transplants, as previously described (Kondo et al., 1991; Zabner et al., 1996). Isolated primary airway cells were seeded at a density of $5 \times 10^5$ cells/cm$^2$ onto collagen-coated Millicell-HA culture inserts (Millipore Corp., Bedford, Mass.). Primary cultures were grown at the air-liquid interface for more than 2 weeks, by which time differentiation into a mucociliary epithelium occurs. The culture medium, used to feed only the basolateral side of the cells, contained 49% DMEM, 49% Ham's F12 and 2% Ultraser G (BioSepra, Cedex, France). Dimethyl Sulphoxide (DMSO), camptothecin (Camp), etoposide (Etop), aphidicolin (Aphi), hydroxyurea (HU) and genistein (Geni) were purchased from Sigma (St. Louis, Mo.). Tripeptidyl aldehyde proteasome inhibitors N-Acetyl-L-Leucyl-L-Leucyl-Norleucine (LLnL) and benzyloxycarbonyl-L-leucyl-L-leucyl-L-leucinal (Z-LLL) were purchased from Calbiochem-Novabiochem Corporation (La Jolla, Calif.). Ubiquitin ligase (E3) inhibitors were obtained from Bachem Bioscience Inc. (King of Prussia, Pa.). Anti-AAV capsid monoclonal antibody (Anti-VP1,2 and 3) was purchased from American Research Products (Belmont, Mass.) and anti-ubiquitin antibody was purchased from Santa Cruz Biotechnology Inc. (Santa Cruz, Calif.).

Production of Recombinant AAV Viral Stocks.

Recombinant AAV was produced by a CaPO$_4$ co-transfection protocol and purified through three rounds of isopycnic cesium chloride ultracentrifugation as described above in Example 1. The proviral plasmid pCisAV.GFP3ori is described in Duan et al. (1998). The proviral plasmid pCisRSV.Alkphos, which encodes the alkaline phosphatase reporter gene under the transcriptional control of the RSV promoter and SV40 poly-adenylation signal, was used to generate AV.Alkphos (Yang et al., 1999). The proviral plasmid pCisRSV.LacZ used for AV.LacZ production was generated by first inserting 3474 bp Not I digested β-galactosidase gene (from pCMVβ, Clontech) into the Not I site of the pRep4 (Invitrogene). The entire β-galactosidase expression cassette, including the RSV promoter, β-galactosidase reporter gene and SV40 polyA signal, was excised by Sal I and subsequently cloned into the pSub201 backbone by blunt end ligation (Samulski et al., 1987). Recombinant viral stocks were heated at 58° C. for 60 minutes to inactivate contaminating helper adenovirus. Typical yields were $5 \times 10^5$ to $5 \times 10^9$ particles/µL based on DNA slot blot hybridization assays against plasmid standards. The level of adenoviral contamination, as based on a second reporter assay (Duan et al., 1997) for the recombinant adenovirus used for propagation (Ad.CMVAlkphos for AV.GFP3ori, and Ad.CMVLacZ for AV.Alkphos, Ad.CMVGFP for AV.LacZ), was less than one functional particle per $1 \times 10^{10}$ rAAV particles used for infection of 293 cells in the presence of adenovirus. Transfection with Rep/Cap encoding plasmids served as controls for antibody staining of Rep protein. Virus was dialyzed in PBS prior to in vitro or in vivo infections.

Transduction of Polarized Airway Epithelial Cells and Primary Human Fibroblasts.

rAAV infection of fully differentiated bronchial cells was performed as described in Duan et al. (1998). For infections from the apical surface of the airway cells, 5 µl rAAV was mixed with 50 µl of culture media and applied directly onto the apical compartment of Millicell inserts (MOI=10,000 particles/cell). During apical infection, the basolateral side of the Millicell was continuously bathed in culture media. Gene transfer to the basal side was performed by inverting Millicell inserts and applying viral vector to the bottom of the supporting filter membrane in a 50 µl volume for 2 hours. Subsequently, Millicell inserts were returned to the upright position, in the continued presence of the original viral inoculum plus an additional 450 µl of media. For both apical and basolateral infections, rAAV containing media was removed after 24 hours and replaced with either fresh culture media (for the basal side) or exposed to air (for the apical side). To test the effect of different agents on the efficiency of AAV transduction in polarized airway cells, 1 µl of each solution was mixed with AAV prior to infection of airway epithelia. Agents were usually presented during the 24 hours AAV infection period unless indicated otherwise. Most of the agents were dissolved in DMSO except for hydroxyurea (dissolved in phosphate buffered saline), H-Leu-Ala-OH (dissolved in 0.9% glacial acetic acid) and H-His-Ala-OH (dissolved in 50% methanol). The working concentrations of the agents were as follows: 0.1 µM camptothecin, 10 µM etoposide, 5 µg/ml aphidicolin, 40 mM hydroxyurea, 50 µM genistein, 40 µM LLnL and 4 µM Z-LLL. When the ubiquitin ligase (E3) inhibitors (H-Leu-Ala-OH and H-His-Ala-OH) were used, airway cells were pretreated with a combination of both inhibitors at a final concentration of 2 mM for 60 minutes prior to infection, followed by the continued presence of inhibitor (0.2 mM) during the entire 24 hours infection period from the basolateral surface. Studies involving EGTA treatment were performed by transiently treating the apical membrane of polarized airway epithelia with 3 mM EGTA in water for 10 minutes (Duan et al., 1998). Following hypotonic EGTA treatment, cultures were washed twice with culture medium and infected with rAAV in the presence or absence of 40 µM LLnL. Human primary fibroblast cells (P4) were maintained in 10% fetal bovine serum (FBS), 1% penicillin and streptomycin, and 89% DMEM. Infection with AV.GFP3ori was performed with 80% confluent fibroblasts at an MOI of 1000 DNA particles/cell in 2% FBS DMEM for 24 hours.

$S^{35}$ Labeling of rAAV.

The methionine residue in the capsid protein of rAV.GFP3ori was labeled during the generation of radioactive viral stocks according to a previously published protocol with modifications (Mizukami et al., 1996). Briefly, twenty 150 mm plates of subconfluent 293 cells were infected with Ad.LacZ (5 pfu/cell) for 1 hour followed by calcium phosphate transfection of pCisAV.GFP3ori (250 µg) and pRepCap (750 µg). Cells were incubated for an additional 10 hours, at which time the medium was changed to 2% FBS Methionine-free DMEM for 45 to 60 minutes. The medium was changed once again to labeling medium containing 15 mCi of $S^{35}$-methionine per 400 ml of 2% FBS Methionine-free DMEM (final=1.49 MBq/ml), and cells were pulsed for 1.5 hours at 37° C. Following labeling, L-methionine was added back to a final concentration of 30 mg/L, and cells were incubated for an additional 30 hours at 37° C. Cell lysates were prepared and virus was purified by isopycnic cesium chloride ultracentrifugation as described above. Typical specific activities of labeled virus preparations were $5 \times 10^{-6}$ cpm/particle, which is slightly higher than the $5.5 \times 10^{-7}$ cpm/particle specific activity reported by other investigators (Bartlet et al., 1999).

Viral Binding/Entry Assays and In Situ Localization of Viral Particles.

To assess the binding of rAAV to polarized bronchial epithelia cells, $S^{35}$-labeled AV.GFP3ori was applied to either the apical or basal surface (MOI=50,000 particles/cell), followed by incubation at 4° C. for 60 minutes. Combined binding/entry of rAAV into differentiated airway epithelia was measured under the same conditions, except that the cultures were incubated at 37° C. for an additional 2-24 hours before they were harvested. These combined viral binding/entry assays were performed under identical infection conditions to those used for functional studies of rAAV transduction with transgene expression as an endpoint. After washing three times in PBS, cells were lysed in situ by the addition of 5 ml of liquid scintillation cocktail at room temperature for 5 minutes, and the radioactivity was quantitated in a scintillation counter.

To analyze the subcellular localization of the rAAV particles within polarized human bronchial epithelial cells, infection was performed by applying $S^{35}$ labeled virus (MOI=50,000 particles/cell) to either the mucosal or serosal surface. At 2 hours post-infection, transwells were washed with medium three times and fixed in 4% paraformaldehyde overnight prior to cryoprotection and embedding for frozen sectioning. 10 µm frozen sections were overlaid with photoemulsion and developed for 5 weeks according to a previously published protocol (Duan et al., 1998).

Molecular Analysis of rAAV Viral Genomes Following Infection of Polarized Airway Epithelial Cultures.

The molecular state of bound and endocytosed virus was assayed at different times following rAAV infection. To examine the amount of virus attached to the cell surface, rAAV infection was performed at 4° C. for 1 hour. Following binding, the extent of viral internalization was assessed by continuing incubations in the presence of virus at 37° C. for 4-24 hours. Viral DNA was extracted according to a modified Hirt protocol and Southern blots performed with Hybond N+ nylon membrane (Amersham) (Duan et al., 1997). The 1.6 kb single stranded viral DNA, the 2.7 kb double stranded circular intermediate, and the 4.7 kb double stranded replication from viral genome were detected with a transgene EGFP specific probe at $5 \times 10^6$ cpm/ml. Blots were washed at a stringency of 0.2×SSC/0.1% SDS at 55° C. for 20 minutes twice. In studies aimed at evaluating viral internalization, virus attached to the cell surface was removed by trypsinization with 1 ml of buffer containing 0.5% trypsin, and 5.3 mM EDTA at 37° C. for 10 minutes (500 µl buffer was added to the apical and basolateral compartment of the Millicell inserts), followed by washing with ice-cold PBS twice. Externally bound AAV virus was determined by the intensity of the 1.6 kb viral genome band in Hirt DNA extracted from cells infected at 4° C. for 60 minutes. The internalized virus was determined by the intensity of the 1.6 kb viral genome band in Hirt DNA extracted from trypsinized cells after infection at 37° C. for 4 and 24 hours. The dynamic changes in the molecular structure of the internalized virus were assayed at 2, 10, 30 and 50 days after virus was removed from culture medium.

Detection of Ubiquitinated AAV Capsid Proteins by Immunoprecipitation.

To analyze the effect of the proteasome inhibitor on AAV ubiquitination, human primary fibroblasts were lysed at 6 hours post-viral infection in 1×RIPA buffer. Cell lysates were then cleared with 30 µl Protein A-Agarose. The supernatant was incubated with 10 µl of monoclonal anti-VP1, 2, and 3 antibody (Clone B1, ARP) followed by the addition of 30 µl Protein A-Agarose. The pellets were washed 4 times with IX RIPA buffer and resolved on a 10% SDS-PAGE. After transfer to a nitrocellulose filter, blots were probed with a 1:1000 dilution of anti-ubiquitin monoclonal antibody (clone P4D1, Santa Cruz, catalogue #sc-8017), followed by 1:500 HRP-conjugated secondary antibody (BMB). After the final washings, immunoreactivity was visualized using the ECL system (Amersham).

In Vivo Studies in Mice.

Animal studies were performed in accordance with the institutional guidelines of the University of Iowa. To determine the effect of the proteasome inhibitor on AAV mediated gene transfer in mouse lung, 6 week-old BALB/c mice were lightly anesthetized using a methoxyflurane chamber. AV.LacZ ($5 \times 10^{10}$ particles) was administered alone or with 400 µM Z-LLL in a 10 µl instillation by nasal aspiration as described by Walters et al. (2000). To prevent unforeseen toxicity of DMSO solvent, the proteasome inhibitor Z-LLL was dissolved in ethanol as a 40 mM stock solution and was included in the viral inoculum at 1% final concentration. Viral infection controls in the absence of Z-LLL also contained a 1% final concentration of ethanol. Since studies in both primary cultured human airway cells and fibroblasts have demonstrated similar enhancement efficiency between 40 µM LLnL and 4 µM Z-LLL, and also due to the poor solubility of LLnL in ethanol (Example 7 employed a low dose of LLnL in DMSO which was administered to the trachea), only Z-LLL was tested in this particular mouse lung study. The animals were euthanized at 2, 10 and 150 days post infection and PBS (10 ml) was instilled into the right ventricle, followed by removal of the lungs and heart as an intact cassette. The trachea was intubated and instilled at 10 cm of water pressure with the following solutions in order: PBS, 0.5% glutaraldehyde, 1 mM $MgCl_2$/PBS, and finally X-gal staining reagent for an overnight incubation at room temperature. The X-gal stained mouse lungs were then post fixed in 10% neutral buffered formalin for 48 hours at room temperature and cryopreserved in serial 10%, 20% and 30% sucrose/PBS solutions. Lungs (N=3 for each condition) were embedded in OCT (optimal cutting temperature; Baxter, Warrendale, Pa.) and 15 µm serially sections were analyzed for gene transfer by calculating the percentage of positive cells in the airway epithelium. The diameter of the airway was recorded for classification (>360 µm, 260-350 µm, 160-250 µm, <150 µm) of results following morphometric analysis. Greater than 150 airway cross-sections were quantified for each experimental condition.

Results

Molecular Analysis of rAAV Genomes in Polarized Airway Epithelia.

Figure 8:
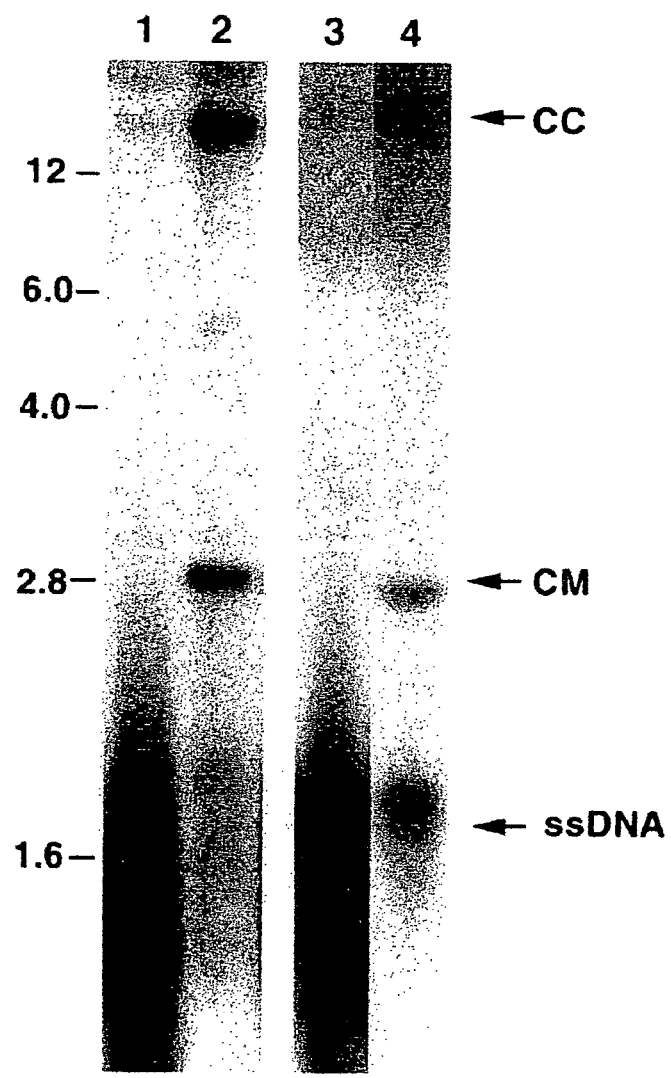
FIG. 8. Southern blot analysis of AAV genomes in polarized airway epithelia. Differentiated human bronchial epithelial cultures were infected with AV.GFP3ori at an moi of 10,000 particles/cell from either the apical (lanes 1 and 3) or basolateral (lanes 2 and 4) surface. Fifty days after infection, Hirt DNA was harvested and electrophoresed in a 1% agarose gel. Each lane represents combined Hirt DNA from two transwell cultures and the two gels are derived from two independent tissue samples. The Southern blot was hybridized to a P$^{32}$-labeled EGFP probe and exposed to film for 48 hours. Molecular weight standards are marked to the left of the autoradiogram. The single stranded and circular monomer forms of AAV viral DNA migrate at 1.6 kb and 2.8 kb, respectively. ssDNA, single stranded viral DNA; CM, circular monomer, CC circular concatamer. Circular intermediates in polarized airway epithelia.

Recent studies revealed a lack of AAV-2 receptor, heparin sulfate proteoglycan, and co-receptors, FGFR-1 and αVβ5 integrin, at the apical surface of differentiated airway epithelia (Duan et al., 1998; Duan et al., 1999; Hughes et al., 1993; Goldman et al., 1999). However, differences in the binding of radioactive virus at the apical and basolateral membranes were only 4-7 fold (basolateral>apical) (Duan et al., 1998). These differences in binding are insufficient to explain the 200-fold variance observed in the polarity of infection (basolateral>>apical) with rAAV-2 (Duan et al., 1998). These findings suggested that viral binding and/or uptake were not the sole limiting factors contributing to inefficient mucosal transduction in airway epithelia To this end, the molecular state of rAAV DNA at 50 days following apical and basolateral infection of air-liquid interface cultured human bronchial epithelia was evaluated. At this time point, gene expression measured from an EGFP reporter was >200-fold higher in basolaterally infected cultures (data not shown) (Duan et al., 1998). Hirt DNA from the cultures was evaluated by Southern blot hybridization with $^{32}$P-labeled EGFP probes. As shown in FIG. 8, a significant amount of apically applied rAAV was able to infect airway cells. However, only single stranded viral genomes (ssDNA) were detected at this time point (50 days). This result clearly suggests that rAAV can be endocytosed from the mucosal surface and that the endocytosed viral ssDNA was stably sequestered in some unknown subcellular compartment. In contrast, the majority of basolaterally applied rAAV was converted into double stranded forms that migrated at 2.8 kb and >12 kb in 1% non-denaturing agarose gels (FIG. 8). Consistent with previous reports (Sanlioglu et al., 1999; Duan et al., 1999), subsequent restriction enzyme mapping of Hirt DNA and Southern blots confirmed this 2.8 kb band to be a supercoiled, circular episomal molecule (data not shown). The identity of the >12 kb band, which is significantly more intense following basolateral infection, is currently unknown but may represent episomal circular concatamers of the AAV genome. Taken together, these results suggest that inefficient molecular conversion of AAV viral DNA to circular genomes represents a significant obstacle for rAAV mediated gene transfer from the apical surface of the airway. Furthermore, circularization, not linear replication though self-priming, is the predominant pathway for rAAV gene conversion in polarized airway epithelia.

Proteasome Inhibitors Dramatically Enhance rAAV Infection in Polarized Airway Epithelia.

Figure 9:
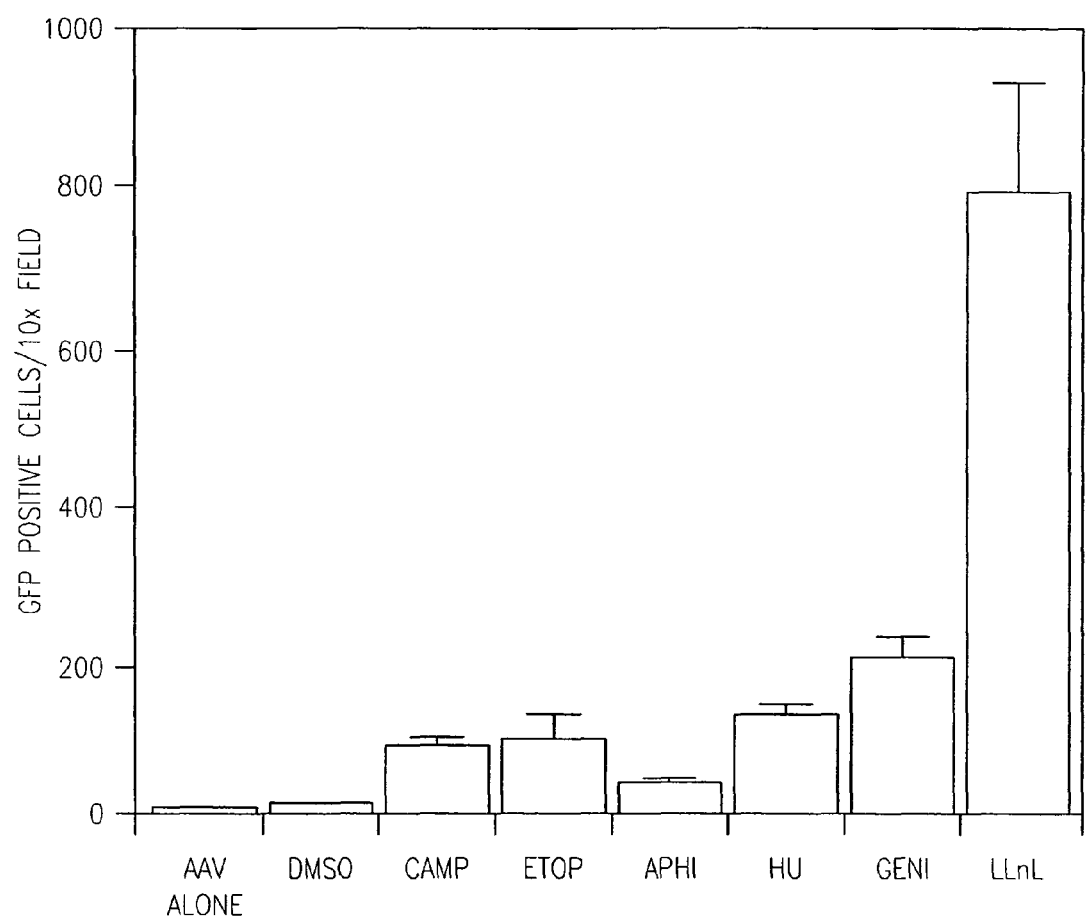
FIG. 9. Effects of different agents on AAV transduction from the basal surface of polarized bronchial epithelia. Fully differentiated human bronchial airway epithelia were treated with the indicated agents at the time of AAV infection (MOI=10,000 particles/cell) from the basolateral surface. Camp: camptothecin at 0.1 μM; Etop: etoposide at 10 μM; Ahpi: aphidocolin at 5 μg/ml; HU: hydroxyurea at 50 mM; Geni: genistein at 50 μM; LLnL was used at 40 μM. Since most of the tested agents (except for hydroxyurea) were dissolved in DMSO, a vehicle control of 1% (vol/vol) DMSO was also performed to exclude the possibility of a non-specific effect. GFP expression was monitored at 48 hours post-infection by counting the number of GFP positive cells per 10 random 10× fields in the culture dishes. The data represent the mean+/−SEM of three independent infections for each tested chemical.

Given the fact that rAAV appears to remain latent within some cellular compartment(s) following apical infection in the airway, and that agents that alter the molecular conversion of the viral genome might enhance rAAV transduction in airway epithelia, several agents were tested in this regard, including DNA damaging agents (Alexander et al., 1994), DNA synthesis and topoisomerase inhibitors (Russell et al., 1995), and cellular tyrosine kinases inhibitors (Qing et al., 1997; Man et al., 1998). Application of camptothecin, etoposide, hydroxyurea, and genistein resulted a 10 to 60 fold enhancement in rAAV transduction from the basolateral surface (FIG. 9). Interestingly, however, none of these agents facilitated rAAV transduction from the apical surface (data not shown). Since chemicals known to affect intra-nuclear events involved in rAAV transduction in other cell types (Sanlioglu et al., 1999) did not enhance rAAV apical infection in the airway, other agents affecting endocytic processing, such as the ubiquitin-proteasome pathway, were tested. Proteasome systems are known to modulate the intracellular processing of many foreign and endogenous molecules, including viruses such as HIV (Schwartz et al., 1998). Several specific, cell permeable, peptide aldehyde inhibitors of proteasome pathways have recently been discovered (Rock et al., 1994; Fenteany et al., 1995). These inhibitors bind to the active sites of proteolytic enzymes within the proteasome core and reversibly block their function (Rubin et al., 1995). To test whether proteasomes represent an intracellular compartment that sequesters rAAV following infection, the tripeptidyl aldehyde proteasome inhibitor (a cysteinprotease inhibitor) N-acetyl-L-leucinyl-L-leucinal-L-norleucinal (LLnL, also called Calpain inhibitor I) was applied to polarized cultures of human bronchial epithelial cells at the time of rAAV infection. Surprisingly, a greater than 200 fold augmentation in transgene expression was obtained at 2 days post infection when 40 µM LLnL was applied to the serosal surface along with rAAV (FIG. 9). A similar result was achieved when another ubiquitin-proteasome pathway inhibitor, N-carbobenzoxyl-L-leucinyl-L-leucinyl-L-leucinal (Z-LLL, also called MG132) (Jensen et al., 1995), was tested (data not shown). However, the most important finding was that these proteasome inhibitors also substantially increased rAAV transduction from the mucosal surface (see below). When compared with other agents, proteasome inhibitors were found to be the most potent enhancers of rAAV transduction in airway epithelium.

Proteasome Inhibitors Augment rAAV Transduction in Airway Epithelia in a Polarized Fashion.

Figure 7A:
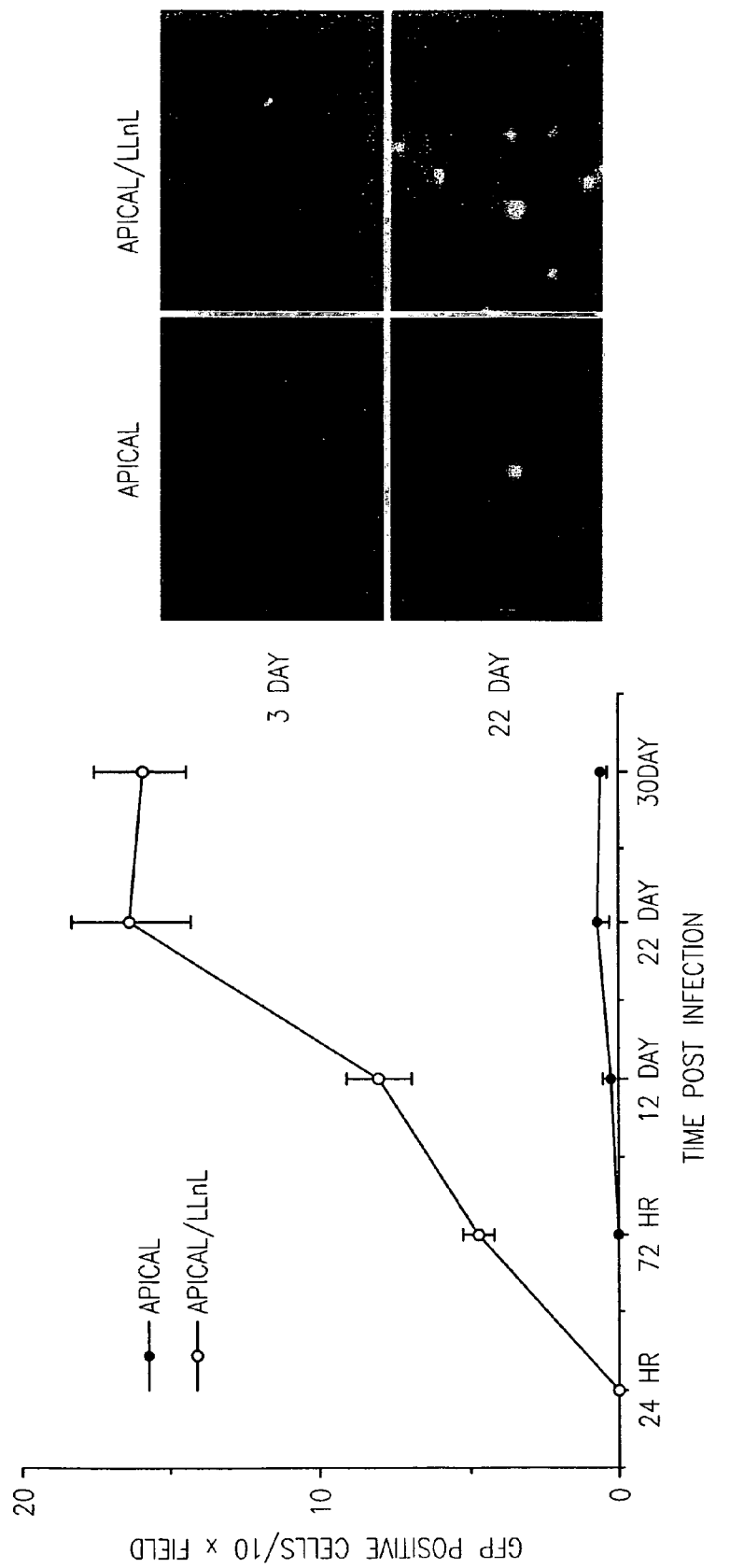
FIG. 7. Proteasome inhibitors differentially augment rAAV transduction from the apical or basolateral surfaces of airway epithelia The efficiency and time course of rAAV transduction were evaluated in polarized airway epithelial cultures following infection with rAV.GFPori3 (MOI=10,000 particles/cell) in the presence or absence of 40 μM LLnL. Transgene expression was monitored by indirect fluorescence microscopy at the indicted time points by quantifying the mean number of GFP positive cells per 10× field (mean+/−SEM of 3 independent samples for each time point). The effect of LLnL treatment was compared between matched sets of tissue samples at each time point following infection from the apical (Panel A) or basolateral (Panel B) surfaces. The photomicrographs on the right side of each panel illustrate representative 20× fields for the 3 and 22 day post-infection time points.
Figure 7B:
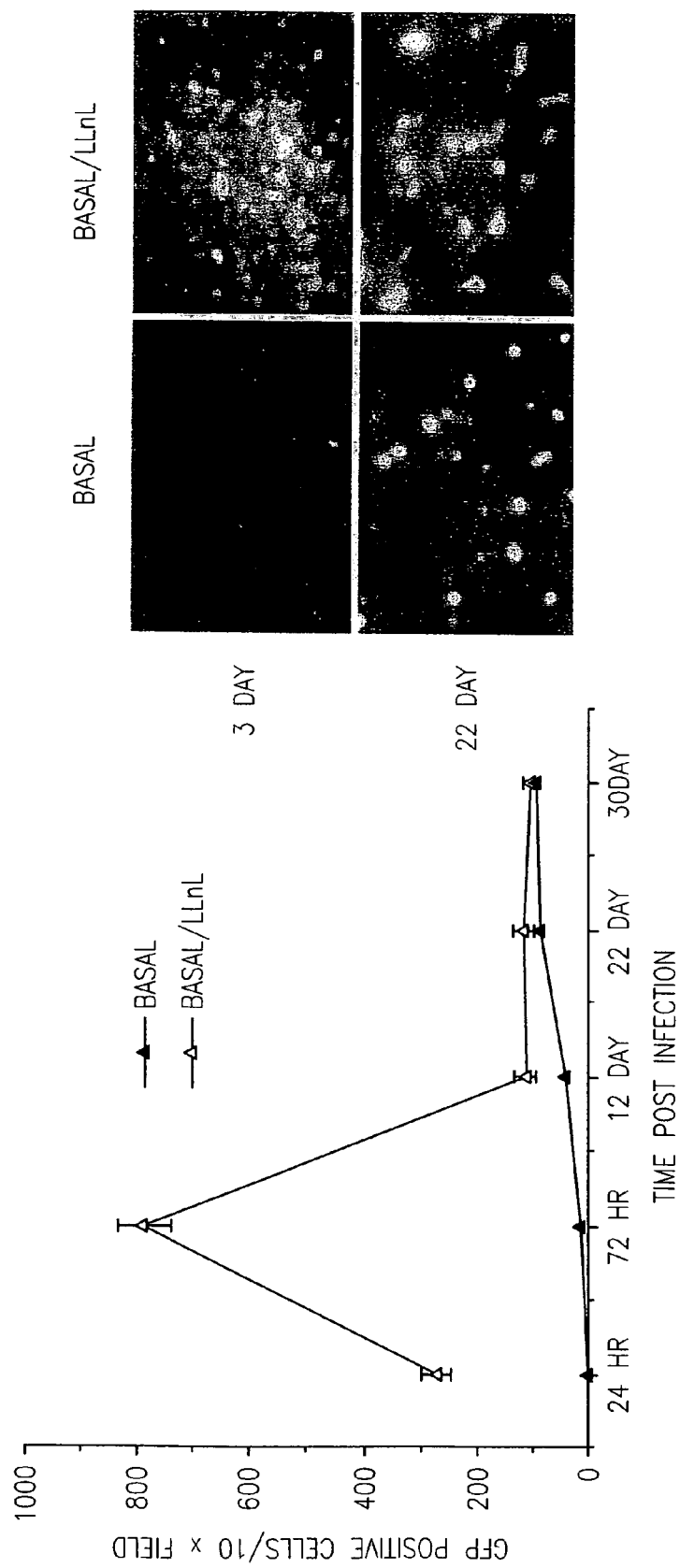

Although proteosome inhibitors appear to significantly increase the efficacy of rAAV transduction from the serosal surface, the route most germane to clinical application of gene delivery in the airway is the mucosal surface. To test the effect of proteasome inhibitors on rAAV transduction from apical membrane, a side-by-side kinetic comparison of rAAV transduction from both mucosal and serosal surfaces of airway epithelia following treatment with LLnL was performed. As shown in FIG. 7A, co-administration of LLnL and rAAV to the mucosal surface resulted a sustained augmentation in AAV transduction, which peaked at 22 days post-infection. In contrast to mucosal infection, rAAV infection from the serosal surface in the presence of LLnL resulted only in a transient peak in gene expression at 72 hours post-infection, which returned to the levels equivalent to that of the untreated samples by 22 days (FIG. 7B). These results suggested that the proteasome inhibitor LLnL produces different augmentation profiles when AAV virus is applied to either the apical or the basolateral membranes. To exclude potential effects caused by polarized uptake of LLnL by airway epithelia, different combinations of rAAV and LLnL administration from both apical and basolateral surfaces were tested. Similar augmentation patterns for AAV transduction were achieved, regardless of whether LLnL was applied to the same or opposite surface as rAAV during infections (data not shown).

Figure 10:
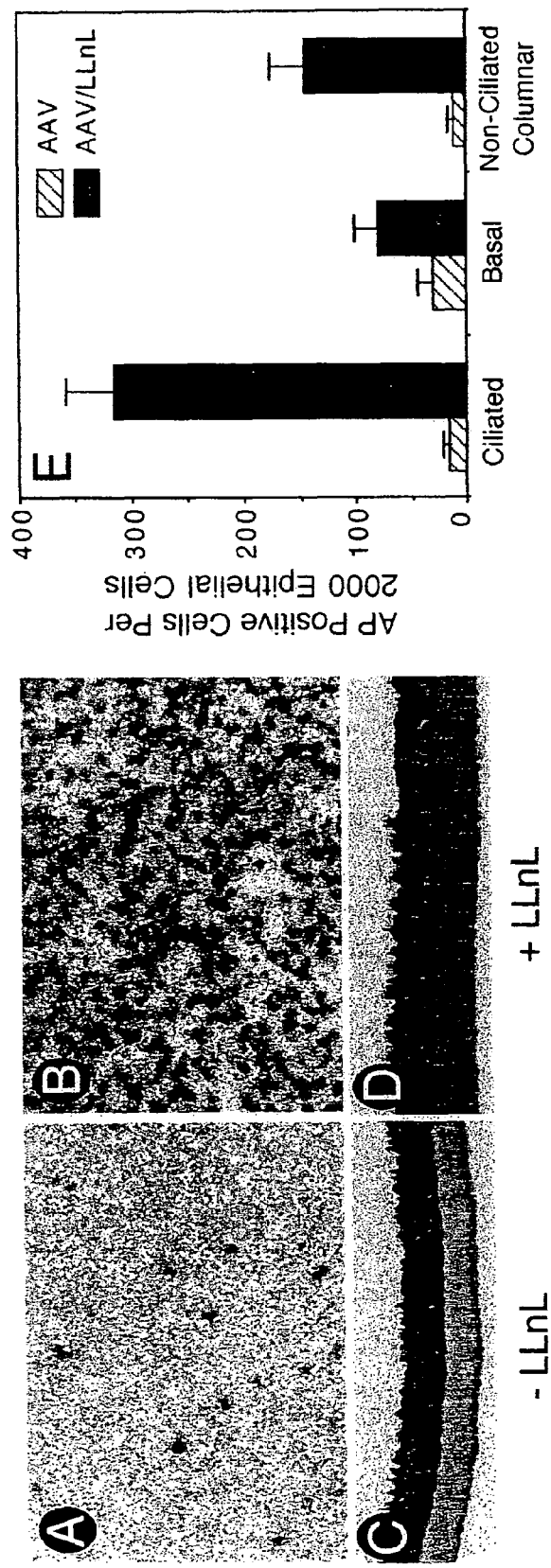
FIG. 10. The proteasome inhibitor LLnL preferentially induces AAV transduction in ciliated cells. The cell types transduced by AAV were examined by alkaline phosphatase staining 3 days following basolateral infection of polarized epithelial cultures with AV.Alkphos infection (MOI=10,000 particles/cell) in the presence of or absence of 40 μM LLnL. En face photomicrographs in panels A (without LLnL) and B (with LLnL) depict enhanced rAAV transduction in the presence of LLnL. 8 μm paraffin sections were used to histologically quantify the types of cells transduced. Three classifications were used, ciliated cells (with alkphos expression localized to the apical membrane and cilia), basal cells residing in the lower half of the epithelium with no contact with the lumen, and non-ciliated, columnar cells. Panel C (without LLnL) and D (with LLnL) show representative neutral red counter-stained cross-sections for each condition. The numbers of alkphos stained cells/2000 epithelial cells for the various cell types transduced by AAV are presented in panel E (mean+/−SEM from three independent Millicell insert samples).

To determine whether LLnL administration augmented rAAV transduction of particular airway cell types, a rAAV vector encoding the alkaline phosphatase gene (Alkphos) was utilized. Transduced cell types were evaluated by standard histochemical staining for Alkphos to address this question. In the absence of LLnL, rAAV preferentially transduced basal cells at 3 days following serosal application of virus (FIGS. 10A and C). Consistent with previous findings utilizing AV.GFP3ori virus, co-administration of LLnL resulted in a dramatic increase in AV.Alkphos transduction (FIGS. 10B and D). Interestingly, ciliated cell transduction was most significantly increased by treatment with LLnL at the time of rAAV infection (FIG. 10E). In contrast, basal cells were the least responsive to LLnL treatment. These findings indicated that the mechanisms of LLnL action may have some cell specific components, which differs in polarized (i.e., ciliated) and non-polarized (i.e., basal) cell types.

Optimization of LLnL Enhanced rAAV Transduction.

Figure 11A:
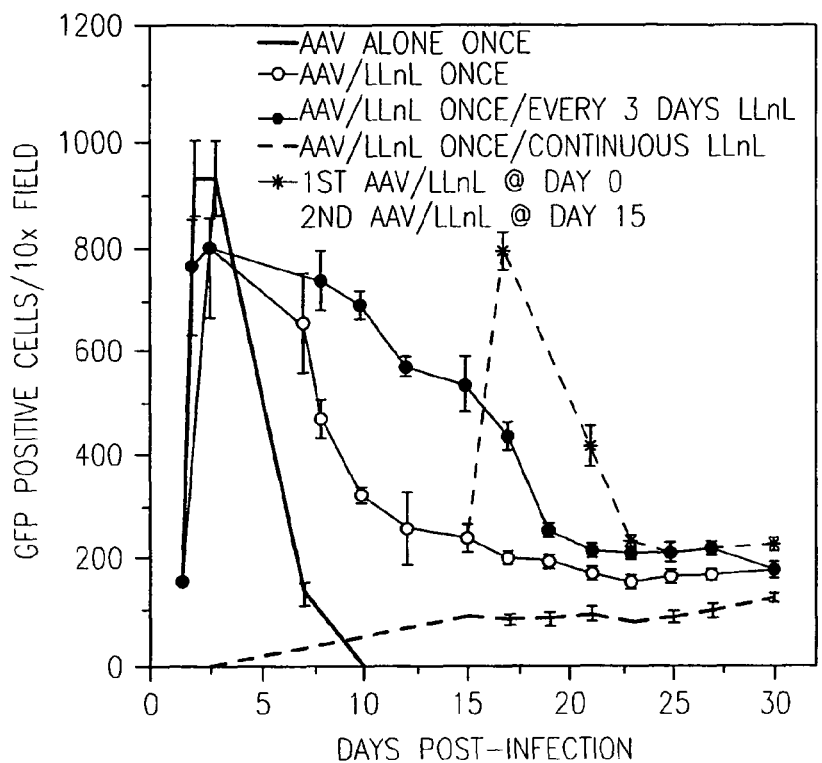
FIG. 11. Optimization of LLnL-enhanced transduction in polarized bronchial epithelia. Differentiated transwell cultures were infected with AV.GFP3ori (10,000 particles/cell) from either the basolateral (Panel A) or the apical (Panel B) surface with the indicated treatments involving LLnL and/or EGTA. All infections were carried out for 24 hours and GFP transgene expression was monitored by indirect fluorescent microscopy at the indicated times. Data represent the mean (+/−SEM, N=6) for each experimental condition. Experiments were performed in triplicate on transwells derived from samples obtained from two different patients. The following conditions were evaluated for basolateral infection in Panel A: 1) single infection with AV.GFP3ori alone (black line), 2) single infection with AV.GFP3ori in the presence of 40 μM LLnL (solid purple line), 3) single infection with AV. GFP3ori in the presence of 40 μM LLnL followed by repeated 5 hour exposure to 40 μM LLnL in the basal compartment culture medium every 3rd day thereafter (solid red line), 4) single infection with AV.GFP3ori in the presence of 40 μM LLnL followed by the continued exposure to 40 μM LLnL in the basal medium after rAAV was removed (solid green line), and 5) repeated infection with AV.GFP3ori on day 1 and 15 in the presence of 40 μM LLnL for 24 hours at the time of infection (dashed blue line). The following conditions were evaluated for apical infection in Panel B: 1) single infection with AV.GFP3ori alone (solid black line); 2) single infection with AV.GFP3ori following pretreatment with 3 mM hypotonic EGTA prior to the viral infection (solid purple line); 3) single infection with AV.GFP3ori in the presence of 40 μM LLnL (solid green line); and 4) single infection with AV.GFP3ori in the presence of 40 μM LLnL following pretreatment with 3 mM hypotonic EGTA prior to the viral infection (solid red line).

With the aim of further improving the enhancement in rAAV transduction achieved in the presence of LLnL, several detailed kinetic studies were performed which altered the timing and number of LLnL administrations following rAAV infection (FIG. 11). Several important conclusions arose from these studies. First, following basolateral infection, administration of LLnL once every three days increased length of peak transgene expression, despite the fact that by the end of 30 days levels were similar to that of cultures treated once at the time of infection. Second, continual administration of LLnL was toxic to cells and ablated transgene expression by 10 days. Third, re-infection of cultures with rAAV in the presence of LLnL at 7, 10 and 15 days resulted in a similar pattern of augmentation and, as expected, elevated the final level of transgene expression observed at 30 days (only data from the second infection at 15 days are shown). Most notably however, all the cultures infected from the basolateral side produced similar long-term transgene expression levels within 2 to 3 fold of each other, regardless of whether LLnL was administered.

Figure 11B:
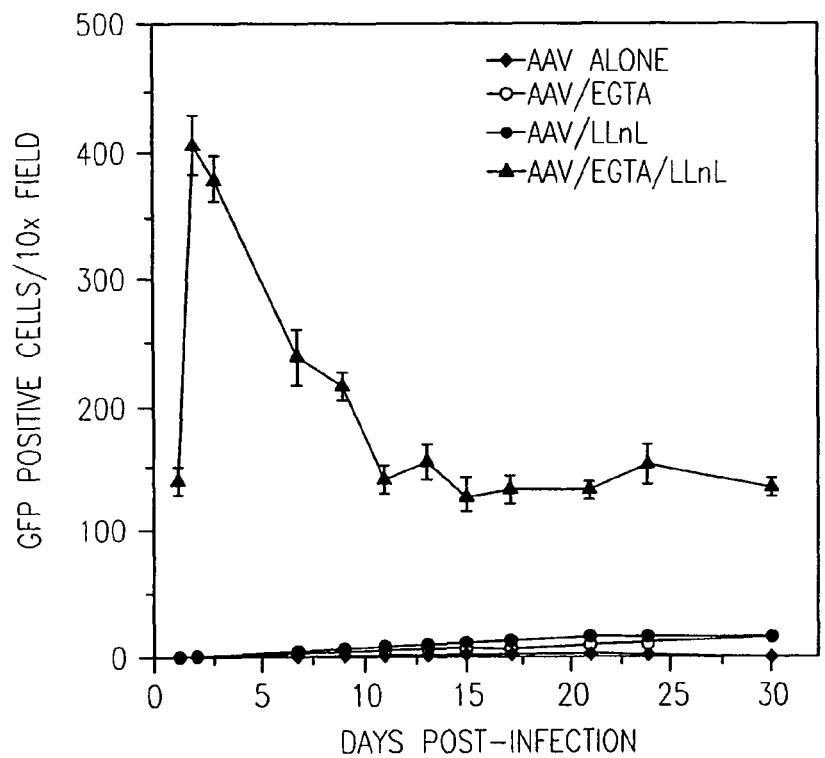

Despite the fact that LLnL administration at the time of the viral infection augmented rAAV transduction from both the apical and basolateral surfaces, the kinetics of this induction were significantly different. Enhancement following basolateral infection was transient, while enhancement following apical infection was long-term (FIG. 7). Furthermore, although induction with LLnL from the apical membrane was long-lasting, by 30 days the maximal level of transgene expression was only one eighth of that resulting from basal infection (FIG. 7A). The application of hypotonic EGTA solution has been shown to increase AAV transduction from the apical surface by 7 to 10 fold (Duan et al., 1998; Walters et al., 2000). Therefore the combined administration of EGTA and LLnL could provide yet a further increase in rAAV transduction from the apical surface. Interestingly, treatment of airway cultures with EGTA prior to infection with rAAV in the presence of LLnL gave a transient peak in transduction within the first three days, and a significantly increased (200-fold), prolonged level of transgene expression out to 30 days (FIG. 11B). This prolonged level of transgene expression, while comparable to rAAV infection from the basal surface, was much above the level observed in apically infected epithelia treated with EGTA alone (FIG. 11B). In summary, these results demonstrate that EGTA and LLnL have synergistic effects on rAAV transduction, allowing for transduction from the apical surface at levels normally only seen following basolateral infection.

Viral Binding and Internalization are not Affected by LLNL Treatment.

Figure 12A:
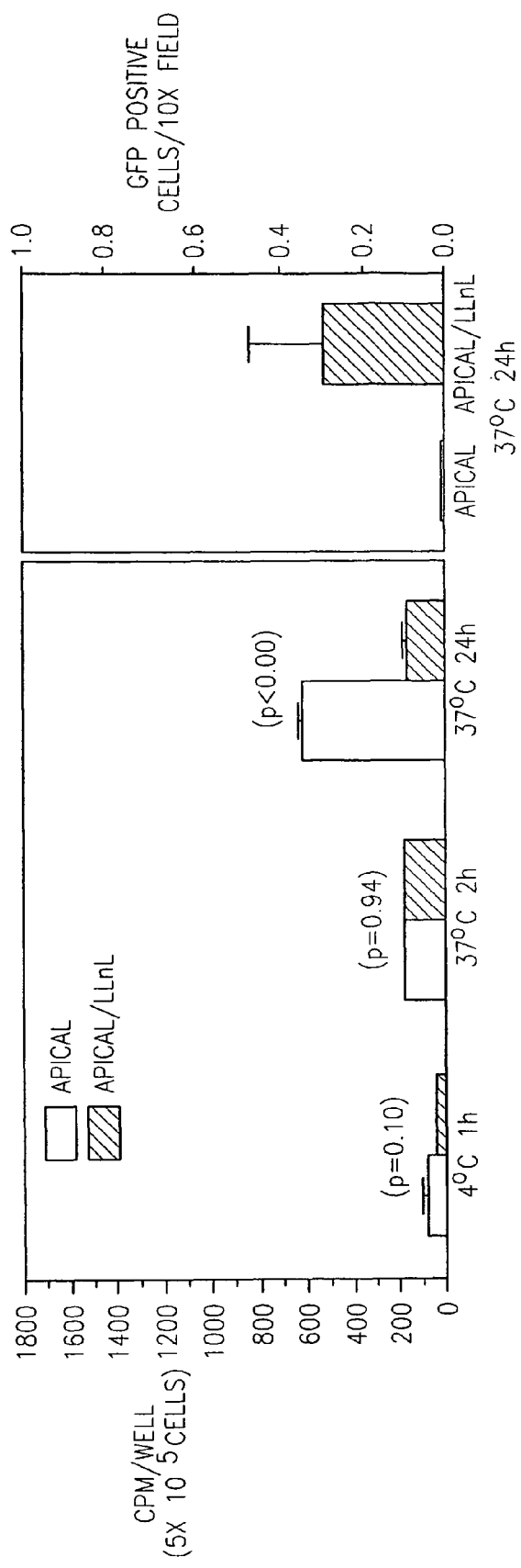
FIG. 12. Binding and uptake of $S^{35}$-labeled AV.GFP3ori in fully differentiated human bronchial epithelia. The ability of polarized bronchial epithelia to bind and internalize virus from the apical or the basolateral surfaces was quantified using $S^{35}$-labeled rAAV. The binding assay was performed after incubation with virus at 4° C. for 1 hour, followed by repeated washing in PBS. The combined bound and internalize virus was quantified following incubation with virus at 4° C. for 1 hour, and subsequent incubation at 37° C. for 2 hours and 24 hours. Non-specific background binding of radiolabeled virus was determined in parallel studies on collagen coated empty chambers not seeded with bronchial cells. Background counts (averaging 15.67+/−5.17 cpm/well) were subtracted from experimental sample counts prior to analysis. Data in the right side of each panel is presented as the net cpms of bound/internalized virus (raw counts minus background counts of empty transwells). The results represent the mean (+/−SEM) of 6 independent transwells for each condition. Experiments were performed in triplicate from two independent tissue samples. The significance of the differences between each pair of samples (with or without LLnL) was evaluated using the Student's t-test and p-values are provided in brackets above the data for each condition. To correlate uptake of radioactive virus with the functional expression the rAAV encoded transgene, GFP expression from the same set of samples was quantified at 24 hour post-infection by indirect fluorescent microscopy. The results (Mean+/−SEM, N=6) are presented as a bar graph on the right side of each panel.
Figure 12B:
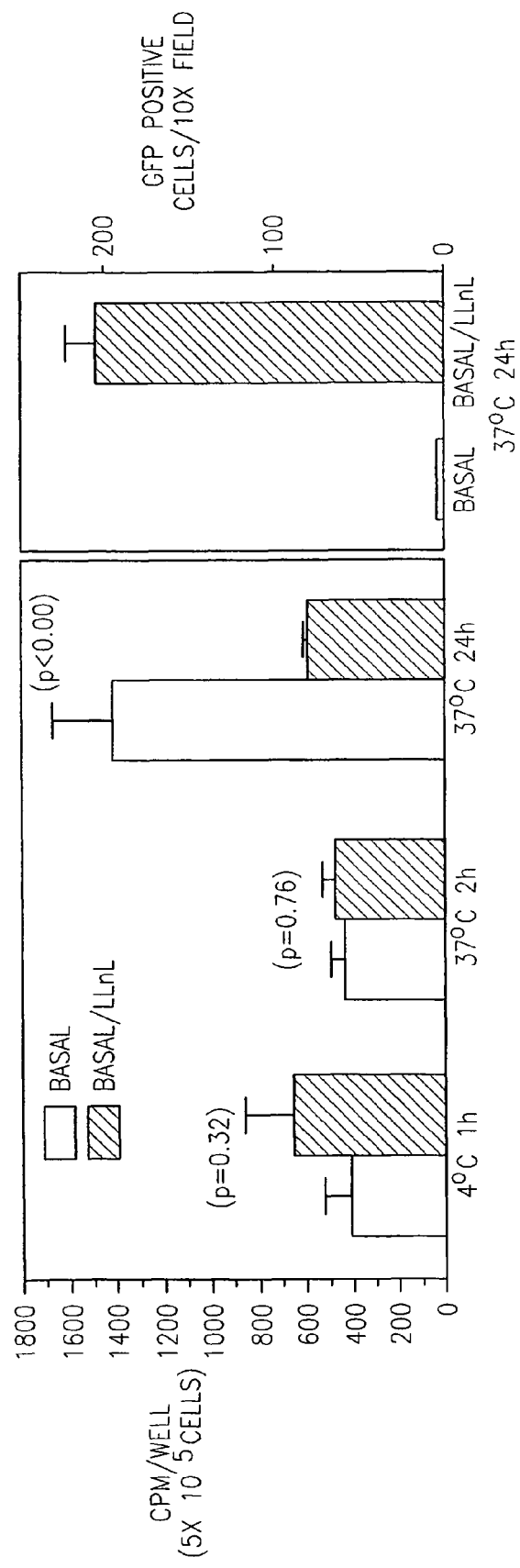

The action of LLnL has been typically attributed to it selective and reversible inhibition of the proteasome system. However, it was important to rule out any possible effect on viral binding and/or endocytosis. As has been found for type 1 herpes simplex virus (Everett et al., 1998), LLnL treatment had no significant effect on 4° C. rAAV binding (FIG. 12). Similarly, the uptake of $S^{35}$ labeled rAAV for a 2 hour infection period at 37° C. was not altered by LLnL treatment (FIG. 12). Given these results, LLnL acts at points distal to virus binding and entry. Interestingly, at 24 hours post-infection a very significant decrease in the amount of intracellular radioactivity was observed in epithelia treated with LLnL, regardless of which surface was infected (FIG. 12). Given the concordant increase in transgene expression at this time point FIG. 12), LLnL may be accelerating processing and routing of the virus to the nucleus, wherein uncoating and clearance of $S^{35}$ labeled capsid proteins occur. By this mechanism, $S^{35}$ isotope would be diluted into the culture medium and could explain the decrease in cell-associated counts.

LLnL Enhances Endosomal Processing and Nuclear Trafficking of rAAV.

Figure 13:
FIG. 13. In situ localization of rAAV in the polarized airway epithelia using $S^{35}$ labeled virus. Polarized human airway epithelia were infected with $S^{35}$-labeled virus (MOI=50,000 particles/cell) from either the apical or basolateral side (+/−LLnL). At 2 hours post-infection, transwells were washed with media three times and fixed in 4% paraformaldehyde overnight prior to cryoprotection in sucrose and OCT embedding. 10 μm frozen sections were overlaid with photoemulsion and developed after 5 weeks of exposure. Panel A depicts the typical localization pattern following basolateral infection in the presence of LLnL. Arrows indicate nuclear-associated virus. Panel B presents enlargements of boxed regions in Panel A. Blinded morphometric quantification was performed by counting the number of nuclear-associated and cytoplasmic radioactive grains of 10 random fields, as shown in Panel A. A total of 60 cells was quantitated per field, to give a total of 600 cells per sample and 2400 cells per condition. Results in Panel C are the mean+/−SEM of four independent samples for each condition.
Figure 13:
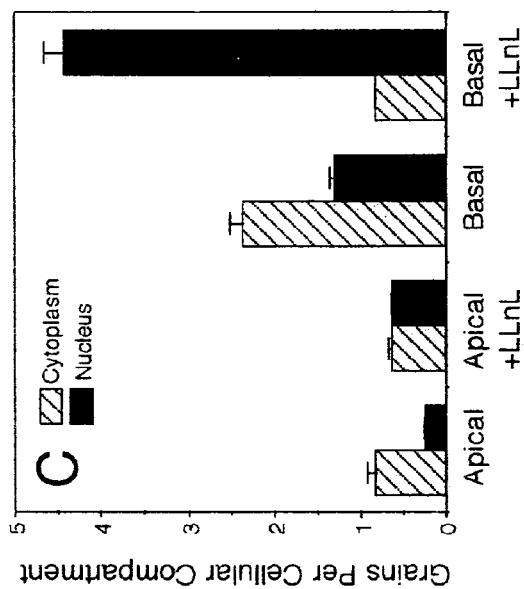

To test the hypothesis that LLnL increases trafficking of rAAV to the nucleus, in situ localization of the $S^{35}$-labeled rAAV particles following infection from the apical and basolateral surfaces was performed in the presence and absence of LLnL. Since loss of intact radiolabeled capsid proteins occurred at 24 hours post-infection, a 2 hour time point was chosen for this analysis. Using photoemulsion overlay, the subcellular distribution of $S^{35}$-labeled rAAV particles was evaluated by blinded morphometric analysis. As shown in FIG. 13, the majority of viral particles localized to the cytoplasm in the absence of LLnL. This was the case regardless of whether infection was performed from the apical or basolateral surface. In contrast, LLnL treatment substantially changed the intracellular distribution of radiolabeled rAAV particles, resulting in a significant shift to nuclear associated grains. These results substantiated the findings from whole cell counts at 24 hours post-infection, which suggested that LLnL increases viral uncoating and the subsequent loss of $S^{35}$ isotope into the media.

LLnL Augment rAAV Transduction within a Specific Time Frame after Infection.

Figure 14:
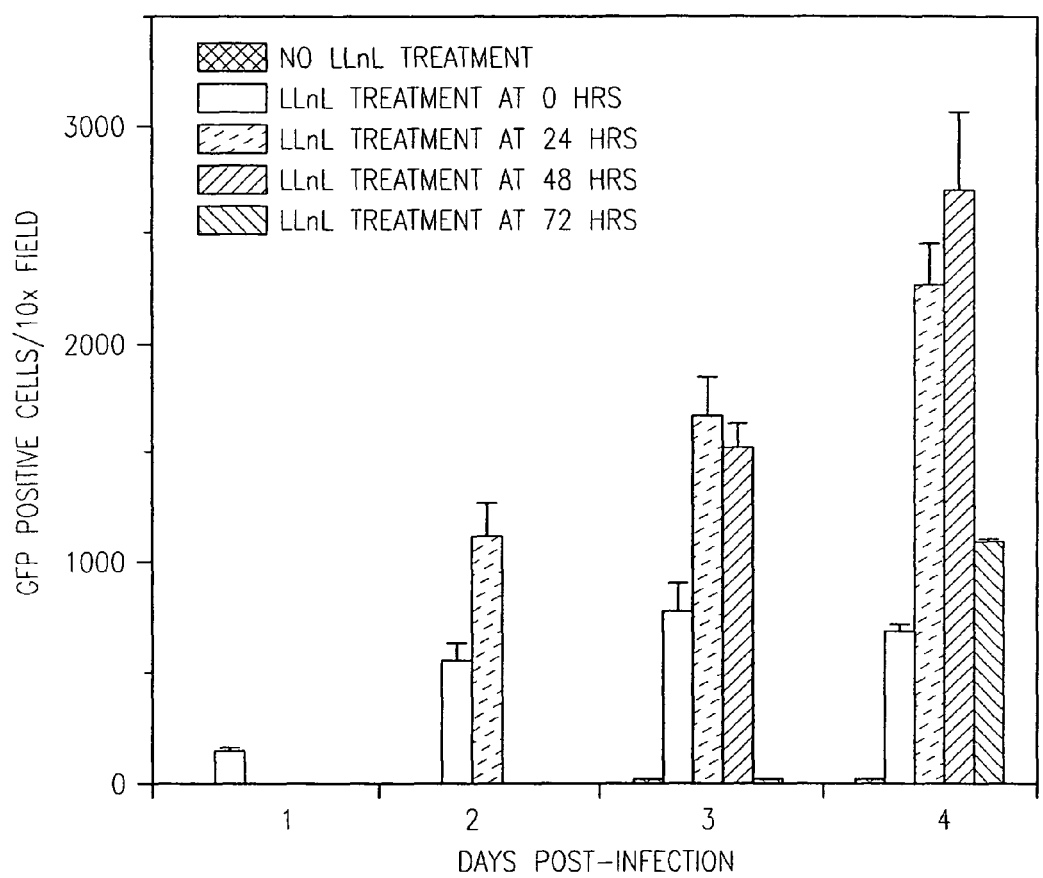
FIG. 14. LLnL induces rAAV transduction within a specific time frame after infection. To study the kinetic effects of LLnL administration on AAV transduction, the proteasome inhibitor LLnL was added to the culture medium at different times following rAAV infection from the basolateral surface of airway epithelia. All cultures where infected with AV.GFP3ori (10,000 particles/cell) at 0 hours. 40 μM LLnL was added at the time of infection (0 hours), or at 24 hour intervals after infection (24, 48, and 72 hours). The baseline of AAV transduction in the absence of LLnL treatment is also shown. GFP expression was quantified at 1, 2, 3, and 4 days post-infection using indirect fluorescent microscopy and is presented as GFP positive cells per 10× field. The date in each panel represents the mean (=/−SEM) from 3 independent samples. The immediate increase in rAAV mediated transgene expression after addition of LLnL is consistent with the hypothesis that LLnL acts by enhancing endosomal processing of viral particles from the cytoplasm to nucleus where it can be expressed. Furthermore, the addition of LLnL at 2-3 days post-infection gave rise to higher levels of transgene gene expression than application of LLnL at the time of infection. These results support the notion that viral binding and internalization are not likely the steps enhanced by LLnL.

Evidence thus far has suggested that LLnL may act to increase intracellular routing of rAAV to the nucleus. Additionally, LLnL action is independent of the epithelial surface to which it is administered (i.e., serosal application of LLnL augments mucosal infection and vice versa). This indicates that LLnL need not be endocytosed with AAV particles to enhance transduction. Thus, LLnL may act at a specific time following rAAV endocytosis but during endosomal processing. To provide functional support for this hypothesis, a kinetic analysis of LLnL action at various times after infection from the basolateral surface was performed. In these experiments, LLnL was added to the culture medium either at the time of AAV infection or at various time points after infection. Viral-mediated transgene expression was quantified at 24 hour intervals following infection. Augmentation was achieved regardless of whether LLnL was administrated at 0, 24, 48, and 72 hours after viral infection. However, addition of LLnL at 24 or 48 hours gave the strongest level of augmentation. The ability of LLnL to reduce AAV expression appeared to decline by 72 hour post-infection (FIG. 14) and was completely lost by 15 days after the initial AAV infection (data not shown). Taken together, it appears that after rAAV enters the cell, it may be targeted to an intracellular compartment that is sensitive to proteasome inhibitor-facilitated liberation. In addition, the loss of an LLnL augmentation effect at 15 days post-infection suggests that enhanced transcription, translation, and/or stability of the transgene products do not likely contribute to the mechanism responsible for this observation.

Combined Treatment of LLnL and EGTA Prevents Degradation of Internalized rAAV.

Figure 15A:
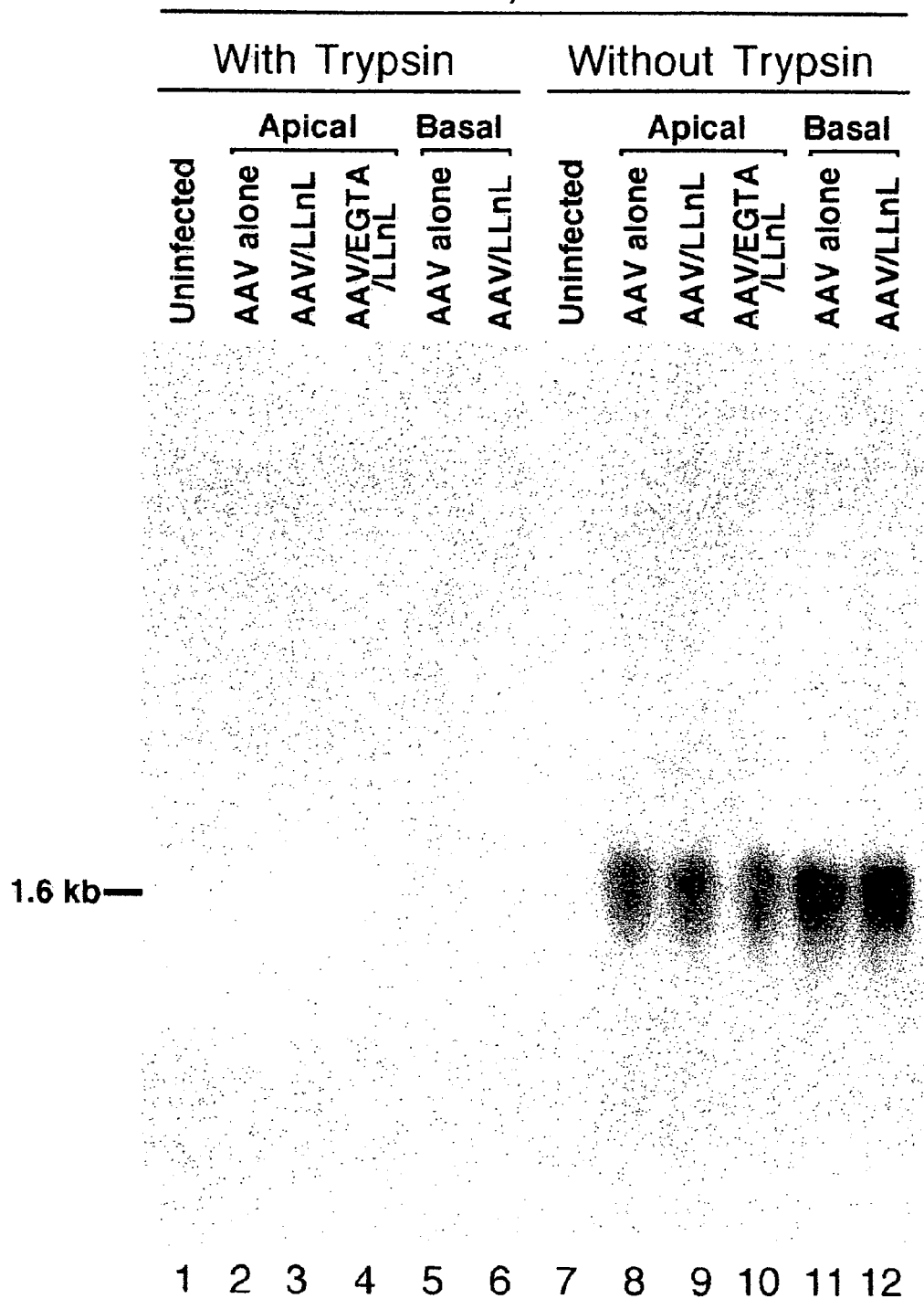
FIG. 15. Examination of rAAV endocytosis by Southern blot analysis of viral DNA. Hirt DNA from AV.GFP3ori infected or mock infected (Lanes 1 and 7 in both Panels A and B) human bronchial epithelia were extracted for a direct examination of viral genomes by Southern blotting against a P$^{32}$-labeled EGFP probe. Panel A depicts viral binding studies in the presence and absence of LLnL with or without EGTA treatment prior to apical or basolateral infection for 1 hour at 4° C. Cell surface-bound virus was completely removed by trypsin (Panel A, lanes 2 through 6). To determine the amount of the surface-bound rAVV, cells were infected with AV.GFP3ori for 1 hour at 4° C. and were not treated with trypsin prior to Hirt DNA extraction. Panel A: lane 8: apical AAV infection; lane 9: apical AAV infection in the presence of LLnL; lane 10: cells were pre-treated with hypotonic EGTA prior to apical infection in the presence of LLnL; lane 11: basolateral infection; lane 12: basolateral infection in the presence of LLnL. Panel B depicts the results of studies evaluating rAAV internalization from either the apical or the basolateral surface in the presence or absence of LLnL, and the internalization from the apical surface after combined treatment with hypotonic EGTA and LLnL. To detect the net amount of the internalized viral genome, all samples in Panel B were treated with trypsin just before Hirt DNA was harvested. The extent of the internalized virus at 4 hours (Panel B, lanes 2 through 6) and 24 hours (Panel B, lanes 8 through 12) incubation at 37° C. after infection is represented by the intensity of the 1.6 kb single stranded viral genome band. Panel B; lane 2: apical AAV infection for 4 hours; lane 3: apical AAV infection in the presence of LLnL for 4 hours; lane 4: cells were pre-treated with hypotonic EGTA prior to apical infection in the presence of LLnL for 4 hours; lane 5: basal infection for 4 hours; lane 6: basolateral infection in the presence of LLnL for 4 hours; lane 8: apical infection for 24 hours; lane 9: apical infection in the presence of LLnL for 24 hours; lane 10: cells were pre-treated with hypotonic EGTA prior to apical infection in the presence of LLnL for 24 hours; lane 11: basolateral infection for 24 hours; lane 12: basolateral infection in the presence of LLnL for 24 hours. Panel C compares the effect of LLnL/EGTA on rAAV genomes at 2, 10, 30 days following a 24 hour infection from the apical (lanes 1, 2, 5, 6, 10, 11 and 12) and basolateral (lanes 3, 4, 7, 8, 9, 13 and 14) membranes. Treatment conditions are noted above each lane; transwells were not treated with trypsin prior to harvesting Hirt DNA. An additional control included co-infection with Ad.d1802 (MOI=500 part/cell) to demonstrate replication form monomers (lane 9, 4.7 kb). It should be noted that different exposure times were used for the three different panels in C (lanes 1-4, 3 hours; lanes 5-8, 15 hours; lanes 10-14; 12 hours). Matched DNA samples from uninfected cultures did not demonstrate detectable hybridization (data not shown).
Figure 15B:
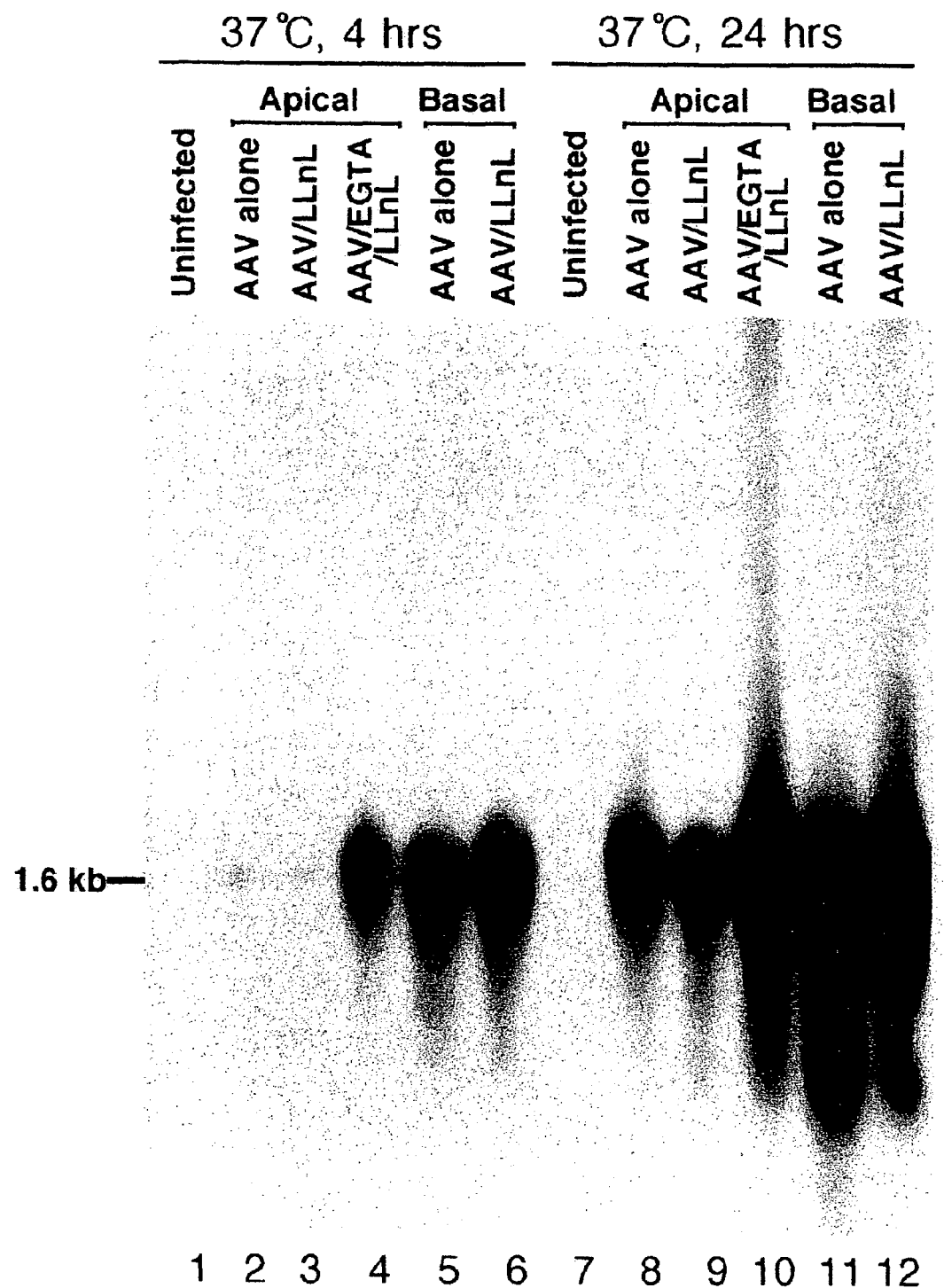
Figure 15C:
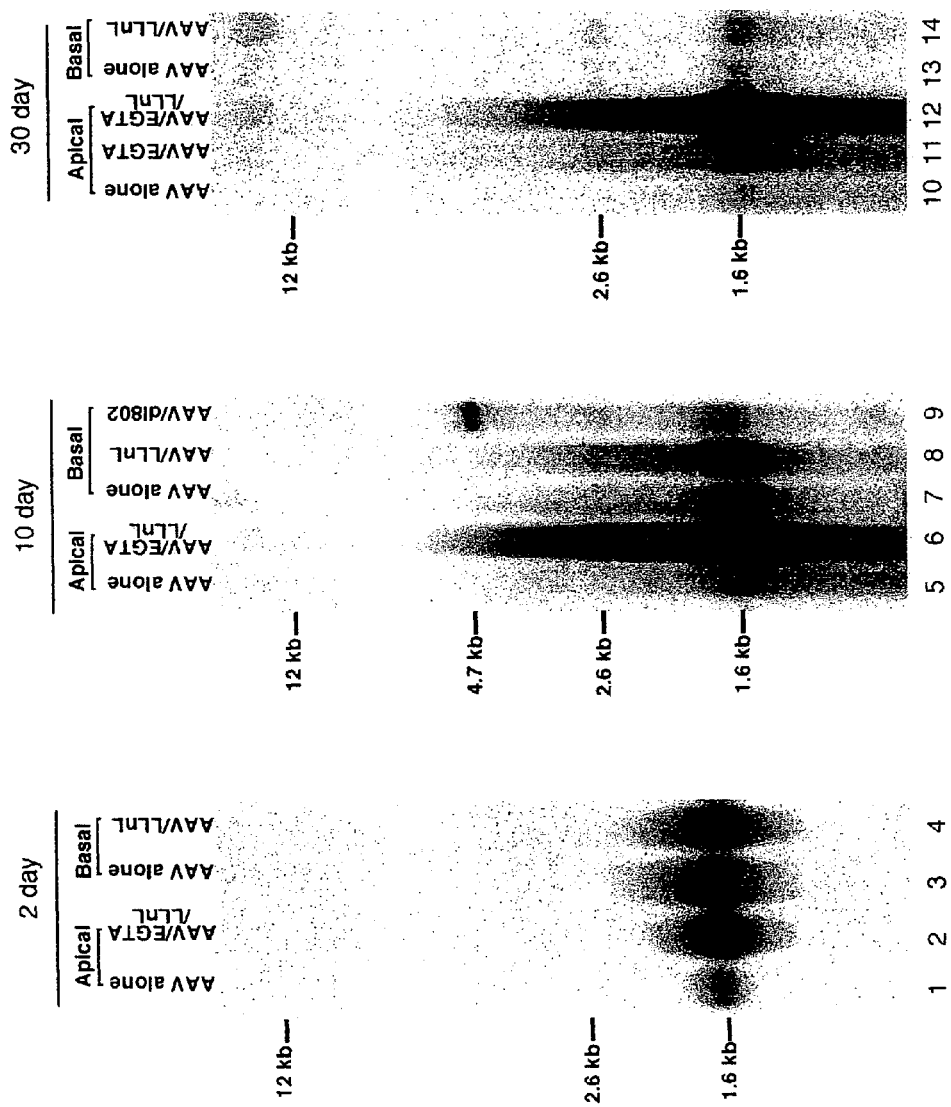
Figure 18A:
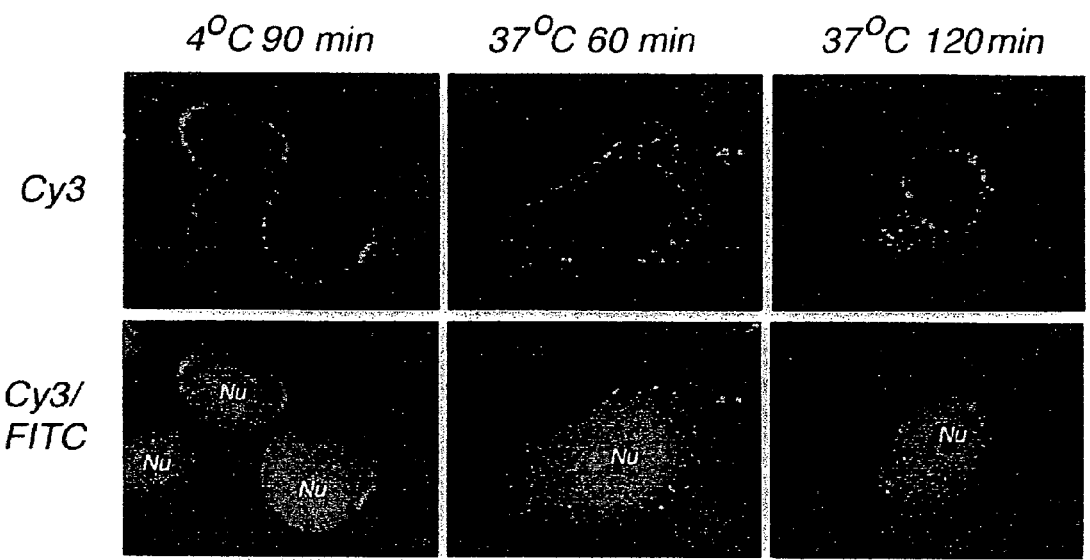
FIG. 18. Cy3-labeled rAAV infection in Hela cells. Hela cells were infected with Cy3-labeled AV.GFP3ori at an MOI of 500 particles/cells for 90 minutes at 4° C. in the absence of serum. Cells were then washed and either directly fixed in 2% paraformaldehyde for 10 minutes or incubated at 37° C. for an additional 60 or 120 minutes prior to fixation. Prior to viral infections, cells were incubated for 30 minutes in 1 µM 5-chloromethylfluorescein diacetate (Cell Tracker™ Green CMFDA, Molecular Probe) to allow for visualization of cells and labeled virus in dual fluorescent channel images. Representative confocal image of cells infected for 90 minutes at 4° C. followed by a 60 and 120 minute incubation at 37° C. are shown for both Cy3 and dual Cy3/FITC channels (Panel A). The nuclei in dual channel images are marked by Nu. The confocal images shown were merged from three 0.5 µm layers taken within the central region of the cell. Panel B depicts non-confocal images with Nomarski and Cy3 channels for cells infected for 90 minutes at 4° C. (left side of Panel B) followed by a 120 minute incubation at 37° C. (right side of Panel B). Virus binding at 4° C. localizes to the surface membrane of the cell. With increased incubation time at 37° C., virus was translocated to the nuclear membrane. Viral binding at 4° C. was also competed by the addition of free heparin at the indicated concentrations shown in Panel C (confocal images shown from three merged layer). Endocytosis of FITC-labeled transferrin and Cy3-labeled rAAV was observed in Hela cells (Panel D). Hela cells were infected with Cy3 rAAV in the presence of FITC-labeled transferrin for 90 minutes at 4° C. followed by washing. Cells were then placed at 37° C. for 30 minutes prior to fixation and analysis by confocal microscopy. Images in Panel D were a single 0.5 µm cross section for Cy3, FITC, and combined channels (merged). Results demonstrate colocalization of rAAV and transferrin in the majority of endocytic vesicles.
Figure 18B:
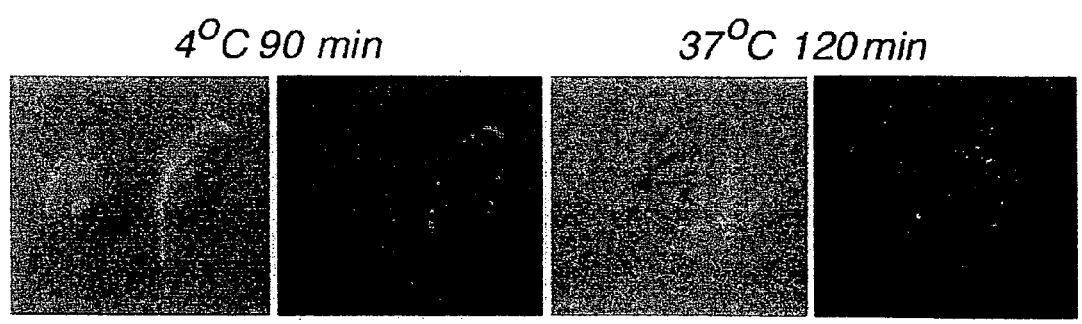
Figure 18C:
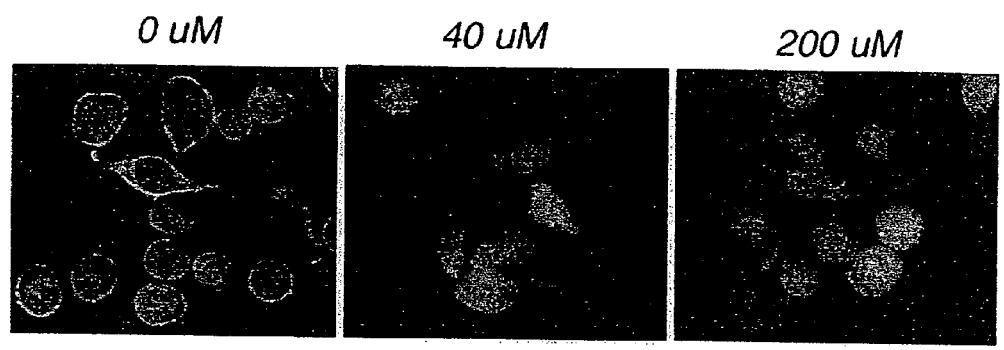
Figure 18D:
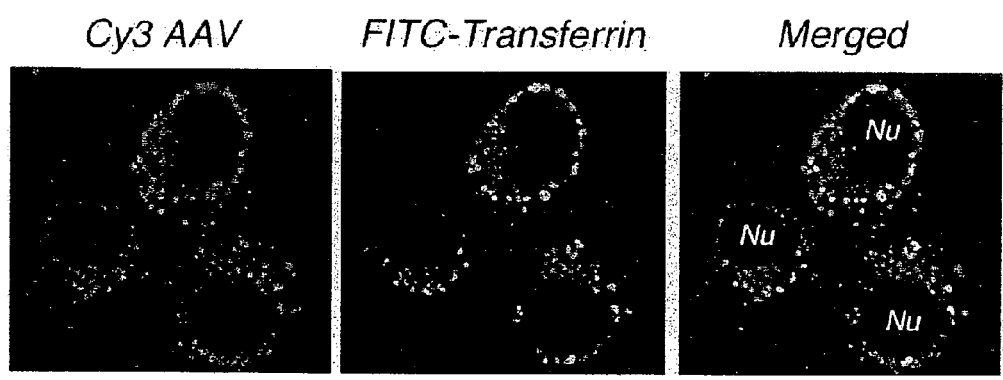

To further clarify the molecular mechanism(s) responsible for augmentation of rAAV transduction by LLnL, rAAV genomes in infected cells were analyzed by Southern blotting Hirt DNA. Consistent with studies using $S^{35}$ labeled virus (FIG. 12), rAAV binding to either surface of polarized airway epithelia was not affected by LLnL treatment (FIG. 15A, lane 8 and 9 for apical infection, lane 11 and 12 for basal infection). Southern blotting also demonstrated 2 to 7 fold higher viral binding from the basal surface, which varied among different tissue samples (data not shown). The extent of virus internalization was compared after stripping surface bound virus with trypsin. Confirming previous results (FIGS. 8, 12 and 13), a significant amount of rAAV was endocytosed from the apical surface during the infection period (FIG. 15B, lane 2 and 3, lane 8 and 9), although viral uptake was more active from basolateral surface (FIG. 18B, lane 5 and 6, lane 11 and 12). LLnL alone also did not substantially prevent enzymatic degradation of the internalized AAV viral DNA (FIG. 15B, also see FIG. 11), indicating that enhanced viral trafficking into the nucleus might be more important in the observed augmentation by LLnL. However, treatment with both hypotonic EGTA and LLnL substantially increased the amount of virus internalized from apical surface (FIG. 15, compare lanes 2, 4 and lanes 8, 10; FIG. 18C compare lanes 1, 2, and 5, 6, and 10, 12). Since hypotonic EGTA treatment alone only slightly increased persistence of AAV DNA (less than 4-fold, FIG. 18C, lane 11) or AAV-mediated gene expression (less than 10-fold, FIG. 5B) (Duan et al., 1998; Walters et al., 2000) following apical infection, the predominant mechanism responsible for the combined effects of EGTA and LLnL might be due to reduced degradation of the internalized virus and an increased rate of endocytosis. These synergistic effects of EGTA and LLnL augment rAAV transduction from the apical membrane more than 200-fold. Additionally, the conversion of single stranded viral genomes to linear replication or circular forms has been associated with enhanced AAV transduction by adenoviral early gene products or UV irradiation, respectively (Fisher et al., 1996; Sanlioglu et al., 1999; Duan et al., 1999). As shown in Southern blots of Hirt DNA from cultures co-infected with Ad.d1802 and rAAV (FIG. 15C, lane 9), LLnL enhanced AAV transduction was clearly not mediated through the formation of linear replication intermediates (4.7 kb band) as seen in the presence of adenoviral E4orf6 protein produced by Ad.d1802 co-infection.

Ubiquitination of Viral Capsid Proteins Following rAAV Infection in the Airway Alters the Efficiency of Transduction.

Figure 16A:
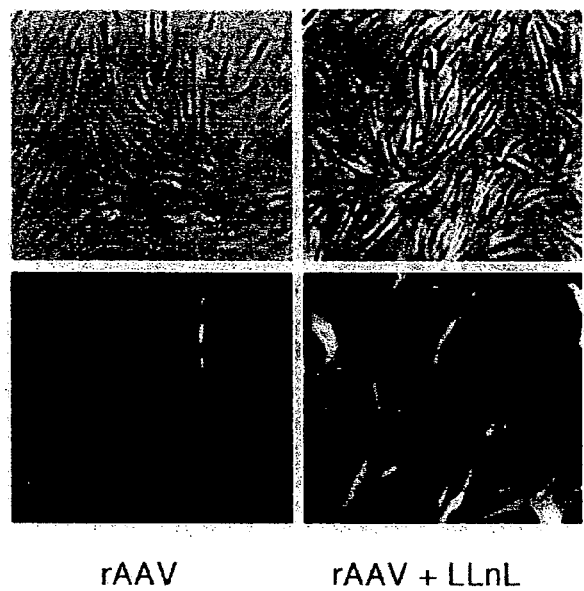
FIG. 16. Modification of the viral ubiquitination state facilitates rAAV transduction. Similar to the polarized human airway ells rAAV transduction in human primary confluent fibroblasts was also augmented by tripeptide proteasome inhibitors. 80% confluent human primary fibroblasts were infected with AV.GFP3ori at an moi of 1000 DNA particles/cell. Panel A depicts GFP transgene expression in the absence (left photographs) and presence of 40 µM LLnL (right photographs) at 96 hours post-infection. Similar effects were achieved with 4 µM Z-LLL (data not shown). Top and bottom panels represent bright field and FITC-channel fluorescent photomicrographs, respectively. The mean (+/−SEM, N=3) percentage of cells transduced with rAAV, as measured by FACS sorting of GFP expressing cells, is presented in the bar graph of Panel B. Panel C demonstrates the identification of the ubiquitinated AAV capsid proteins (marked by arrowhead) 6 hours after infection of primary confluent fibroblasts. In this study, rAAV from infected cells was first immunoprecipitated with anti-VP 1,2,3 (AAV-2 capsid) monoclonal antibody followed by Western blot detection of ubiquitin side chains using an anti-ubiquitin monoclonal antibody. The two major background bands migrating at approximately 65 and 25 kd represent heavy and light chain antibody subunits which cross-react with secondary antibodies. Additionally, the equal intensity of lower molecular weight cross-reactive bands (30-40 kd) serve as internal controls for equal loading of protein. Panel D demonstrates augmentation of rAAV transduction in polarized airway epithelia by inhibitors of ubiquitin E3 ligase. Epithelia were infected with AV.GFP3ori (10,000 particles/cell) from the basolateral surface following treatment with ubiquitin ligase inhibitor dipeptides (0.2 mM H-Leu-Ala-OH and 0.2 mM H-His-Ala-OH). Results demonstrate the mean (+/−SEM, N=3) number of GFP expressing cells per 10× field at 1 and 15 days post-infection.
Figure 16B:
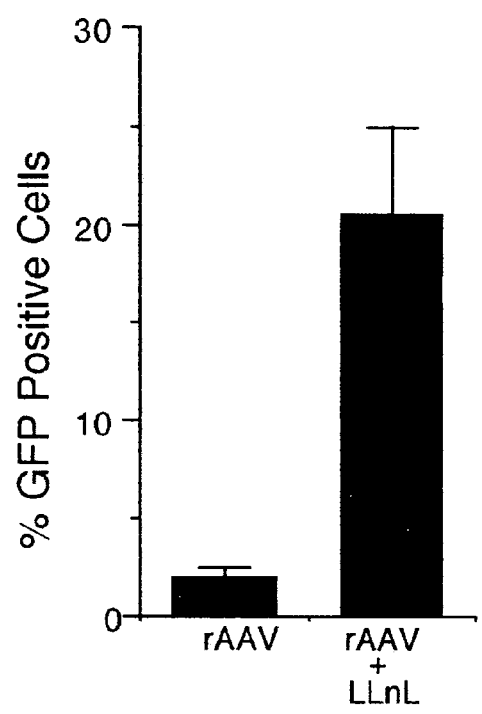
Figure 16C:
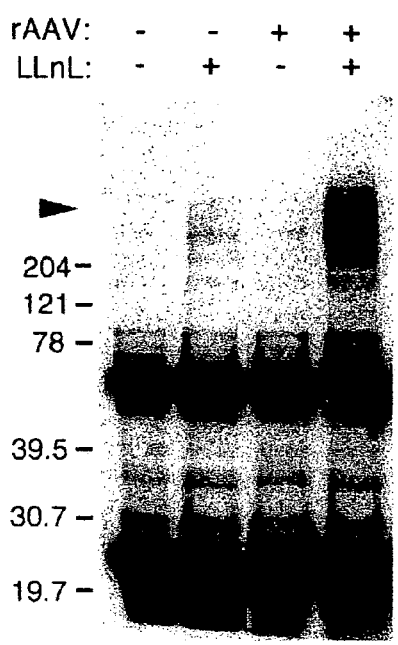
Figure 16D:
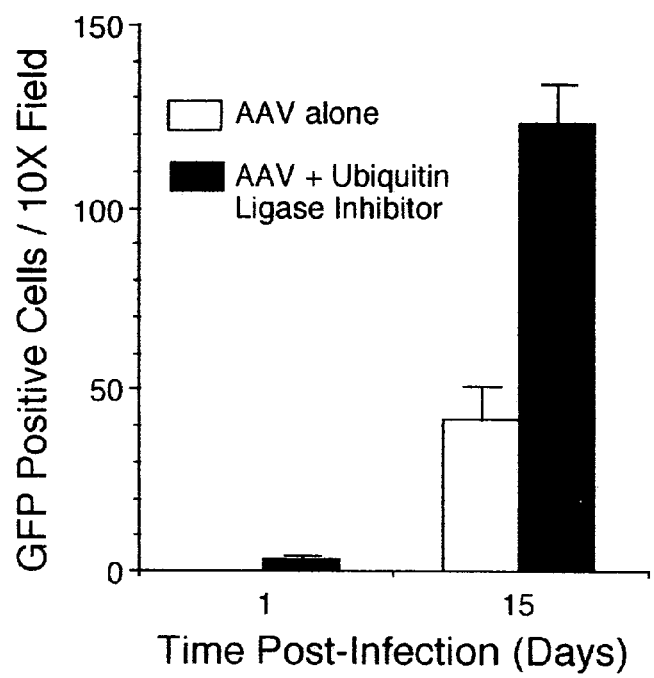

Proteasome-dependent degradation of ubiquitinated molecules represents a major pathway for disposal of both endogenous and foreign proteins (Schwartz et al., 1999). Several distinct steps in the regulation of this pathway have been identified, including: activation of ubiquitin by its activating enzyme (E1), transfer of the activated ubiquitin to the ubiquitin carrier protein (E2), and subsequent delivery of the activated ubiquitin to the protein substance by ubiquitin ligase (E3). Ultimately, ubiquitinated proteins are degraded by the 26S proteasome through an ATP-dependent process. To test whether enhancement of rAAV transduction by proteasome inhibitors involves liberation of ubiquitinated virus from an endosomal compartment, the extent of ubiquitin side chains on AAV capsid proteins following infection was examined as well as whether treatment with proteasome inhibitors altered the extent of ubiquitination. AAV capsid proteins were immunoprecipitated using anti-VP 1,2,3 antibody from rAAV infected human polarized airway cells and confluent human fibroblasts at 6 hours post-viral infection. Subsequent Western analysis with anti-ubiquitin specific antibodies demonstrated a significant increase in the cellular level of ubiquitinated AAV capsid in fibroblasts following proteasome treatment (FIG. 16B). Ubiquitination significantly increased the molecular weight of capsid proteins (63 kd, 73 kd, and 87 kd) to 220-250 kd and is consistent with the size change following ubiquitination for other molecules (Bregman et al., 1996). Unfortunately, the limited amount of virus retrievable from air-liquid interface cultured human airway cells precluded the ability to detect ubiquitinated capsid in this system (data not shown). Nonetheless, confluent primary fibroblasts also demonstrated augmentation (10-fold) of transgene expression following treatment with proteasome inhibitors. Thus, proteasome inhibitors increase rAAV transduction by decreasing the targeting and/or degradation of ubiquitinated AAV in the proteasome. The net result of such proteasome inhibition would be expected to increase the abundance of ubiquitinated viral capsid.

Because a technical limitation in polarized airway model prevented direct detection of ubiquitinated viral capsid, it was determined whether modulation of other steps in the ubiquitin proteasome pathway could also increase rAAV transduction similarly to that seen with proteasome inhibitors LLnL and Z-LLL. Several dipeptides, such as H-Leu-Ala-OH and H-His-Ala-OH, are known to inhibit ubiquitin ligase E3 (Obin et al., 1999). Application of these ubiquitin ligase inhibitors indeed enhanced rAAV transduction from the basolateral surface of human airway cells (FIG. 16, panel C). Taken together, data in both fibroblasts and polarized airway epithelia suggest that AAV capsid is ubiquitinated following endocytosis, and that this process is a barrier to rAAV transduction. The most plausible mechanism responsible for the augmentation of rAAV transduction by tripeptide proteasome inhibitors involves the prevention of ubiquitinated virus degradation and/or targeting to the proteasome.

Long-Term Enhancement of rAAV Transduction by Proteasome Inhibitor In Vivo.

Figures 17A, 17B, 17C:
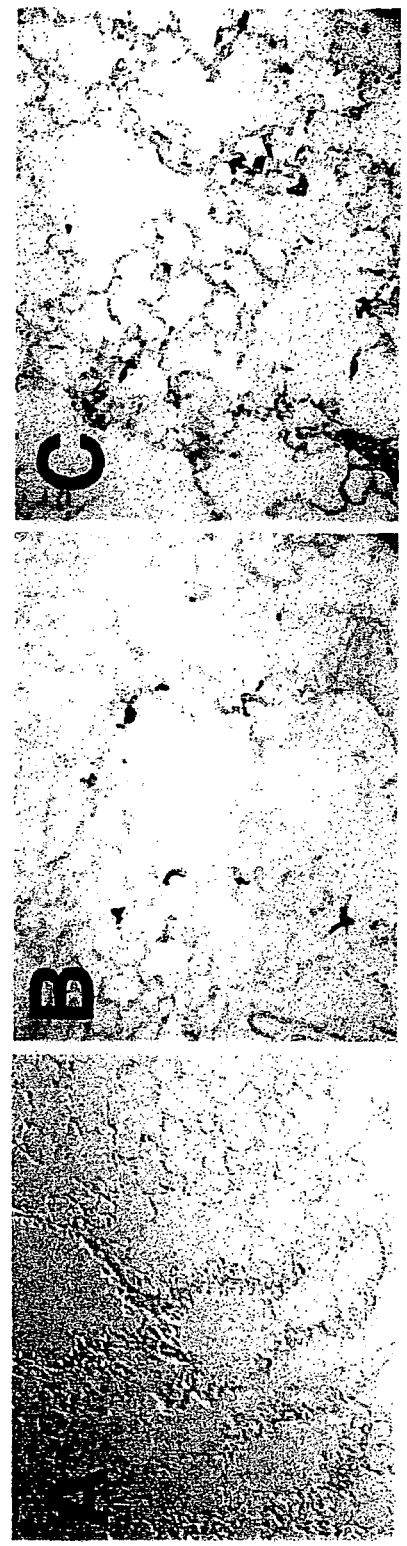
FIG. 17. Persistent induction of rAAV mediated gene transfer in mouse conducting airways by proteasome inhibitors. Panels A-C) Recombinant AV.Alkphos (5×10$^{10}$ particles) was administered to mouse lung either as virus alone in PBS or virus in combination with 40 µM LLnL in PBS. Virus was directly instilled into C57Balb/c mice trachea with a 30 G needle in a total volume of 30 µl. To insure the spread of the virus in mouse lung, 50 µl air was pumped into lung through the same syringe immediately after virus was administered. Ninety days after infection, lungs were harvested intact and fixed in 4% paraformaldehyde followed by cryosection. AAV-mediated transgene expression was evaluated by 10 µm tissue sections staining for heat-resistant alkaline phosphatase. Panel A: infection with AAV alone; Panels B and C: infection with AAV supplemented with 40 M of LLnL. Panels D-F) 6 week old BALB/c mouse (N=3 animals in each group) were infected with 5×10$^{10}$ DNA particles of AV.LacZ in the absence or presence of 400 µM Z-LLL by nasal instillation. Representative examples of histochemical staining for LacZ expression in large bronchioles 150 days post-infection are shown in Panel D and E. The right and left sides of each panel represent Nomarski and bright field photomicrographs, respectively. The 100 µm scale bar applies to all photomicrographs. The mean (+/−SEM) percentage of LacZ expressing epithelial cells at various levels of the airway was quantitated using the morphometric procedures outlined in the methods, and the analysis represents results from three independent animals for each group (Panel C).
Figure 17F:
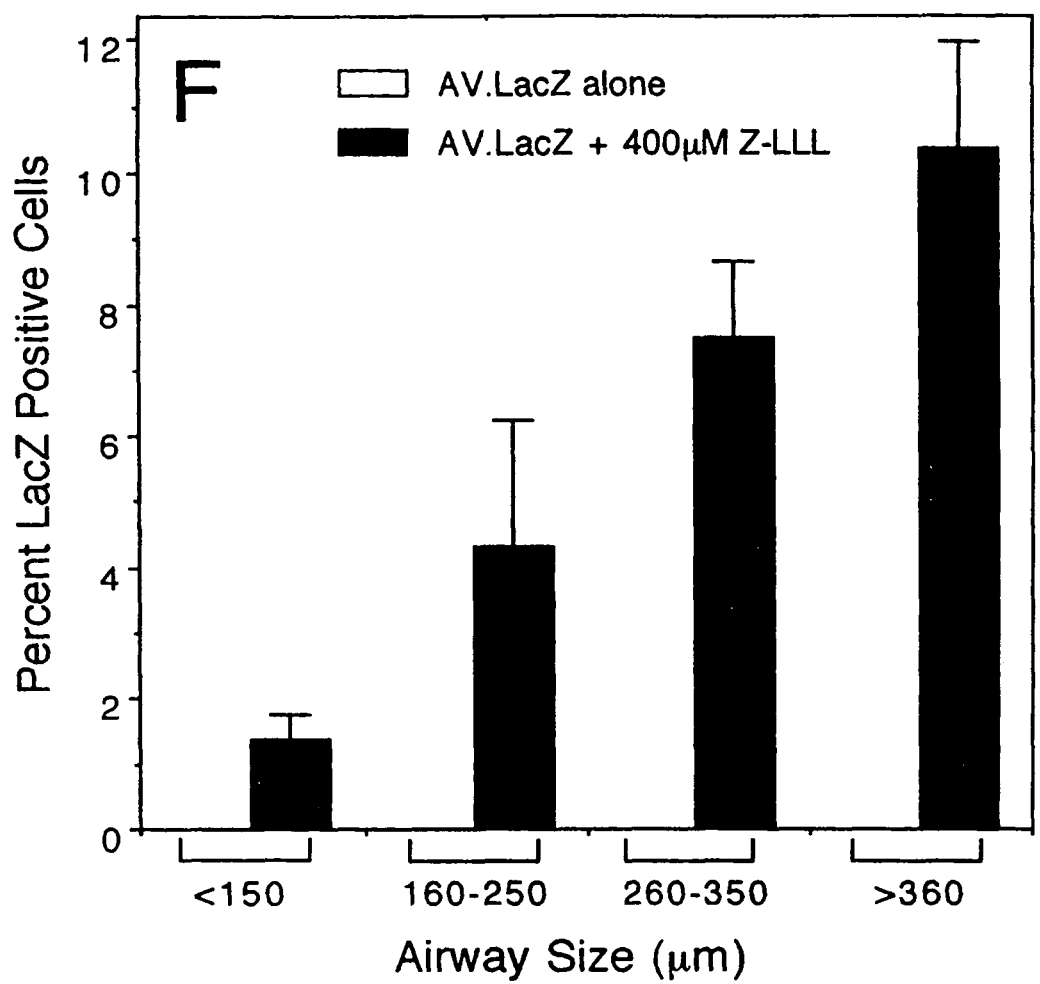

To evaluate the potential utility of proteasome inhibitors for in vivo gene therapy, both the toxicity and efficacy of these agents for in vivo rAAV mediated gene transfer in the mouse lung was tested. To assess the toxicity of these proteasome inhibitors in mice, 10, 100, and 1000 fold higher effective doses of LLnL or Z-LLL were administered than used to induce gene transfer in polarized airway cells, using both intra-tracheal and systemic (IV) delivery. No toxicity was indicated by histologic evaluation of the lung and liver (data not shown) or was evidenced by the death of animals. To investigate whether these proteasome inhibitors could improve rAAV transduction in vivo, AV.LacZ ($5 \times 10^{10}$ particles) was delivered either alone or in the presence of 400 μM Z-LLL by intranasal administration. Mouse lungs were harvested at 3, 10 and 150 days post-infection to evaluate short and long term effects. Proteasome inhibitor treatment from basal surface (FIG. 7B), or in conjunction with EGTA from apical surface (FIG. 11B), resulted in pronounced, immediate enhancement on rAAV transduction, however, X-gal staining of the lung tissues at 3 and 10 days post infection demonstrated no detectable transgene expression in either proteasome inhibitor treated or untreated groups (data not shown). In contrast, significant transduction was achieved at 150 days in Z-LLL treated samples (see FIG. 17E). Targeted transgene expression was predominantly confined to the conducting airways, rather than in the parenchyma. Alveolar cells were rarely transduced. Although on average only about 5.88% of airway cells were transduced by AV.LacZ, and LacZ positive cells were observed throughout the entire conducting airway, a characteristic transduction profile was evident. The transduction efficiency in larger bronchioles (>350 mm) reached a mean of 10.36±1.63% of the airway epithelium, while 1.37±0.41% of airways cells in the smaller bronchioles (<150 mm) expressed the β-galactosidase transgene (FIG. 17F). The range of transgene expression in distal and proximal airways was 0 to 4% and 5 to 18%, respectively. This transduction profile demonstrating a higher and more consistent transduction in larger airways likely reflects a more uneven delivery of virus to regions of the lung encompassing the smaller airways. Examination of cryo-sections from lungs infected by AV.LacZ alone revealed only 2 lacZ positive cells in a total of 3.15 airway sections (n=3 animals).

Discussion

Inefficient gene transfer from the apical surface of the airway has been a major obstacle in numerous gene therapy approaches for cystic fibrosis utilizing recombinant adenovirus (Walters et al., 1999; Pickles et al., 1998), adeno-associated virus (Duan et al., 1998), retrovirus (Wang et al., 1998), and non-viral liposome vectors (Chu et al., 1999). It has been generally thought that inefficient viral mediated gene delivery through the apical membrane of airway epithelia is predominantly due to the lack of receptors or co-receptors on this surface.

Molecular analysis of rAAV infection in polarized airway epithelia has revealed several unique findings. First, there is conclusive evidence that the previously reported lack of known AAV-2 receptor and co-receptors (Duan et al., 1999) at the apical membrane of airway epithelia does not abrogate AAV infection. Although transduction (as determined by transgene expression) from the basolateral surface is 200-fold more efficient than from the apical membrane, quantitative and semi-quantitative analyses of viral endocytosis with either $S^{35}$-labeled virus or Southern blotting have demonstrated that viral uptake from the apical surface is only 2-7 fold less efficient than from the basolateral membrane. Therefore, it is reasonable to assume that previously unidentified alternative receptor/co-receptors and/or receptor-independent mechanism(s) might be involved in AAV uptake from the mucosal surface of the airway.

Polarity is widely recognized to significantly influence endosomal processing of many proteins, and distinct sorting mechanisms have been described for the apical and basolateral compartments (Odorizzi et al., 1996; Rodriguez-Boulan et al., 1993). The lack of a direct correlation between the efficiency of viral uptake and transgene expression following basolateral and apical infection suggest that additional post-endocytic barriers exist for rAAV mediated gene transfer. Differences in the extent of AAV nuclear trafficking following basolateral versus apical routes of infection suggest that basal and apical cellular compartments possess distinct biologic properties that may influence the polarity of AAV transduction. Endosomal processing barriers to rAAV transduction may not be limited to polarized epithelial cells. In support of this notion, impaired intracellular trafficking of viral particles to the nucleus has been observed in NIH 3T3 cells. In addition, rAAV can remain in an inactive state for as long as 7 days in confluent primary fibroblast cells until rescued by UV irradiation to a functionally active state. Thus, post-endocytic barriers to infection exist in multiple cell types.

In the airway, the major rate-limiting steps in rAAV transduction from the mucosal surface appear to involve inefficient endosomal processing of the internalized virus. Regulated intracellular proteolysis through proteasomes plays a critical role in many physiological and pathological conditions (Schwartz et al., 1999; Kato, 1999). Recent identifications of many specific proteasome inhibitors has set the foundation for pharmacologic intervention in this cellular enzymatic system as a novel therapeutic approach. For example, several cell permeable synthetic tripeptide aldhehydes (such as LLnL and Z-LLL used in this study) have been demonstrated to be promising cancer therapy agents or anti-inflammatory drugs (Goldberg et al., 1995; Kloetzel, 1998; Wojcik, 1999). Additionally, the proteasome has been suggested to have antiviral functions in HIV infection (Schwartz et al., 1998), implying that the inhibition of proteosome function could be beneficial in promoting transduction with recombinant viruses. Based on the molecular evidence that apical infection of rAAV in the airway is significantly limited by post-entry events, ubiquitin/proteasome pathways appear to be instrumental in this blockage. The proteasome is commonly know as a compartment for clearance of endogenous and foreign proteins. However, recent studies also suggested that the proteasome system is involved in regulating endocytosis (Bonifacino et al., 1998; Strous et al., 1999). From the standpoint of gene delivery, proteasome inhibitors have been shown to protect transfected plasmid DNA from degradation (Coonrod et al., 1997). The results described herein clearly demonstrate that rAAV mediated gene transfer to the airway epithelia is also significantly enhanced by proteasome inhibitors. Furthermore, this enhancement is correlated with proteasome inhibitor stimulated viral trafficking to the nucleus. Although proteasome inhibitors increased long-term levels of AAV transduction form the apical surface, their effect on basolateral infection appeared predominantly to alter the rate, rather than the long-term levels, of transduction. These differences highlight fundamentally distinct pathways involved in rAAV transduction from apical and basolateral surfaces.

Several findings also support the notion that ubiquitination of virus following endocytosis may be a critical mechanism for sorting incoming AAV. First, treatment of airway epithelia with proteasome inhibitors know to block ubiquitin-dependent degradation of proteins enhances rAAV gene transfer. Second, inhibition of ubiquitin E3 ligase activity in airway epithelia also enhances transduction. Lastly, rAAV capsid proteins are ubiquitinated following infection in confluent human fibroblasts, and that the extent of this ubiquitination is increased by inhibition of ubiquitin-proteasome degradative pathways (FIG. 16).

From an applied standpoint, one of the most important findings in this study is the persistent high level of rAAV transduction induced by proteasome inhibitor in mouse lung. Co-administration of Z-LLL with rAAV increased transgene expression from undetectable levels to 10.36+/−1.63% of proximal bronchial epithelial cells at 150 days post-infection. This level of gene expression is thought to be sufficient for therapeutic correction of CFTR deficiency (Crystal, 1999). The feasibility of this strategy for clinical application is further supported by the lack of a detectable local or systemic toxicity following proteasome inhibitor administration to mice. Furthermore, preliminary studies in several other organs, e.g., heart skeletal muscle and liver, have suggested that ubiquitination of rAAV2 may occur in an organ-specific fashion. The application of proteasome inhibitors in skeletal and cardiac muscle had no effect on either short-term or long-term rAAV mediated gene transfer. However, application of Z-LLL in the liver (see Example 7) led to a 7-fold increase in rAAV transduction at 1 month post-infection. These findings suggest that tripeptide proteasome inhibitors could be used to increase gene transfer in organs other than the lung, depending on the cell biology of virus processing.

In conclusion, a significant barrier to apical infection in the airway with rAAV-2 lies at the level of endosomal processing and ubiquitination. Modulation of the ubiquitin-proteasome system has revealed innovative strategies to enhance rAAV transduction from the mucosal surface of the airway for gene therapy of cystic fibrosis.

Example 7

Expression of the Alkaline Phosphatase Gene in Lung Airway Epithelium and Liver In Vivo The in vivo activity of rAAV in the presence or absence of an agent of the invention in the lung or liver may be tested using the alkaline phosphatase (AP) gene. A rAAV vector containing the AP gene, recombinant AV.Alkphos ($5 \times 10^{10}$ particles), was administered to mouse lung either as virus alone in PBS or virus in combination with 40 μM LLnL in PBS. Virus was directly instilled into C57Balb/c mice trachea with a 30 G needle in a total volume of 30 μl. To insure the spread of the virus in mouse lung, 50 μl air was pumped into lung through the same syringe immediately after virus was administered. Ninety days after infection, lungs were harvested intact and fixed in 4% paraformaldehyde followed by cryosection. AAV-mediated transgene expression was evaluated by 10 μm tissue sections staining for heat-resistant alkaline phosphatase (FIGS. 17A-C).

Recombinant AV.Alkphos ($5 \times 10^{10}$ particles) was also administered to mouse liver either as virus alone in PBS, virus in combination with 40 μM Z-LLL in PBS, or virus in combination with 20 μM LLnL in PBS. Virus was directly instilled into portal vein of the C57B6 mice. AAV-mediated alkaline phosphatase transgene expression was evaluated by histology staining at 2 and 4 weeks post infection in frozen tissue sections (FIG. 12).

REFERENCES

Alexander, I. E., D. W. Russell, and A. D. Miller. DNA-damaging agents greatly increase the transduction of non-dividing cells by adeno-associated virus vectors. *J. Virol.*, 68, 8282-7 (1994).

Alexander, I. E., D. W. Russell, A. M. Spence, and A. D. Miller. Effects of gamma irradiation on the transduction of dividing and nondividing cells in brain and muscle of rats by adeno-associated virus vectors. *Hum. Gene Ther.*, 7, 841-50 (1996).

Bartlett, J. S., R. J. Samulski, and T. J. McCown. Selective and rapid uptake of adeno-associated virus-type 2 in brain. *Hum. Gene Ther.*, 9, 1181-6 (1998).

Bartlett, J. S., J. Kleinschmidt, R. C. Boucher, and R. J. Samulski. Targeted adeno-associated virus vector transduction of non-permissive cells mediated by a bispecific F(ab'gamma)2 antibody. *Nat. Biotechnol.*, 17(2), 181-6 (1999).

Basak, S., and R. W. Compans. Polarized entry of canine parvovirus in an epithelial cell line. *J. Virol.*, 63, 3164-7 (1989).

Basak, S., and H. Turner. Infectious entry pathway for canine parvovirus. *Virology*, 186, 368-76 (1992).

Berg, T. O., M. Fengsrud, P. E. Stromhaug, T. Berg, and P. O. Seglen. Isolation and characterization of rat liver amphisomes. Evidence for fusion of autophagosomes with both early and late endosomes. *J. Biol. Chem.*, 273, 21883-92 (1998).

Bertran, J., Y. Yang, P. Hargrove, E. F. Vanin, and A. W. Nienhuis. Targeted integration of a recombinant globin gene adeno-associated viral vector into human chromosome 19. *Ann. N.Y. Acad. Sci.*, 850, 163-177 (1998).

Blau, D. M., and R. W. Compans. Entry and release of measles virus are polarized in epithelial cells. *Virology*, 210, 91-9 (1995).

Blommaart, E. F., U. Krause, J. P. Schellens, H. Vreeling-Sindelarova, and A. J. Meijer. The phosphatidylinositol 3-kinase inhibitors wortmannin and LY294002 inhibit autophagy in isolated rat hepatocytes. *Eur. J. Biochem.*, 243, 240-6 (1997).

Bonifacino, J. S., and A. M. Weissman. Ubiquitin and the control of protein fate in the secretory and endocytic pathways. *Ann. Rev. Cell Dev. Biol.*, 14, 19-57 (1998).

Bregman, D. B., R. Halaban, A. J. van Gool, K. A. Henning, E. C. Friedberg, and S. L. Warren. UV-induced ubiquitination of RNA polymerase II: a novel modification deficient in Cockayne syndrome cells. *Proc. Natl. Acad. Sci. USA*, 93, 11586-90 (1996).

Britten, R. A., and D. Murray. Constancy of the relative biological effectiveness of 42 MeV (p→Be+) neutrons among cell lines with different DNA repair proficiencies. *Radiat. Res.*, 148, 308-16 (1997).

Ceresa, B. P., A. W. Kao, S. R. Santeler, and J. E. Pessin. Inhibition of clathrin-mediated endocytosis selectively attenuates specific insulin receptor signal transduction pathways. *Mol. Cell Biol.*, 18, 3862-70 (1998).

Chen, J. W., T. L. Murphy, M. C. Willingham, I. Pastan, and J. T. August. Identification of two lysosomal membrane glycoproteins. *J. Cell Biol.*, 101, 85-95 (1985).

Chiorini, J. A., M. D. Weitzman, R. A. Owens, E. Urcelay, B. Safer, and R. M. Kotin. Biologically active Rep proteins of adeno-associated virus type 2 produced as fusion proteins in *Escherichia coli*. *J. Virol.*, 68, 797-804 (1994).

Chu, Q., J. D. Tousignant, S. Fang, C. Jiang, L. H. Chen, S. H. Cheng, R. K. Scheule, and S. J. Eastman. Binding and uptake of cationic lipid:pDNA complexes by polarized airway epithelial cells. *Hum. Gene Ther.*, 10, 25-36 (1999).

Clayson, E. T. and R. W. Compans. Entry of simian virus 40 is restricted to apical surfaces of polarized epithelial cells. *Mol. Cell Biol.*, 8, 3391-6 (1988).

Conforti, G., M. Calza, and A. Beltran-Nunez. Alpha v beta 5 integrin is localized at focal contacts by HT-1080 fibrosarcoma cells and human skin fibroblasts attached to vitronectin. *Cell Adhes. Commun.*, 1, 279-93 (1994).

Conrad, C. K., S. S. Allen, S. A. Afione, T. C. Reynolds, S. E. Beck, M. Fee-Maki, X. Barrazza-Ortiz, R. Adams, F. B. Askin, B. J. Carter, W. B. Guggino, and T. R. Flotte. Safety of single-dose administration of an adeno-associated virus (AAV)-CFTR vector in the primate lung. *Gene Ther.*, 3, 658-68 (1996).

Coonrod, A., F. Q. Li, and M. Horwitz. On the mechanism of DNA transfection: efficient gene transfer without viruses. *Gene Ther.*, 4, 1313-21 (1997).

Crystal, R. G. Bad for cats, good for humans? Modified feline immunodeficiency virus for gene therapy [comment]. *J. Clin. Invest.*, 104, 1491-93 (1999).

Duan, D., K. J. Fisher, J. F. Burda, and J. F. Engelhardt. Structural and functional heterogeneity of integrated recombinant AAV genomes. *Virus Res.*, 48, 41-56 (1997).

Duan, D., A. Sehgal, J. Yao, and J. F. Engelhardt. Lef1 Transcription Factor Expression Defines Airway Progenitor Cell Targets for In Utero Gene Therapy of Submucosal Gland in Cystic Fibrosis. *Am. J. Respir. Cell Mol. Biol.*, 18, 750-758 (1998).

Duan, D., P. Sharma, J. Yang, Y. Yue, L. Dudus, Y. Zhang, K. J. Fisher, and J. F. Engelhardt. Circular intermediates of recombinant adeno-associated virus have defined structural characteristics responsible for long-term episomal persistence in muscle tissue. *J. Virol.*, 72, 8568-77 (1998).

Duan, D., Y. Yue, Z. Yan, P. B. McCray, and J. F. Engelhardt. Polarity influences the efficiency of recombinant adeno-associated virus infection in differentiated airway epithelia *Hum. Gene Ther.*, 9, 2761-76 (1998).

Duan, D., Y. Yue, Z. Yan, P. B. McCray, and J. F. Engelhardt. Polarity Influences the efficiency of recombinant adeno-associated virus infection in differentiated airway epithelia. *Hum. Gene Ther.*, 10, 1553-7 (1998).

Duan, D., Y. Yue, and J. F. Engelhardt. Response to "Polarity Influences the Efficiency of Recombinant Adeno-associate Virus Infection in Differentiated Airway Epithelia." *Hum. Gene Ther.*, 10, 1553-7 (1999).

Duan, D., P. Sharma, L. Dudus, Y. Zhang, S. Sanlioglu, Z. Yan, Y. Yue, Y. Ye, R. Lester, J. Yang, K J. Fisher, and J. F. Engelhardt. Formation of Adeno-Associated Virus Circular Genomes Is Differentially Regulated by Adenovirus E4 ORF6 and E2a Gene expression. *J. Virol.*, 73, 161-169 (1999).

Engelhardt, J. F., J. R. Yankaskas, S. A. Ernst, Y. Yang, C. R. Marino, R. C. Boucher, J. A. Cohn, and J. M. Wilson. Submucosal glands are the predominant site of CFTR expression in the human bronchus. *Nat. Genet.*, 2, 240-8 (1992).

Engelhard, J. F., J. R. Yankaskas, and J. M. Wilson. In vivo retroviral gene transfer into human bronchial epithelia of xenografts. *J. Clin. Invest.*, 90, 2598-607 (1992).

Engelhardt, J. F., Y. Yang, L. D. Stratford-Perricaudet, E. D. Allen, K. Kozarsky, M. Perricaudet, J. R. Yankaskas, and J. M. Wilson. Direct gene transfer of human CFTR into human bronchial epithelia of xenografts with E1-deleted adenoviruses. *Nat. Genet.*, 4, 27-34 (1993).

Engelhardt, J. F., H. Schlossberg, J. R. Yankaskas, and L. Dudus. Progenitor cells of the adult human airway involved in submucosal gland development. *Development*, 121, 2031-46 (1995).

Everett, R. D., A. Orr, and C. M. Preston. A viral activator of gene expression functions via the ubiquitin-proteasome pathway. *EMBO J.*, 17, 161-9 (1998).

Fenteany, G., R F. Standaert, W. S. Lane, S. Choi, E. J. Corey, and S. L. Schreiber. Inhibition of proteasome activities and subunit-specific amino-terminal threonine modification by lactacystin. *Science*, 268, 726-31 (1995).

Ferrari, F. K., T. Samulski, T. Shenk, and R. J. Samulski. Second-strand synthesis is a rate-limiting step for efficient transduction by recombinant adeno-associated virus vectors. *J. Virol.*, 70, 3227-34 (1996).

Fisher, K. J., G. P. Gao, M. D. Weitzman, R. DeMatteo, J. F. Burda, and J. M. Wilson. Transduction with recombinant adeno-associated virus for gene therapy is limited by leading-strand synthesis. *J. Virol.*, 70, 520-32 (1996).

Flotte, T. R., S. A. Afione, C. Conrad, S. A. McGrath, R. Solow, H. Oka, P. L. Zeitlin, W. B. Guggino, and B. J. Carter. Stable in vivo expression of the cystic fibrosis transmembrane conductance regulator with an adeno-associated virus vector. *Proc. Natl. Acad. Sci. USA*, 90, 10613-7 (1993).

Folli, F., D. Alvaro, A. Gigliozzi, C. Bassotti, C. R. Kahn, A. E. Pontiroli, L. Capocaccia, A. M. Jezequel, and A. Benedetti. Regulation of endocytic-transcytotic pathways and bile secretion by phosphatidylinositol 3-kinase in rats. *Gastroenterology*, 113, 954-65 (1997).

Fuller, S., C. H. von Bonsdorff, and K. Simons. Vesicular stomatitis virus infects and matures only through the basolateral surface of the polarized epithelial cell line, MDCK. *Cell.* 38, 65-77 (1984).

Gibson, A., C. E. Futter, S. Maxwell, E. H. Allchin, M. Shipman, J. P. Kraehenbuhl, D. Domingo, G. Odorizzi, I. S. Trowbridge, and C. R. Hopkins. Sorting mechanisms regulating membrane protein traffic in the apical transcytotic pathway of polarized MDCK cells. *J. Cell Biol.*, 143, 81-94 (1998).

Goldberg, A. L., R. Stein, and J. Adams. New insights into proteasome function: from archaebacteria to drug development. *Chem. Biol.*, 2, 503-8 (1995).

Goldenthal, K. L., K. Hedman, J. W. Chen, J. T. August, P. Vihko, I. Pastan, and M. C. Willingham. Pre-lysosomal divergence of alpha 2-macroglobulin and transferrin: a kinetic study using a monoclonal antibody against a lysosomal membrane glycoprotein (LAMP-1). *J. Histochem. Cytochem.*, 36, 391-400 (1988).

Goldman, M. J., and J. M. Wilson. Expression of alpha v beta 5 integrin is necessary for efficient adenovirus-mediated gene transfer in the human airway. *J. Virol.*, 69, 5951-8 (1995).

Goldman, M., Q. Su, and J. M. Wilson. Gradient of RGD-dependent entry of adenoviral vector in nasal and intrapulmonary epithelia: implications for gen therapy of cystic fibrosis. *Gene Ther.*, 3, 811-818 (1996).

Gommerman, J. L., R. Rottapel, and S. A. Berger. Phosphatidylinositol 3-kinase and Ca2+ influx dependence for ligand-stimulated internalization of the c-Kit receptor. *J. Biol. Chem.*, 272, 30519-25 (1997).

Gottlieb, T. A., I. E. Ivanov, M. Adesnik, and D. D. Sabatini. Actin microfilaments play a critical role in endocytosis at the apical but not the basolateral surface of polarized epithelial cells. *J. Cell Biol.*, 120, 695-710 (1993).

Griffiths, G., B. Hoflack, K. Simons, I. Mellman, and S. Kornfeld. The mannose 6-phosphate receptor and the biogenesis of lysosomes. *Cell*, 52, 329-41 (1988).

Halbert, C. L., T. A. Standaert, M. L. Aitken, I. E. Alexander, D. W. Russell, and A. D. Miller. Transduction by adeno-associated virus vectors in the rabbit airway: efficiency, persistence, and readministration. *J. Virol.*, 71, 5932-41 (1997).

Hansen, J., K. Qing, H. J. Kwon, C. Mah, and A. Srivastava. Impaired intracellular trafficking of adeno-associated virus type 2 vectors limits efficient transduction of murine fibroblasts [In Process Citation]. *J. Virol.*, 74, 992-996 (2000).

Hirt, B. Selective extraction of polyoma DNA from infected mouse cell cultures. *J. Mol. Biol.*, 26, 365-9 (1967).

Hughes, S. E. and P. A. Hall. Immunolocalization of fibroblast growth factor receptor 1 and its ligands in human tissues. *Lab Invest.*, 69, 173-82 (1993).

Jeggo, P. A., A. M. Carr, and A. R Lehmann. Cloning human DNA repair genes. *Int. J. Radiat. Biol.*, 66, 573-7 (1994).

Jensen, T. J., M. A. Loo, S. Pind, D. B. Williams, A. L. Goldberg, and J. R. Riordan. Multiple proteolytic systems, including the proteasome, contribute to CFTR processing. *Cell*, 83, 129-35 (1995).

Jiang, Q., D. Mak, S. Devidas, E. M. Schwiebert, A. Bragin, Y. Zhang, W. R. Skach, W. B. Guggino, J. K. Foskett, and J. F. Engelhart. Cystic fibrosis transmembrane conductance regulator-associated ATP release is controlled by a chloride sensor. *J. Cell Biol.*, 143, 645-57 (1998).

Kao, A. W., B. P. Ceresa, S. R. Santeler, and J. E. Pessin. Expression of a dominant interfering dynamin mutant in 3T3L1 adipocytes inhibits GLUT4 endocytosis without affecting insulin signaling. *J. Biol. Chem.*, 273, 25450-7 (1998).

Kaplitt, M. G., P. Leone, R. J. Samulski, X. Xiao, D. W. Pfaff, K. L. O'Malley, and M. J. During. Long-term gene expression and phenotypic correction using adeno-associated virus vectors in the mammalian brain. *Nat. Genet.*, 8, 148-54 (1994).

Kato, G. J. Human genetic diseases of proteolysis. *Hum. Mutat.*, 13, 87-98 (1999).

Kloetzel, P. M. The proteasome system: a neglected tool for improvement of novel therapeutic strategies? [editorial] *Gene Ther.*, 5, 1297-98 (1998).

Kondo, M., W. E. Finkbeiner, and J. H. Widdicombe. Simple technique for culture of highly differentiated cells from dog tracheal epithelium. *Am. J. Physiol.*, 261, L106-17 (1991).

Kotin, R. M., M. Siniscalco, R. J. Samulski, X. D. Zhu, L. Hunter, C. A. Laughlin, S. McLaughlin, N. Buzyczka, M. Rocchi and K I. Berns. Site-specific integration by adeno-associated virus. *Proc. Natl. Acad. Sci. USA*, 87, 2211-2215 (1990).

Lebkowski, J. S., M. M. McNally, T. B. Okarma, and L. B. Lerch. Adeno-associated virus: a vector system for efficient introduction and integration of DNA into a variety of mammalian cell types. *Mol. Cell Biol.*, 8, 3988-96 (1988).

Li, E., D. Stupack, G. M. Bokoch, and G. R. Nemerow. Adenovirus endocytosis requires actin cytoskeleton reorganization mediated by Rho family GTPases. *J. Virol.*, 72, 8806-12 (1998).

Li, E., D. Stupack, R. Klemke, D. A. Cheresh, and G. R. Nemerow. Adenovirus endocytosis via alpha(v) integrins requires phosphoinositide-3-OH kinase. *J. Virol.*, 72, 2055-61 (1998).

Lim, D. S., D. G. Kirsch, C. E. Canman, J. H. Ahn, Y. Ziv, L. S. Newman, R. B. Darnell, Y. Shiloh, and M. B. Kastan.

ATM binds to beta-adaptin in cytoplasmic vesicles. *Proc. Natl. Acad. Sci. USA,* 95, 10146-51 (1998).

Mah, C., K. Qing, B. Khuntirat, S. Ponnazhagan, X. S. Wang, D. M. Kube, M. C. Yoder, and A. Srivastava Adeno-associated virus type 2-mediated gene transfer: role of epidermal growth factor receptor protein tyrosine kinase in transgene expression. *J. Virol.,* 72, 9835-43 (1998).

Martys, J. L., C. Wjasow, D. M. Gangi, M. C. Kielian, T. E. McGraw, and J. M. Backer. Wortmannin-sensitive trafficking pathways in Chinese hamster ovary cells. Differential effects on endocytosis and lysosomal sorting. *J. Biol. Chem.,* 271, 10953-62 (1996).

Memmo, L. M., and P. McKeown-Longo. The alphavbeta5 integrin functions as an endocytic receptor for vitronectin. *J. Cell Sci.,* 111, 425-33 (1998).

Meresse, S., J. P. Gorvel, and P. Chavrier. The rab7 GTPase resides on a vesicular compartment connected to lysosomes. *J. Cell Sci.,* 108, 3349-58 (1995).

Mizukami, J., N. S. Young, and K E. Brown. Adeno-associated virus type 2 binds to a 150-kilodalton cell membrane glycoprotein. *Virology,* 217, 124-30 (1996).

Mu, F. T., J. M. Callaghan, O. Steele-Mortimer, H. Stenmark, R. G. Parton, P. L. Campbell, J. McCluskey, J. P. Yeo, E. P. Tock, and B. H. Toh. EEA1, an early endosome-associated protein. EEA1 is a conserved alpha-helical peripheral membrane protein flanked by cysteine "fingers" and contains a calmodulin-binding IQ motif. *J. Biol. Chem.,* 270, 13503-11 (1995).

Muzyczka, N. Use of adeno-associated virus as a general transduction vector for mammalian cells. *Curr. Top. Microbiol. Immunol.,* 158, 97-129 (1992).

Naim, H. Y., D. T. Dodds, C. B. Brewer, and M. G. Roth. Apical and basolateral coated pits of MDCK cells differ in their rates of maturation into coated vesicles, but not in the ability to distinguish between mutant hemagglutin proteins with different internalization signals. *J. Cell Biol.,* 129, 1241-50 (1995).

Obin, M., E. Mesco, X. Gong, A. L. Haas, J. Joseph, and A. Taylor. Neurite outgrowth in PC12 cells. Distinguishing the roles of ubiquitilation and ubiquitin-dependent proteolysis. *J. Biol. Chem.,* 274, 11789-95 (1999).

Odorizzi, G., and I. S. Trowbridge. Structural requirements for basolateral sorting of the human transferrin receptor in the biosynthetic and endocytic pathways of Madin-Darby canine kidney cells. *J. Cell Biol.,* 137, 1255-64 (1997).

Odorizzi, G. A., Pearse, D. Domingo, I. S. Trowbridge, and C. R. Hopkins. Apical and basolateral endosomes of MDCK cells and interconnected and contain a polarized sorting mechanism. *J. Cell Biol.,* 135, 139-152 (1996).

Paillard, F. Glycotargeting: a receptor-mediated delivery using sugar ligands [comment]. *Hum. Gene Ther.,* 10, 337-9 (1999).

Park, E., S. N. Guzder, M. H. Koken, I. Jaspers-Dekker, G. Weeda, J. H. Hoeijmakers, S. Prakash, and L. Prakash. RAD25 (SSL2), the yeast homolog of the human xeroderma pigmentosum group B DNA repair gene, is essential for viability. *Proc. Natl. Acad. Sci. USA,* 89, 11416-20 (1992).

Peters, K., S. Werner, X. Liao, S. Wert, J. Whitsett, and L. Williams. Targeted expression of a dominant negative FGF receptor blocks branching morphogenesis and epithelial differentiation of the mouse lung. *Embo J.,* 13, 3296-301 (1994).

Pickles, R J., D. McCarty, H. Matsui, P. J. Hart, S. H. Randell, and R. C. Boucher. Limited entry of adenovirus vectors into well-differentiated airway epithelium is responsible for inefficient gene transfer [In Process Citation]. *J. Virol.,* 72, 6014-23 (1998).

Ponnazhagan, S., D. Erickson, W. G. Kearns, S. Z. Zhou, P. Nahreini, X. S. Wang, and A. Srivastava. Lack of Site-Specific integration of the recombinant adeno-associate virus 2 genomes in human cells. *Hum. Gene Ther.,* 8, 275-284 (1997).

Powell, P. P., C. C. Wang, H. Horinouchi, K. Shepherd, M. Jacobson, M. Lipson, and R. Jones. Differential expression of fibroblast growth factor receptors 1 to 4 and ligand genes in late fetal and early postnatal rat lung. *Am. J. Respir. Cell Mol. Biol.,* 19, 563-72 (1998).

Prasad, K. M., and J. P. Trempe. The adeno-associated virus Rep78 protein is covalently linked to viral DNA in a preformed virion. *Virology,* 214, 360-70 (1995).

Prydz, K., S. H. Hansen, K. Sandvig, and B. van Deurs. Effects of brefeldin A on endocytosis, transcytosis and transport to the Golgi complex in polarized MDCK cells. *J. Cell Biol.,* 112, 259-72 (1992).

Qing, K., T. Bachelot, P. Mukherjee, X. S. Wang, L. Peng, M. C. Yoder, P. Leboulch, A. Srivastava Adeno-associated virus type 2-mediated transfer of ecotropic retrovirus receptor cDNA allows ecotropic retroviral transduction of established and primary cells. *J. Virol.,* 71(7), 5663-7 (1997).

Qing, K., X. S. Wang, D. M. Kube, S. Ponnazhagan, A. Bajpai, and A. Srivastava. Role of tyrosine phosphorylation of a cellular protein in adeno-associate virus 2-mediated transgene expression. *Proc. Natl. Acad. Sci. USA.* 94, 10879-84 (1997).

Qing, K., C. Mah, J. Hansen, S. Zhou, V. Dwarki, and A. Srivastava. Human fibroblast growth factor receptor 1 is a co-receptor for infection by adeno-associated virus 2 [In Process Citation]. *Nat. Med.,* 5, 71-7 (1999).

Recchia, A., R. J. Parks, S. Lamartina, C. Toniatti, L. Pieroni, F. Palombo, G. Ciliberto, F. L. Graham, R. Cortese, N. La Monica, and S. Colloca. Site-specific integration mediated by a hybrid adenovirus/adeno-associated virus vector. *Proc. Natl. Acad. Sci. USA,* 96, 2615-2620 (1999).

Rock, K. L., C. Gramm, L. Rothstein, K Clark, R. Stein, L. Dick, D. Hwang, and A. L. Goldberg. Inhibitors of the proteasome block the degradation of most cell proteins and the generation of peptides presented on MHC class I molecules. *Cell,* 78, 761-71 (1994).

Rodriguez, D., J. R. Rodriguez, G. K. Ojakian, and M. Esteban. Vaccinia virus preferentially enters polarized epithelial cells through the basolateral surface. *J. Virol.,* 65, 494-8 (1991).

Rodriguez-Boulan, E., and C. Zurzolo. Polarity signals in epithelial cells. *J. Cell Sci. Suppl.,* 17, 9-12 (1993).

Rubin, D. M., and D. Finley. Proteolysis. The proteasome: a protein-degrading organelle. *Curr. Biol.,* 5, 854-858 (1995).

Russell, D. W., A. D. Miller, and I. E. Alexander. Adeno-associated virus vectors preferentially transduce cells in S phase. *Proc. Natl. Acad. Sci. USA,* 91, 8915-9 (1994).

Russell, D. W., I. E. Alexander, and A. D. Miller. DNA synthesis and topoisomerase inhibitors increase transduction by adeno-associated virus vectors. *Proc. Natl. Acad. Sci. USA.* 92, 5719-23 (1995).

Samulski, R. J., L. S. Chang, and T. Shenk. A recombinant plasmid from which an infectious adeno-associated virus genome can be excised in vitro and its use to study viral replication. *J. Virol.,* 61, 3096-101 (1987).

Samulski, R. J., X. Zhu, X. Xiao, J. D. Brook, D. E. Housman, N. Epstein, and L. A. Hunter. Targeted integration of adeno-associated virus (AAV) into human chromosome 19 [published erratum appears in *EMBO J.,* 11(3), 1228 (1992)]. *EMBO J.,* 10, 3941-3950, (year).

Sanlioglu, S., and J. Engelhardt. Cellular redox state alters recombinant adeno-associated virus transduction through tyrosine phosphatase pathways. *Gene Ther.,* 6, 1427-37 (1999).

Sanlioglu, S., D. Duan, and J. F. Engelhardt. Two Independent Molecular Pathways Augment rAAV Transduction in the Presence of UV-C and E4-ORF6. *Human Gene Therapy,* 10, 591-602 (1999).

Sato, S. B., T. Taguchi, S. Yamashina, and S. Toyama Wortmannin and Li+ specifically inhibit clathrin-independent endocytic internalization of bulk fluid. *J. Biochem,* (Tokyo), 119, 887-97 (1996).

Schwartz, O., V. Marechal. B. Friguet, F. Arenzana Seisdedos, and J. M. Heard. Antiviral activity of the proteasome on incoming human immunodeficiency. *J. Virol.,* 72, 3845-50 (1998).

Schwartz, A. L., and A. Ciechanover. The ubiquitin-proteasome pathway and pathogenesis of human diseases. *Annu. Rev. Med.,* 50, 57-74 (1999).

Seglen, P. O. Inhibitors of lysosomal function. *Methods Enzymol.,* 96, 737-64 (1983).

Sharma, P., L. Dudus, P. A. Nielsen, H. Clausen, J. R. Yankaskas, M. A. Hollingsworth, and J. F. Engelhardt. MUC5B and MUC7 are differentially expressed in mucous and serous cells of submucosal glands in human bronchial airways. *Am. J. Respir. Cell Mol. Biol.,* 19, 30-7 (1998).

Shiomi, T., Y. Harada, T. Saito, N. Shiomi, Y. Okuno, and M. Yamaizumi. An ERCC5 gene with homology to yeast RAD2 is involved in group G xeroderma pigmentosum. *Mutat. Res.,* 314, 167-75 (1994).

Snyder, R. O., C. H. Miao, G. A. Patijn, S. K. Spratt, O. Danos, D. Nagy, A. M. Gown, B. Winther, L. Meuse, L. K. Cohen, A. R. Thompson, and M. A. Kay. Persistent and therapeutic concentrations of human factor IX in mice after hepatic gene transfer of recombinant AAV vectors. *Nat. Genet.,* 16, 270-6 (1997).

Strouss, G. J., and R. Govers. The ubiquitin-proteasome system and endocytosis. *J. Cell Sci.,* 112, 1417-1423 (1999).

Summerford, C., and R. J. Samulski. Membrane-associated heparan sulfate proteoglycan is a receptor for adeno-associated virus type 2 virions. *J. Virol.,* 72, 1438-45 (1998).

Summerford, C., J. S. Bartlett, and R. J. Samulski. AlphaVbeta5 integrin: a co-receptor for adeno-associated virus type 2 infection [In Process Citation]. *Nat. Med.,* 5, 78-82 (1999).

Teramoto, S., J. S. Bartlett, D. McCarty, X. Xiao, R. J. Samulski, and R. C. Boucher. Factors influencing adeno-associated virus-mediated gene transfer to human cystic fibrosis airway epithelial cells: comparison with adenovirus vectors. *J. Virol.,* 72, 8904-12 (1998).

Thompson, L. H., K W. Brookman, N. J. Jones, S. A. Allen, and A. V. Carrano. Molecular cloning of the human XRCC1 gene, which corrects defective DNA strand break repair and sister chromatid exchange. *Mol. Cell Biol.,* 10, 6160-71 (1990).

Thompson, L. H., K W. Brookman, C. A. Weber, E. P. Salazar, J. T. Reardon, A. Sancar, Z. Deng, and M. J. Siciliano. Molecular cloning of the human nucleotide-excision-repair gene ERCC4. *Proc. Natl. Acad. Sci. USA,* 91, 6855-9 (1994).

Tomkinson, A. E., and Z. B. Mackey. Structure and function of mammalian DNA ligases. *Mutat. Res.,* 407, 1-9 (1998).

Tugizov, S., E. Maidji, and L. Pereira Role of apical and basolateral membranes in replication of human cytomegalovirus in polarized retinal pigment epithelial cells. *J. Gen. Virol.,* 77, 61-74 (1996).

Vihinen-Ranta, M., A. Kalela, P. Makinen, L. Kakkola, V. Marjomaki, and M. Vuento. Intracellular route of canine parvovirus entry. *J. Virol.,* 72, 802-6 (1998).

Waite, R. L., J. W. Sentry, H. Stenmark, and B. H. Toh. Autoantibodies to a novel early endosome antigen 1. *Clin. Immunol. Immunopathol.,* 86, 81-7 (1998).

Walters, R. W., T. Grunst, J. M. Bergelson, R. W. Finberg, M. J. Welsh, and J. Zabner. Basolateral localization of fiber receptors limits adenovirus infection from the apical surface of airway epithelia *J. Biol. Chem.,* 274, 10219-26 (1999).

Walters, R. W., D. Duan, J. F. Engelhardt, and M. J. Elsh. Incorporation of adeno-associated virus in a calcium phosphate coprecipitate improves gene transfer to airway epithelia in vitro and in vivo. *J. Virol.,* 74, 535-540 (2000).

Wang, G., B. L. Davidson, P. Melchert, V. A. Slepushkin, H. H. van Es, M. Bodner, D. J. Jolly, and P. B. McCray, Jr. Influence of cell polarity on retrovirus-mediated gene transfer to differentiated human airway epithelia. *J. Virol.,* 72, 9818-26 (1998).

Wang, K., S. Huang, A. Kapoor-Munshi, and G. Nemerow. Adenovirus internalization and infection require dynamic. *J. Virol.,* 72, 3455-8 (1998).

Weber, C. A., E. P. Salazar, S. A. Stewart, and L. H. Thompson. Molecular cloning and biological characterization of a human gene, ERCC2, that corrects the nucleotide excision repair defect in CHO UV5 cells. *Mol. Cell Biol.,* 8, 1137-46 (1988).

Westerveld, A., J. H. Hoeijmakers, M. van Duin, J. de Wit, H. Odijk, A. Pastink, R. D. Wood, and D. Bootsma Molecular cloning of a human DNA repair gene. *Nature,* 310, 425-9 (1984).

Wickham, T. J., D. M. Segal, P. W. Roelvink, M. E. Carrion, A. Lizonova, G. M. Lee, I Kovesdi. Targeted adenovirus gene transfer to endothelial and smooth muscle cells by using bispecific antibodies. *J. Virol.,* 70(10), 6831-8 (1996).

Wickham, T. J., P. W. Roelvink, D. E. Brough, I. Kovesdi. Adenovirus targeted to heparan-containing receptors increases its gene delivery efficiency to multiple cell types. *Nat. Biotechnol.,* 14(11), 1570-3 (1996).

Wills, N. K., L. Reuss, and S. A. Lewis. *Epithelial transport: a guide to methods and experimental analysis,* 1st ed., Chapman & Hall, London; New York (1996).

Wojcik, C. Inhibition of the proteasome as a therapeutic approach. *Drug Discovery Today,* 4, 188-189 (1999).

Xiao, X., J. Li, and R. J. Samulski. Efficient long-term gene transfer into muscle tissue of immunocompetent mice by adeno-associated virus vector. *J. Virol.,* 70, 8098-108 (1996).

Xiao, X., W. Xiao, J. Li, and R. J. Samulski. A novel 165-base-pair terminal repeat sequence is the sole cis requirement for the adeno-associated virus life cycle. *J. Virol.,* 71, 941-8 (1997).

Xiao, W., S. C. Berta, M. M. Lu, A. D. Moscioni, J. Tazelaar, and J. M. Wilson. Adeno-associated virus as a vector for liver-directed gene therapy. *J. Virol.,* 72, 10222-6 (1998).

Yang, J., W. Zhou, Y. Zhang, T. Zidon, T. Ritchie, and J. F. Engelhardt. Concatamerization of Adeno-associated Viral Circular Genomes Occurs Through Intermolecular Recombination. *J. Virol.,* 73, 9468-77 (1999).

Yukawa, H., S. I. Miyatake, M. Salki, J. C. Takahashi, T. Mima, H. Ueno, I. Nagata, H. Kikuchi, and N. Hashimoto.

In vitro growth suppression of vascular smooth muscle cells using adenovirus-mediated gene transfer of a truncated form of fibroblast growth factor receptor. *Atherosclerosis,* 141, 125-32 (1998).

Zabner, J., S. C. Wadsworth, A. E. Smith and M. J. Welsh. Adenovirus-mediated generation of cAMP-stimulated Cl-transport in cystic fibrosis airway epithelia in vitro: effect of promoter and administration method. *Gene Ther.,* 3, 458-65 (1996).

Zabner, J., B. G. Zeiher, E. Friedman, and M. J. Welsh. Adenovirus-mediated gene transfer to ciliated airway epithelia requires prolonged incubation time. *J. Virol.,* 70, 6994-7003 (1996).

Zabner, J., P. Freimuth, A. Puga, A. Fabrega, and M. J. Welsh. Lack of high affinity fiber receptor activity explains the resistance of ciliated airway epithelia to adenovirus infection. *J. Clin. Invest.,* 100, 1144-9 (1997).

Zhang, Y., B. Doranz, J. R. Yankaskas, and J. F. Engelhardt. Genotypic analysis of respiratory mucous sulfation defects in cystic fibrosis. *J. Clin. Invest.,* 96, 2997-3004 (1995).

Zhang, Y., J. Yankaskas, J. Wilson, and J. F. Engelhardt. In vivo analysis of fluid transport in cystic fibrosis airway epithelia of bronchial xenografts. *Am. J. Physiol.,* 270, C1326-35 (1996).

Zhang, Y., Q. Jiang, L. Dudus, J. R. Yankaskas, and J. F. Engelhardt. Vector-specific complementation profiles of two independent primary defects in cystic fibrosis airways. *Hum. Gene Ther.,* 9, 635-48 (1998).

Zwacka, R. M., W. Zhou, Y. Zhang, C. J. Darby, L. Dudus, J. Halldorson, L. Oberley, and J. F. Engelhardt. Redox gene therapy for ischemia/reperfusion injury of the liver reduces AP1 and NF-kappaB activation. *Nat. Med.,* 4, 698-704 (1998).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to enhance adeno-associated virus (AAV) transduction of a mammalian lung cell or a mammalian liver cell, comprising: directly contacting the mammalian lung cell or the mammalian liver cell with the AAV and administering a proteasome inhibitor in an amount effective to enhance transduction of the AAV wherein the transduction is enhanced relative to transduction of a mammalian lung cell or a mammalian liver cell comprising the AAV that is not administered the proteasome inhibitor, wherein the inhibitor has two amino acids linked by a peptide bond or three amino acids linked by peptide bonds, which inhibitor optionally has a N-terminal blocking group, a C-terminal blocking group, or both.

2. The method of claim 1 wherein the virus is rAAV.

3. The method of claim 2 wherein the rAAV encodes a therapeutic peptide or a therapeutic polypeptide.

4. A method to enhance the expression of a transgene operably linked to an expression control sequence in a mammalian lung cell or a mammalian liver cell, comprising: contacting the mammalian lung cell or the mammalian liver cell with an amount of a proteasome inhibitor and directly administering a recombinant AAV (rAAV) comprising the transgene, wherein the amount enhances expression of the transgene, wherein the expression is enhanced relative to expression in a mammalian lung cell or a mammalian liver cell comprising the rAAV but that is not contacted with the proteasome inhibitor, wherein the inhibitor has two amino acids linked by a peptide bond or three amino acids linked by peptide bonds, which inhibitor optionally has a N-terminal blocking group, a C-terminal blocking group, or both.

5. The method of claim 4 wherein the transgene encodes a therapeutic peptide or a therapeutic polypeptide.

6. The method of claim 1 or 4 wherein the cell is contacted with the inhibitor before the cell is contacted with the virus.

7. The method of claim 1 or 4 wherein the cell is contacted with the virus before the cell is contacted with the inhibitor.

8. A method comprising: providing a mammal having cells subjected to therapy with a rAAV comprising a transgene operably linked to an expression control sequence, the expression of which in the mammal is therapeutic, and administering to the mammal a proteasome inhibitor in an amount effective to enhance expression of the transgene in the cells of the mammal wherein the expression is enhanced relative to expression in cells in a mammal comprising the rAAV but that are not contacted with the proteasome inhibitor, wherein the inhibitor has two amino acids linked by a peptide bond or three amino acids linked by peptide bonds, which inhibitor optionally has a N-terminal blocking group, a C-terminal blocking group, or both.

9. The method of claim 8 wherein the transgene encodes a therapeutic peptide or a therapeutic polypeptide.

10. The method of claim 8 wherein the expression is enhanced in the mammalian lung cells.

11. The method of claim 8 wherein the expression is enhanced in the mammalian liver cells.

12. The method of claim 4 or 8 wherein the transgene encodes Factor VIII.

13. A method to enhance AAV transduction of a mammalian cell, comprising: directly contacting the mammalian cell with the AAV and administering a proteasome inhibitor in an amount effective to enhance transduction of the AAV wherein the transduction is enhanced relative to a mammal having cells contacted with the AAV but that is not administered the proteasome inhibitor, wherein the inhibitor has two amino acids linked by a peptide bond or three amino acids linked by peptide bonds, which inhibitor optionally has a N-terminal blocking group, a C-terminal blocking group, or both.

14. A method to enhance AAV transduction in a mammal in need of therapy, comprising: directly administering to the mammal a rAAV encoding a therapeutic gene product encoded by an open reading frame operably linked to an expression control sequence and administering a proteasome inhibitor in an amount effective to enhance transduction of the rAAV wherein the transduction is enhanced relative to transduction in cells of a mammal comprising the rAAV but that is not administered the inhibitor, wherein the inhibitor has two amino acids linked by a peptide bond or three amino acids linked by peptide bonds, which inhibitor optionally has a N-terminal blocking group, a C-terminal blocking group, or both.

15. The method of claim 1, 13 or 14 wherein the virus is rAAV that encodes Factor VIII.

16. The method of claim 14 wherein the transduction in liver of the mammal is enhanced.

17. The method of claim 14 wherein the inhibitor is intravenously administered.

18. The method of claim 8 or 14 wherein the rAAV and the inhibitor are concurrently administered.

19. The method of claim 13 or 14 wherein the proteasome inhibitor is a cysteine protease inhibitor.

20. The method of claim 13 or 14 wherein the proteasome inhibitor is a peptide analog.

21. The method of claim 13 or 14 wherein the proteasome inhibitor is a compound of formula (I): $R_1$-A-$(B)_n$—C wherein $R_1$ is an N-terminal amino acid blocking group; each A and B is independently an amino acid; C is an amino acid wherein the terminal carboxy group has been replaced by a formyl (CHO) group; and n is 0 or 1; or a pharmaceutically acceptable salt thereof.

22. The method of claim 13 or 14 wherein the proteasome inhibitor is a compound of formula (II):

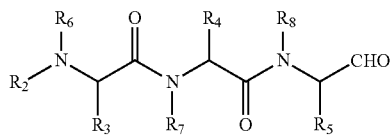

(II)

wherein $R_2$ is an N-terminal amino acid blocking group;

$R_3$, $R_4$, and $R_5$ are each independently hydrogen, ($C_1$-$C_{10}$) alkyl, aryl or aryl($C_1$-$C_{10}$)alkyl; and $R_6$, $R_7$, and $R_8$ are each independently hydrogen, ($C_1$-$C_{10}$) alkyl, aryl or aryl($C_1$-$C_{10}$)alkyl;

or a pharmaceutically acceptable salt thereof.

23. The method of 1, 4, 8, 13, or 14 wherein one of the amino acids is a non-naturally occurring amino acid.

24. The method of claim 23 wherein the non-naturally occurring amino acid is nor-leucine.

25. The method of 1, 4, 8, 13, or 14 wherein the proteasome inhibitor is directly administered.

\* \* \* \* \*

UNITED STATES PATENT AND TRADEMARK OFFICE
CERTIFICATE OF CORRECTION

PATENT NO.       : 8,846,030 B2                                    Page 1 of 1
APPLICATION NO.  : 11/301601
DATED            : September 30, 2014
INVENTOR(S)      : Engelhardt et al.

It is certified that error appears in the above-identified patent and that said Letters Patent is hereby corrected as shown below:

In the Specification

Column 1, line 16-19, delete "This invention was made at least in part with a grant from the Government of the United States of America (Contract No. HL 58340 from the National Institutes of Health). The Government may have certain rights in the invention." and insert --This invention was made with government support under HL58340 awarded by the National Institutes of Health. The government has certain rights in the invention.--, therefor Column 6, line 4, after "thereof", insert --.--, therefor Column 11, line 50, delete "ells" and insert --cells,--, therefor Column 38, line 61, delete "uv" and insert --UV--, therefor Column 38, line 65, delete "uv" and insert --UV--, therefor Column 60, line 20, delete "112" and insert --119--, therefor In the Claims Column 64, line 49, Claim 13, after "administered", insert --to--, therefor Column 64, line 65, Claim 14, after "administered", insert --to--, therefor Signed and Sealed this
Thirtieth Day of June, 2015

Michelle K. Lee
*Director of the United States Patent and Trademark Office*